US008043807B2

(12) United States Patent
Livneh et al.

(10) Patent No.: US 8,043,807 B2
(45) Date of Patent: Oct. 25, 2011

(54) METHODS AND KITS FOR DETERMINING A RISK TO DEVELOP CANCER, FOR EVALUATING AN EFFECTIVENESS AND DOSAGE OF CANCER THERAPY AND FOR CORRELATING BETWEEN AN ACTIVITY OF A DNA REPAIR ENZYME AND A CANCER

(75) Inventors: Zvi Livneh, Rehovot (IL); Tamar Paz-Elizur, Rehovot (IL); Sara Blumenstein, Ramat Gan (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 401 days.

(21) Appl. No.: 10/469,992

(22) PCT Filed: Mar. 21, 2002

(86) PCT No.: PCT/IL02/00231
§ 371 (c)(1),
(2), (4) Date: Sep. 16, 2003

(87) PCT Pub. No.: WO02/076280
PCT Pub. Date: Oct. 3, 2002

(65) Prior Publication Data
US 2004/0096863 A1    May 20, 2004

Related U.S. Application Data

(63) Continuation-in-part of application No. 09/815,015, filed on Mar. 23, 2001, now abandoned.

(60) Provisional application No. 60/303,338, filed on Jul. 9, 2001.

(51) Int. Cl.
*C12Q 1/68* (2006.01)
*C07H 21/04* (2006.01)

(52) U.S. Cl. ........................ 435/6.1; 536/23.1

(58) Field of Classification Search ........................ None
See application file for complete search history.

(56) References Cited

U.S. PATENT DOCUMENTS

| 5,482,833 | A | * | 1/1996 | Pero et al. ........................ 435/6 |
| 5,482,837 | A | | 1/1996 | Albertini |
| 2001/0031739 | A1 | | 10/2001 | Dare |
| 2003/0003454 | A1 | | 1/2003 | Livneh et al. |

FOREIGN PATENT DOCUMENTS

| JP | 62-224300 | 10/1987 |
| WO | WO 98/01838 | 1/1998 |
| WO | WO 99/04626 | 2/1999 |
| WO | WO 02/077280 | 10/2002 |

OTHER PUBLICATIONS

Menegazzi et al. (1999) Correlation of Poly(ADP-ribose)polymerase and p53 expression levels in high-grade lymphomas. Molecular Carcinogenesis. 25:256-261.*

Bouchard et al. PARP-1, a determinant of cell survival in response to DNA damage. Experimental Hematology (2003) 31: 446-454.*
Chalmers, A.J. Poly(ADP-ribose) polymerase-1 and ionizing radiation: sensor, signaller and therapeutic target. Clinical Oncology (2004) 16: 29-39.*
Loft et al. Cancer risk and oxidative DNA damage in man. Journal of Molecular Medicine (1996) 74: 297-312.*
Suzuki et al. Changes in the urinary excretion level of 8-hydroxyguanine by exposure to reactive oxygen-generating substrates. Free Radical Biology & Medicine (1995) 18(3): 431-436.*
Shinmura et al. Expression of the OGG1-type 1a (nuclear form) protein in cancerous and non-cancerous human cells. International Journal of Oncology (2000) 16: 701-707.*
Wei et al. Reduced expression of hMLH1 and hGTBP/hMSH6: a risk factor for head and neck cancer. Cancer Epidemiology, Biomarkers, and Prevention (1998) 7: 309-314.*
Silber et al. Lack of the DNA repair protein O6-methylguanine-DNA methyltransferase in histologically normal brain adjacent to primary brain tumors. Proceedings of the National Academy of Sciences, USA (1996) 93: 6941-6946.*
Silber et al. Comparison of O6-methylguanine-DNA methyltransferase activity in brain tumors and adjacent normal brain. Cancer Research (1993) 53: 3416-3420.*
Gu et al. Human MutY homolog, a DNA glycosylase involved in base excision repair, physically and functionally interacts with mismatch repair proteins human MutS homolog 2/Human MutS homolog 6. The Journal of Biological Chemistry (2002) 277(13): 11135-11142.*
Wei et al. Reduced expression of mismatch repair genes measured by multiplex reverse transcripion-polymerase chain reaction in human gliomas. Cancer Research (1997) 57: 1673-1677.*
Lu et al. A mammalian DNA repair enzyme that excises oxidatively damaged guanines maps to a locus frequently lost in lung cancer. Current Biology (1997) 7: 397-407.*
Audebert et al. Effect of single mutations in the OGG1 gene found in human tumors on the substrate specificity of the Ogg1 protein. Nucleic Acids Research (2000) 28(14): 2672-2678.*
Wiencke et al. Correlation of DNA Adducts in Blood Mononuclear Cells with Tobacco Carcinogen-induced Damage in Human Lung. Cancer Research (1995) 55: 4910-4914.*
Radak et al. Lung cancer in smoking patients inversely alters the activity of hOGG1 and hNTH1. Cancer Letters (2005) 219: 191-195.*
Blons et al. Frequent Allelic Loss at Chromosome 3p Distinct from Genetic Alterations of the 8-Oxoguanine DNA Glycosylase 1 Gene in Head and Neck Cancer. Molecular Carcinogenesis (1999) 26: 254-260.*
Park et al. Genetic changes of hOGG1 and the activity of oh8Gua glycosylase in colon cancer. European Journal of Cancer (2001) 37: 340-346.*
Cheng et al. Reduced DNA repair capacity in head and neck cancer patients. Cancer Epidemiology, Biomarkers & Prevention (1998) 7: 465-468.*
Collins et al. Repair of oxidative DNA damage: assessing its contribution to cancer prevention. Mutagenesis (2002) 17(6): 489-493.*

(Continued)

*Primary Examiner* — Young J Kim
*Assistant Examiner* — Angela Bertagna

(57) ABSTRACT

Methods and kits for (i) determining a risk of a subject to develop cancer; (ii) evaluating an effectiveness and dosage of cancer therapy administered to a cancer patient; and (iii) determining a presence of correlation or non-correlation between an activity of at least one DNA repair enzyme and at least one cancer, are disclosed.

13 Claims, 11 Drawing Sheets

OTHER PUBLICATIONS

Wei et al. The role of DNA repair capacity in susceptibility to lung cancer: A review. Cancer and Metastasis Reviews (1997) 16: 295-307.*

Koybasi et al. Defects in Cell Growth Regulation by C18:0-Ceramide and Longevity Assurance Gene 1 in Human Head and Neck Squamous Cell Carcinomas. The Journal of Biological Chemistry (2004) 279(43): 44311-44319.*

Janssen et al. DNA repair activity of 8-oxoguanine DNA glycosylase 1 (OGG1) in human lymphocytes is not dependent on genetic polymorphism Ser326/Cys326. Mutation Research (2001) 486: 207-216.*

Collins et al. Inter-individual differences in repair of DNA base oxidation, measured in vitro with the comet assay. Mutagenesis (2001) 16(4): 297-301.*

Rajaee-Behbahani et al. Altered DNA repair capacity and bleomycin sensitivity as risk markers for non-small cell lung cancer. International Journal of Cancer (2001) 95: 86-91.*

Wei et al. Repair of tobacco carcinogen-induced DNA adducts and lung cancer risk: a molecular epidemiologic study. Journal of the National Cancer Institute (2000) 92(21): 1764-1772.*

Sagher et al. "Low O6-Alkylguanine DNA Alkyltranferase Activity in the Peripheral Blood Lymphocytes of Patients with Therapy-Related Acute Nonlymphocytic Leukemia", Cancer Research 48: 3084-3089, 1988.

Sagher et al. "Heterogeneity of O6-Alkylguanine-DNA Alkyltransferase Activity in Peripheral Blood Lymphocytes: Relationship between this Activity in Lymphocytes and in Lymphoblastoid Lines from Normal Controls and from Patients with Hodgkin's Disease or Non-Hodgkin's Lymphoma", Cancer Reseaerch, 49: 5339-5344, 1989.

Shinmura et al. "Infrequent Mutation of the hOGG1 Gene, that is Involved in the Excision of 8-Hydroxyguanine in Damaged DNA, in Human Gastric Cancer", Jpn. J. Cancer Research, 89: 825-828, 1998.

Srivastava et al. "Germ-Line Transmission of a Mutated p53 Gene in a Cancer-Prone Family with Li-Fraumeny Syndome", Natur, 348: 747-749, 1990.

Strauss "Translesion DNA Synthesis: Polymerase Response to Altered Nucleotides", Cancer Surveys, 4(3): 494-516,1985.

Vandenbroucke et al. "Increased Risk of Venous Thrombosis in Oral-Contraceptive Users who are Carriers of Factor V Leiden Mutation", The Lancet, 344: 1453-1457,1994.

Vogelstein et al. "The Multistep Nature of Cancer", TIG,9(4), 1993.

Singhal et al. "DNA Polymerase β Conducts the Gap-Filling Step in Uracil-Initiated Base Excision Repair in a Bovine Testis Nuclear Extract", The Journal of Biological Chemistry, 270(2): 949-957, 1995.

Weeda et al. "Genes Controlling Nucleotide Excision Repair in Eukaryotic Cells", Bio Essays, 15(4): 249-258, 1993.

Wei et al. "Reduced DNA Repair Capacity in Lung Cancer Patients", Cancer Research, 56:4103-4107, 1996.

Wei et al. "DNA Repair and Aging in Basal Cell Carcinoma: A Molecular Epidemiology Study", PNAS,90: 1614-1618, 1993.

Wei et al. "DNA Repair and Susceptibility to Basal Cell Carcinoma: A Case-Control Study", American Journal of Epidemiology, 140(7): 598-607,1994.

Weinberg "Oncogenes, Antioncogenes, and the Molecular Base of Multstep Carcinogenesis",Cancer Research, 49:3713-3721, 1989.

Wikman et al. "hOGG1 Polymorphism and Loss of Hetrozygosity (LOH): Significance for Lung Cancer Suspectibility in a Caucasian Population", In. Journal of Cancer, 88: 932-937, 2000.

Wood et al. "Mechnistic Studies of ionizing Radiation and Oxidative Mutagenesis: Genetic Effects of a Single 8-Hydroxyguanine (7-Hydro-8-Oxoguanine) Residue Inserted at a Unique Site in a Viral Genome", Biochemistry, 29: 7024-7032, 1990.

Kang et al. "Intracellular Localization of 8-Oxo-dGTPase inHuman Cells, with Special Reference to the Role of the Enzyme in mitochondria", The Journal of Biological Chemistry, 270(24): 14659-14665, 1995.

Krokan et al. "Base Excision Repair of DNA in Mammalian Cells", FEBS Letters, 476: 73-77, 200.

Ladner et al. "The Human dUTPase Gene Encodes Both Nuclear and Mitochondrial Isoforms", The Journal of Biological Chemistry, 272(30): 19072-19080, 1997.

Mo et al. "Hydrolytic Elimination of a Mutagenic Nucleotide, 8-OxodGTP, by Human 18-Kilodalton Protein: Sanitization of Nucleotide Pool", PNAS, 89(22): 11021-11025, 1992.

Prasad et al. "Human DNA Polymerase β Deoxyribose Phosphate Lyase", The Journal of Bioligical Chemistry, 273(24): 15263-15270, 1998.

Parker et al. "Purification and Characterization of a Mammalian Homolog of *Escherichia coli* Mut γ Mismatch Repair Protein From Caalf Liver Mitochondria", Nucleic Acids Research, 28(17): 3206-3215, 2000.

Slupphaug et al. "Properties of a Recombinant human Uracil-DNA Glycosylase from the UNG Gene and Evidence that UNG Encodes the Major Uracil-DNA Glycosylase", Biochemistry, 34: 128-138, 1995.

Srivastava etal. "Phorbol Ester Abrogates Up-Regulation of DNA Polymerase β by DNA-Alkylating Agents in Chinese Hamster Ovary Cells", The Journal of Bioligical Chemistry, 270(27): 16402-16408, 1995.

Srivastava et al. "DNA Polymerase β Expression Differences in Selected human Tumors and Cell Lines", Carcinogenesis, 20(6): 1049-1054, 1999.

Wilson et al. "Incision Activity of Human Apurinic Endonuclease (Ape) at Abasic Site Analogs in DNA", The Journal of Biological Chemistry, 270(27): 16002-16007, 1995.

Wood et al. "Human DNA Repair Genes", Science, 291: 1284-1289, 2001.

Wood et al. "Human DNA Repair Genes", Science, 291: 1284-1289, 2001.

Krokan et al. "Base Excision Repair of DNA in Mammalian Cells", FEBS Letters, 476: 73-77, 2000.

Asami et al. "Increase of a type of Oxidative DNA Damage, 8-Hydroxyguanine, and its Repair Activity in Human Leukocytes by Cigarette Smoking", Cancer Research, 56: 2546-2549, 1996. Claims: 1-66.

Shinmura et al. "Infrequent Mutations of the hOGG1 Gene, that is Involved in the Excision of 8-Hydroxyguanine in Damaged DNA, in Human Gastric Cancer", Japanese Journal of Cancer Research, 89: 825-828, 1998. Claims: 1-66.

Kow et al. "Detection of Abasic Sites and Oxidative DNA Base Damage Using an ELISA-Like Assay", Methods, 22: 164-169, 2000. Claims: 1-66.

Bouziane et al. "Promoter Structure and Cell Cycle Dependent Expression of the Human Methylpurine DNA Glycosylase Gene", Mutation Research, 461: 15-29, 2000. Claims: 1-66.

Aburatani et al. "Cloning and Charcterization of Mammalian8-Hydroxyguanine-Specific DNA Glycosylase /Apurinic, Apyrimidinic Lyase, a Functional MutM Homologue",Cancer Reaearch, 57: 215-2156, 1997.

Arai et al. "Cloning of a Human Homolog of the Yeast OGGI Gene that is Involved in the Repair of Oxidative DNA Damage", Oncogene, 14: 2857-2861, 2997.

Asami et al. "Increase of a Type of Oxidative DNA Damage, 8-Hydroxyguanine, and its Repair Activity in Human Leukocytes by Cigarette Smoking", Cancer Research, 56: 2546-2549, 1996.

Asami et al. "Cigarette Smoking Induces an Increase in Oxidative DNA, 8-Hydroxydeoxyguanosine, in a Central Site of the Human Lung", Carcinogenesis, 18: 1763-1766, 1997.

Athas et al. "Development and Field-Test Validation of an Assay for DNA Repair in Circulating Human Lymphocytes", Cancer Research, 51: 5786-5793, 1991.

Auckley et al. Reduced DNA-Dependent Protein Kinase Activity is Associated with Lung Cancer, Carcinogenesis, 22:(5), 723-727, 2001.

Audebert et al. "Alterations of the DNA Repair Gene OGGI in Human Clear Cell Carcinomas of the Kidney", Cancer Research, 60: 4740-4744, 2000.

Bessho et al. "Repair of 8-Hydroxyguanine in DNA by MammalinaN-Methylpurine-DNA Glycosylase",Proc. National Acad. Science, 90: 8901-8904, 1993.

Bishop "Cancer: The Rise of the Genetic Paradigm", Genes & Development, 9: 1309-1315, 1995.

Bjoras et al. "Opposite Base-Dependent Reactions of a Human Base Excision Repair enzymen on DNA Containing 7,8-Dihydro-8-Oxoguanine and Abasic Sites", The EMBO Journal, 16(20): 6314-6322, 1997.

Collins "Oxidative DNA Damage, Antioxidants, and Cancer", BioEssays, 21(3): 238-246, 1999.

Connor et al. "Tumorigenesis and a DNA Repair Defect in Mice with a Truncating Brca2 Mutation", Nature Genetics, 17: 423-430, 1997.

Dianov et al. "Generation of Single-Nucleotide Repair Patches Following Exision of Uracil Residues from DNA", Molecular and Cellular Biology, 12(4): 1605-1612, 1992.

Echols et al. "Ridelity Mechanisms in DNA Replication", Annu. Rev. Biochem.,60: 477-511, 1991.

Engelward et al. "Base Excision Repair Deficient Mice Lacking the Aag Alkyladenine DNA Glycosulase",Proc. Natl. Acad. Science, 94: 13087-13092, 1997.

Fishel et al. "The Human Mutator Gene Homolog MSH2 and its Association with Hereditary Nonpolyposis Colon Cancer", Cell, 75: 1027-1038,1993.

Fortini et al. "Different DNA Polymerases Are Involved in the Short- and Long-Patch Base Excision Repair in Mammalian Cells", Biochemistry, 37(11): 3575-3580, 1998.

Gajewski et al. "Modification of DNA Bases in Mammalian Chromatin by Radiation-Generated Free Radicals", Biochemistry, 29: 7876-7882, 1990.

Gown et al. "BRCA1 Required for Transcription-Coupled Repair of Oxidative DNA Damage", Science, 281, 5379: 1009(4), 1998.

Hanawalt "Transcription-Coupled Repair and human Disease", Science, 266, 5193: 1957, 1994.

Hang et al. "Targeted Deletion of Alkylpurine-DNA-N-Glycosylase in Mice Eliminates Repair of 1,N6-Ethenoadenine and Hypoxanthine But not of 3,N4-Ethenocytosine or 8-Oxyguanine", PNAS, 94: 12869-12874, 1997.

Hazra et al. "The Presence of Two Distinct 8-Oxoguanine Repair Enzymes inHuman Cells: Their Potential Complementary Roles in Preventing Mutation",Nucleic Acids Research, 26(22): 5116-5122, 1998.

Helzlsouer et al. "DNA Repair Proficiency: Potential Susceptibility Factor for Breast Cancer", Brief Communications, J. of the Natl. Cancer Institute, 88(11):754-755, 1996.

Hernandez et al. "IARC p53 Mutation Database: A Relational Database to Compile amd Analyze p53 Mutations in Human Tumors and Cell Lines", Human Mutation, 14: 1-8, 1999.

Hollstein et al. "Somatic Point Mutations in the p53 Gene of Human Tumors and Cell Lines: Updated Compilation", Nucleic Acids Research, 24(1): 141-146, 1996.

Hutchinson "Chemical Changes Induced in DNA by Ionizing Radiation", Nucleic Acid Research and Molecular Biology, 32: 115-154, 1985.

Hyun et al. "Leukemic Cell Line,KG-1 has a Functional Loss of hOGG1 Enzyme Due to a Point Mutation and 8-Hydroxydeoxyguanosine Can Kill KG-1", Oncogene, 19, 4476-4479, 2000.

Ishida et al. "Structure and Chromosome Location of Human OGG1", Cytogenet Cell Genet, 85: 232-236, 1999.

Jyothish et al. Cancer Letters, 124: 9-13, 1998.

Kim et al. "Involvement of Flap Endonuclease 1 in Base Excision DNA Repair", The journal of Biological Chemistry, 273(15): 8842-8848, 1998.

Klungland et al. "Accumulation of Premutagenic DNA Lesions in Mice Defective in Removal of Oxidative Base Damage", ONAS, 96(23): 13300-13305, 1999.

Kyrtopoulos et al. "Studies in Gastric Carcinogenesis. IV O6-Methylguanine and its Repair in Normal and Atrophic Biopsy Specimens of Human Gastric Mucosa. Correlation of a O6-Alkylguanine-DNA Alkyltranserase Activities in gastric Muscosa and Circulating Lymphocytes", Carcinogenesis, 11(3): 431-436, 1990.

Laval "Expression of the *E.coli* fpg Gene in Mammalian Cells Reduces the Mutagenicity of γ-Rays", Nucleic Acids Research, 22(23): 4943-4946, 1994.

Page et al. Transcription-Coupled Repair of 8-OXoGuanine: Requirement for XPG, TFIIH, and CSB and Implications for Cockayne Syndrome, Cell, 101, 159-171, 2000.

Page et al. "BRCA1 and BRCA2 are Necessary for the Transcription-Coupled Repair of the Oxidative 8-Oxoguanine Lesion in Human Cells", Cancer Research, 60: 55548-5552, 2000.

Leach et al. "Mutations of a MutS Homolog in Hereditary Nonpolyposis Colorectal Cancer", Cell, 75, 1215-1225, 1993.

Leanderson et al. "Cigarette Smoke-Induced DNA Damage in Cultured human Lung Cells: Role of hydroxyl Radicals and Endonuclease Activation", Chem. Biol. Interactions, 91: 197-208, 1992.

Lindahl "Instability and Decay of the Primary Structure of DNA", Nature, 362: 709-715, 1993.

Lippman et al. "Lung Cancer Chemoprevention: An Integrated Approach", Journal of Clinical Oncology, 19(18): 74-82, 2001.

Livneh et al. "Replication of Damaged DNA and the Molecular Mechanism of Ultraviolet Light Mutagenesis", Critical Revies in Biochemistry and Molecular Biology, 28(6): 465-513, 1993.

Lu et al. "A Mammalian DNA Repair Enzyme that Excises Oxidatively Damaged Guanines Maps to a Locus Frequently Lost in Lung Cancer", Harvard University, Dept. of Chemistry and Chemical Biology, Research Paper: 397-407, 1997.

Maki et al. "Mut T Protein Specially Hydrolyses a Potent Mutagenic Substrate for DNA Synthesis", Nature, 355, 273-275, 1992.

Mattson et al. "What are the Odds that Smoking Will Kill You ?", AJPH, 77,(4), 1987.

Minna et al. "Focus on Lung Cancer", Cencer CEL, 1: 49-52, 20002.

Minowa et al. "Mmh/Ogg1 Gene Inactivation Results in Accumulation of 8-Hydroxyguanine in Mice", PNAS, 97,(8): 4156-4161, 2000.

Modrich "Mismatch Repair, Genetic Stability, and Cancer", Science, 266(5193): 1959, 1994.

Monden et al. "Human MMh (OGG1) Type 1a Protein is a Major Enzyme for Repair of8-Hydroxyguanine Lesions in Human Cells", Biochmical aand Biophysical Research Communications, 258: 605-610, 1999.

Parshad et al. "Deficient DNA Repair Capacity, a Predisposing Factor in Breast Cancer", British Journal of Cancer, 74: 1-5, 1996.

Parsons et al. "Hypermutability and Mismatch Repair Deficiency in RER Tumor Cells", Cell, 75: 1227-1236,1993.

Patel et al. "Involvement of Brca2 in DNA Repair", Molecular Cell, 1: 347-357, 1998.

Patel et al. "DNA Repair Proficiency in Breast Cancer Patients and their First-Degree Relatives", Int. J. of Cancer, 73: 20-24, 1997.

Pavlov et al. "DNA Replication Fidelity with 8-Oxodeoxyguanosine Triphosphate", Biochemistry, 33: 4695-4701, 1994.

Radicella et al. "Cloning and Characterization of hOGG1, a Human Homolog of the OGG1 Gene of *Saccharamyces cerevisiae*", PNAS, 94: 8010-8015, 1997.

Reardon et al. "In-Vitro Repair of Oxidative DNA Damage by Human Nucleotide Excision Repair System: Possible Explanation forNeurodegeneration in Xeroderma Pigmentosum Patients", PNAS, 94, 9463-9468, 1997.

Roldan-Arjona et al. "Molecular Cloning and Functional Expression of a Human cDNA Encoding the Antimutator Enzyme 8-Hydroxyguanine-DNA Glycosylase", PNAS, 94: 8016-8020, 1997.

Rosenquist "Cloning and Charcterization of a Mammalian 8-Oxyoguanine DNA Glycosylase",PNAS, 94: 7429-7434, 1997.

Rünger et al. "Repair of Ultraviolet B and Singlet Oxygen-Induced DNA Damage in Xeroderma Pigmentosum Cells", The Journal of Investigative Dermatology, 104(1): 68-73, 1995.

Sagher et al. "Low O6-Alkylguanine DNA Alkyltransferase Activity in the Peripheral Blood Lymphocytes of Patients with Therapy-Related Acute Nonlumphocytic Leukemia",Cncer Research, 48: 3084-3089, 1988.

Sancar "Mechanisms of DNA Excision Repair", Science, 266(5193): 1954, 1994.

Savitsky et al. "A Single Ataxia Telangiectasia Gene with a Product Similar to PI-3 Kinase", Scienc, 268 ( 5218): 1749-1753, 1995.

Scully et al. "Association of BRCA1 with Rad51 in Mitotic and Meiotic Cells", Cell, 88, 265-275, 1997.

Sharan et al. "Embryonic Lethality and Radiation Hypersensitivity Mediated by Rad51 in Mice Lacking Brca2",Nature, 386: 804-810, 1997.
Shibutani et al. "Insertion of Specific Bases During DNA Synthesis Past the Oxidation-Damaged Base 8-OxodG", Nature, 349: 431-434, 1991.
Communication Pursuant to Article 94(3) EPC Dated May 19, 2008 From the European Patent Office Re.: Application No. 02707078.8.
Examiner's Report Dated Aug. 11, 2006 From the Australian Government, IP Australia Re.: Application No. 2002241230.
Examiner's Report Dated Sep. 25, 2007 From the Australian Government, IP Australia Re.: Application No. 2002231230.
International Preliminary Examination Report Dated Oct. 10, 2004 From the International Searching Authority Re.: Application No. PCT/IL02/00231.
International Preliminary Examination Report Dated Sep. 20, 2004 From the International Preliminary Examining Authority Re.: Application No. PCT/IL02/00231.
International Search Report Dated Jun. 9, 2003 From the International Searching Authority Re.: Application No. PCT/IL02/00231.
Official Action Dated Jun. 27, 2007 From the Israeli Patent Office Re.: Application No. 158003.
Supplementary European Search Report Dated Jul. 13, 2006 From the European Patent Office Re.: Application No. 02707078.8.
Translation of the Official Action Dated Nov. 6, 2007 From the Japanese Patent Office Re.: Application No. 2002-574802.
Written Opinion Dated Jan. 7, 2004 From the International Preliminary Examining Authority Re.: Application No. PCT/IL02/00231.
Official Action Dated Feb. 6, 2002 from the US Patent and Trademark Office Re: U.S. Appl. No. 09/815,015.
Official Action dated Apr. 18, 2002 from US Patent and Trademark Office Re: U.S. Appl. No. 09/815,015.
Official Action Dated Jan. 21, 2003 from the US Patent and Trademark Office Re.: U.S. Appl. No. 09/815,015.
Translation of the Official Action Dated Aug. 1, 2008 From the Japanese Patent Office Re.: Application No. 2002-574802.
Cheng et al. "Reduced Expression Levels of Nucleotide Excision Repair Genes in Lung Cancer: A Case-Control Analysis", Carcinogenesis, 21(8): 1527-1530, 2000.
Gowen et al. "BRCA1 Required for Transcription-Coupled Repair of Oxidative DNA Damage", Science, 281(5379): 1009(4), 1998.
Koistenen et al. "Hematopoietic and Gastric Uracil-DNA Glycosylase Activity in Megaloblastic Anemia and in Atrophic Gastritis With Special Reference to Pernicious Anemia", Carcinogenesis, 8(2): 327-331, 1987. Abstract.
Koistenen et al. "Uracil-DNA Glycosylase Activity in Human Acute Leukemia", Leukemia Research, 11(6): 557-563, 1987.
Ladner et al. "dUTP Nucleotidohydrolase Isoform Expression in Normal and Neoplastic Tissues: Association With Survival and Response to 5-Fluorouracil in Colorectal Cancer", Cancer Research, 60: 3493-3503, 2000.
Preuss et al. "Activity of the DNA Repair Protein O6-Methylguanine-DNA Methyltransferase in Human Tumor and Corresponding Normal Tissue", Cancer Detection and Prevention, 20(2): 130-136, 1996.
Preuss et al. "O6-Methylguanine-DNA Methyltransferase Activity in Breast and Brain Tumors", International Journal of Cancer, 61: 321-326, 1995.
Shirota et al. "ERCC1 and Thymidylate Synthase mRNA Levels Predict Survival for Colorectal Cancer Patients Receiving Combination Oxaliplatin and Fluorouracil Chemotherapy", Journal of Clinical Oncology, 19(23): 4298-4304, 2001.
Soliman et al. "Reduced Expression of Mismatch Repair Genes in Colorectal Cancer Patients in Egypt", International Journal of Oncology, 12(6): 1315-1319, 1998.
Audebert et al. "Alterations of the DNA Repair Gene OGG1 in Human Clear Cell Carcinomas of the Kidney", Cancer Research, 60: 4740-4744, 2000.
Sugimura et al: "HOGG1 Ser326Cys Polymorphism and Lung Cancer Susceptibility", Cancer Epidemiology, Biomarkers & Prevention, 8: 669-674, Aug. 1999.
Office Action Dated Apr. 2, 2009 From the Israeli Patent Office Re.: Application No. 158003 and Its Translation Into English.
Office Action Dated Jun. 27, 2007 From the Israeli Patent Office Re.: Application No. 158003.
Response Dated May 4, 2009 to Official Action of Jan. 6, 2009 From the United States Patent and Trademark Office Re.: U.S. Appl. No. 10/469,992.
Vineis et al "A Field Synopsis on Low-Penetrance Varians in DNA Repari Genes and Cancer Susceptibility", J. Natl. Cancer Inst. 101:24-36, 2009.
Communication Pursuant to Article 94(3) EPC Dated Nov. 9, 2009 From the European Patent Office Re.: Application No. 02707078.8.
Requisition by the Examiner Dated Aug. 13, 2009 From the Canadian Intellectual Property Office Re.: Application No. 2,441,436.
Response Dated Jan. 3, 2010 to Communication Pursuant to Article 94(3) EPC of Nov. 9, 2009 From the European Patent Office Re.: Application No. 02707078.8.
Response Dated Feb. 9, 2010 to Requisition by the Examiner of Aug. 13, 2009 From the Canadian Intellectual Property Office Re.: Application No. 2,441,436.
Damia et al. "Expression of Genes Involved in Nucleotide Excision Repair and Sensitivity to Cisplatin and Melphalan in Human Cancer Cell Lines", European Journal of Cancer, 34(11): 1783-1788, 1998.
Echols et al. "Fidelity Mechanisms in DNA Replication", Annual Reviews in Biochemistry, 60: 477-511, 1991.
Jyothish et al. "DNA Repair Proficiency: A Potential Marker for Identification of High Risk Members in Breast Cancer Families", Cancer Letters, 124: 9-13, 1998.
Krokan et al. "Base Excision Repair of DNA in Mammalian Cells", FEBS Letters, 476: 73-77, 2000.
Parshad et al. "Deficient DNA Repair Capacity, A Predisposing Factor in Breast Cancer", British Journal of Cancer, 74: 1-5, 1996.
Patel et al. "DNA Repair Proficiency in Breast Cancer Patients and Their First-Degree Relatives", International Journal of Cancer, 73: 20-24, 1997.
Sagher et al. "Low O6-Alkylguanine DNA Alkyltranferase Activity in the Peripheral Blood Lymphocytes of Patients With Therapy-Related Acute Nonlymphocytic Leukemia", Cancer Research, 48: 3084-3089, 1988.
Communication Pursuant to Rule 58 EPC of Rule 159 EPC Dated Dec. 3, 2010 From the European Patent Office Re. Application No. 10181096.8.
Response Dated Jan. 6, 2011 to Communication Pursuant to Rule 58 EPC of Rule 159 EPC of Dec. 3, 2010 From the European Patent Office Re. Application No. 10181096.8.
Communication Pursuant to Article 94(3) EPC Dated Feb. 24, 2011 From the European Patent Office Re.: Application No. 02707078.8.
European Search Report and the European Search Opinion Dated Feb. 16, 2011 From the European Patent Office Re. Application No. 10181096.8.
Translation of the Official Action Dated Aug. 1, 2008 From the Japanese Patent Office Re.: Application No. 2002-574802.
Communication Pursuant to Article 94(3) EPC Dated Dec. 22, 2008 From the European Patent Office Re.: Application No. 02707078.8.
Communication Pursuant to Article 94(3) EPC Dated Feb. 24, 2011 From the European Patent Office Re.: Application No. 02707078.8.
European Search Report and the European Search Opinion Dated Feb. 16, 2011 From the European Patent Office Re. Application No. 10181096.8.
Examiner's Report Dated Sep. 25, 2007 From the Australian Government, IP Australia Re.: Application No. 2002231230.
Office Action Dated Oct. 20, 2010 From the Israel Patent Office Re. Application No. 205890 and Its Translation Into English.
Official Action Dated Apr. 18, 2002 From the US Patent and Trademark Office Re: U.S. Appl. No. 09/815,015.
Requisition by the Examiner Dated Oct. 27, 2010 From the Canadian Intellectual Property Office Re.: Application No. 2,441,436.
Response Dated Feb. 9, 2010 to Requisition by the Examiner of Aug. 13, 2009 From the Canadian Intellectual Property Office Re.: Application No. 2,441,436.
Response Dated Dec. 22, 2010 to Requisition by the Examiner of Oct. 27, 2010 From the Canadian Intellectual Property Office Re.: Application No. 2,441,436.

Aburatani et al. "Cloning and Characterization of Mammalian 8-Hydroxyguanine-Specific DNA Glycosylase/Apurinic, Apyrimidinic Lyase, A Functional MutM Homologue", Cancer Research, 57: 215-2156, 1997.

Arai et al. "Cloning of a Human Homolog of the Yeast OGGI Gene That Is Involved in the Repair of Oxidative DNA Damage", Oncogene, 14: 2857-2861, 1997.

Audebert et al. "Effect of Single Mutations in the OGG1 Gene Found in Human Tumors on the Substrate Specificity of the Ogg1 Protein", Nucleic Acids Research, XP002619409, 28(14): 2672-2678, 2000.

Bessho et al. "Repair of 8-Hydroxyguanine in DNA by Mammalian N-Methylpurine-DNA Glycosylase", Proc. Natl. Acad. Sci. USA, 90: 8901-8904, 1993.

Damia et al. "Expression of Genes Involved in Nucleotide Excision Repair and Sensitivity to Cisplatin and Melphalan in Human Cancer Cell Lines", European Journal of Cancer, 34(11): 1783-1788, 1998.

Dianov et al. "Generation of Single-Nucleotide Repair Patches Following Excision of Uracil Residues From DNA", Molecular and Cellular Biology, 12(4): 1605-1612, 1992.

Engelward et al. "Base Excision Repair Deficient Mice Lacking the Aag Alkyladenine DNA Glycosulase", Proc. Natl. Acad. Sci. USA, 94: 13087-13092, 1997.

Hanawalt "Transcription-Coupled Repair and Human Disease", Science, 266(5193): 1957-1959, 1994.

Hang et al. "Targeted Deletion of Alkylpurine-DNA-N-Glycosylase in Mice Eliminates Repair of 1,N6-Ethenoadenine and Hypoxanthine But Not of 3,N4-Ethenocytosine or 8-Oxyguanine", Proc. Natl. Acad. Sci. USA, 94: 12869-12874, 1997.

Hazra et al. "The Presence of Two Distinct 8-Oxoguanine Repair Enzymes in Human Cells: Their Potential Complementary Roles in Preventing Mutation", Nucleic Acids Research, 26(22): 5116-5122, 1998.

Helzlsouer et al. "DNA Repair Proficiency: Potential Susceptibility Factor for Breast Cancer", Brief Communications, Journal of the National Cancer Institute, 88(11): 754-755, 1996.

Hernandez et al. "IARC P53 Mutation Database: A Relational Database to Compile and Analyze P53 Mutations in Human Tumors and Cell Lines", Human Mutation, 14: 1-8, 1999.

Ishida et al. "Structure and Chromosome Location of Human OGG1", Cytogenetics and Cell Genetics, 85: 232-236, 1999.

Kang et al. "Intracellular Localization of 8-Oxo-dGTPase in Human Cells, With Special Reference to the Role of the Enzyme in Mitochondria", The Journal of Biological Chemistry, 270(24): 14659-14665, 1995.

Klungland et al. "Accumulation of Premutagenic DNA Lesions in Mice Defective in Removal of Oxidative Base Damage", Proc. Natl. Acad. Sci. USA, 96(23): 13300-13305, 1999.

Kyrtopoulos et al. "Studies in Gastric Carcinogenesis. IV. O6-Methylguanine and Its Repair in Normal and Atrophic Biopsy Specimens of Human Gastric Mucosa. Correlation of a O6-Alkylguanine-DNA Alkyltranserase Activities in Gastric Muscosa and Circulating Lymphocytes", Carcinogenesis, 11(3): 431-436, 1990.

Ladner et al. "The Human DUTPase Gene Encodes Both Nuclear and Mitochondrial Isoforms", The Journal of Biological Chemistry, 272(30): 19072-19080, 1997.

Laval "Expression of the E. coli Fpg Gene in Mammalian Cells Reduces the Mutagenicity of ?-Rays", Nucleic Acids Research, 22(23): 4943-4946, 1994.

Leanderson et al. "Cigarette Smoke-Induced DNA Damage in Cultured Human Lung Cells: Role of Hydroxyl Radicals and Endonuclease Activation", Chemical-Biological Interactions, 91: 197-208, 1992.

Livneh et al. "Replication of Damaged DNA and the Molecular Mechanism of Ultraviolet Light Mutagenesis", Critical Reviews in Biochemistry and Molecular Biology, 28(6): 465-513, 1993.

Lu et al. "A Mammalian DNA Repair Enzyme That Excises Oxidatively Damaged Guanines Maps to a Locus Frequently Lost in Lung Cancer", Harvard University, Dept. of Chemistry and Chemical Biology, Research Paper, Current Biology, 7: 397-407, May 12, 1997.

Maki et al. "MutT Protein Specifically Hydrolyses a Potent Mutagenic Substrate for DNA Synthesis", Nature, 355, 273-275, 1992.

Mattson et al. "What Are the Odds That Smoking Will Kill You ?", American Journal of Public Health, 77(4): 425-431, 1987.

Menegazzi et al. "Correlation of Poly(ADP-Ribose)Polymerase and P53 Expression Levels in High-Grade Lymphomas", Molecular Carcinogenesis, 25:256-261, 1999.

Minna et al. "Focus on Lung Cancer", Cancer Cell, 1: 49-52, 2002.

Minowa et al. "Mmh/Ogg1 Gene Inactivation Results in Accumulation of 8-Hydroxyguanine in Mice", Proc. Natl. Acad. Sci. USA, 97(8): 4156-4161, Apr. 11, 2000.

Mo et al. "Hydrolytic Elimination of a Mutagenic Nucleotide, 8-OxodGTP, by Human 18-Kilodalton Protein: Sanitization of Nucleotide Pool", Proc. Natl. Acad. Sci. USA, 89(22): 11021-11025, 1992.

Modrich "Mismatch Repair, Genetic Stability, and Cancer", Science, 266(5193): 1959-1962, 1994.

Monden et al. "Human MMH (OGG1) Type 1a Protein Is a Major Enzyme for Repair of 8-Hydroxyguanine Lesions in Human Cells", Biochemical and Biophysical Research Communications, 258: 605-610, 1999.

Page et al. "BRCA1 and BRCA2 Are Necessary for the Transcription-Coupled Repair of the Oxidative 8-Oxoguanine Lesion in Human Cells", Cancer Research, 60: 5548-5552, 2000.

Page et al. Transcription-Coupled Repair of 8-OxoGuanine: Requirement for XPG, TFIIH, and CSB and Implications for Cockayne Syndrome, Cell, 101, 159-171, 2000.

Parker et al. "Purification and Characterization of a Mammalian Homolog of *Escherichia coli* MutY Mismatch Repair Protein From Calf Liver Mitochondria", Nucleic Acids Research, 28(17): 3206-3215, 2000.

Pavlov et al. "DNA Replication Fidelity With 8-Oxodeoxyguanosine Triphosphate", Biochemistry, 33: 4695-4701, 1994.

Prasad et al. "Human DNA Polymerase ? Deoxyribose Phosphate Lyase", The Journal of Biological Chemistry, 273(24): 15263-15270, 1998.

Preuss et al. "Activity of the DNA Repair Protein O6-Methylguanine-DNA Methyltransferase in Human Tumor and Corresponding Normal Tissue", Cancer Detection and Prevention, 20(2): 130-136, 1996.

Preuss et al. "O6-Methylguanine-DNA Methyltransferase Activity in Breast and Brain Tumors", International Journal of Cancer, 61: 321-326, 1995.

Runger et al. "Repair of Ultraviolet B and Singlet Oxygen-Induced DNA Damage in Xeroderma Pigmentosum Cells", The Journal of Investigative Dermatology, 104(1): 68-73, 1995.

Radicella et al. "Cloning and Characterization of HOGG1, A Human Homolog of the OGG1 Gene of *Saccharamyces cerevisiae*", Proc. Natl. Acad. Sci. USA, 94: 8010-8015, 1997.

Reardon et al. "In Vitro Repair of Oxidative DNA Damage by Human Nucleotide Excision Repair System: Possible Explanation for Neurodegeneration in Xeroderma Pigmentosum Patients", Proc. Natl. Aacd. Sci. USA, 94, 9463-9468, 1997.

Roldan-Arjona et al. "Molecular Cloning and Functional Expression of a Human cDNA Encoding the Antimutator Enzyme 8-Hydroxyguanine-DNA Glycosylase", Proc. Natl. Acad. Sci. USA, 94: 8016-8020, 1997.

Rosenquist "Cloning and Characterization of a Mammalian 8-Oxyoguanine DNA Glycosylase", Proc. Natl. Acad. Sci. USA, 94: 7429-7434, 1997.

Sagher et al. "Heterogeneity of O6-Alkylguanine-DNA Alkyltransferase Activity in Peripheral Blood Lymphocytes: Relationship Between This Activity in Lymphocytes and in Lymphoblastoid Lines From Normal Controls and From Patients With Hodgkin's Disease or Non-Hodgkin's Lymphoma", Cancer Research, 49: 5339-5344, 1989.

Sagher et al. "Low O6-Alkylguanine DNA Alkyltranferase Activity in the Peripheral Blood Lymphocytes of Patients With Therapy-Related Acute Nonlymphocytic Leukemia", Cancer Research, 48: 3084-3089, 1988.

Sagher et al. "Low O6-Alkylguanine DNA Alkyltransferase Activity in the Peripheral Blood Lymphocytes of Patients With Therapy-Related Acute Nonlymphocytic Leukemia", Cancer Research, 48: 3084-3089, 1988.

Savitsky et al. "A Single Ataxia Telangiectasia Gene With a Product Similar to PI-3 Kinase", Science, 268 ( 5218): 1749-1753, 1995.

Shibutani et al. "Insertion of Specific Bases During DNA Synthesis Past the Oxidation-Damaged Base 8-OxodG", Nature, 349: 431-434, 1991.

Shinmura et al. "Infrequent Mutations of the hOGG1 Gene, That Is Involved in the Excision of 8-Hydroxyguanine in Damaged DNA, in Human Gastric Cancer", Japanese Journal of Cancer Research, XP002964057, 89: 825-828, 1998.

Singhal et al. "DNA Polymerase ? Conducts the Gap-Filling Step in Uracil-Initiated Base Excision Repair in a Bovine Testis Nuclear Extract", The Journal of Biological Chemistry, 270(2): 949-957, 1995.

Srivastava et al. "DNA Polymerase ? Expression Differences in Selected Human Tumors and Cell Lines", Carcinogenesis, 20(6): 1049-1054, 1999.

Srivastava et al. "Germ-Line Transmission of a Mutated P53 Gene in a Cancer-Prone Family With Li-Fraumeny Syndrome", Nature, 348: 747-749, 1990.

Srivastava etal. "Phorbol Ester Abrogates Up-Regulation of DNA Polymerase ? by DNA-Alkylating Agents in Chinese Hamster Ovary Cells", The Journal of Biological Chemistry, 270(27): 16402-16408, 1995.

Vineis et al. "A Field Synopsis on Low-Penetrance Variants in DNA Repair Genes and Cancer Susceptibility", Journal of the National Cancer Institute, 101(1): 24-36 & Suppl., Jan. 7, 2009.

Vogelstein et al. "The Multistep Nature of Cancer", TIG, 9(4): 4 P., 1993.

Wei et al. "DNA Repair and Aging in Basal Cell Carcinoma: A Molecular Epidemiology Study", Proc. Natl. Acad. Sci. USA, 90: 1614-1618, 1993.

Wikman et al. "HOGG1 Polymorphism and Loss of Hetrozygosity (LOH): Significance for Lung Cancer Suspectibility in a Caucasian Population", International Journal of Cancer, 88: 932-937, 2000.

Wood et al. "Mechanistic Studies of Ionizing Radiation and Oxidative Mutagenesis: Genetic Effects of a Single 8-Hydroxyguanine (7-Hydro-8-Oxoguanine) Residue Inserted at a Unique Site in a Viral Genome", Biochemistry, 29: 7024-7032, 1990.

Response Dated Feb. 20, 2011 to Office Action of Oct. 20, 2010 From the Israel Patent Office Re. Application No. 205890.

Translation of Official Query From Appeal Judge Dated Nov. 30, 2010 From the Japanese Patent Office Re.: Application No. 2002-574802.

Chevillard et al. "Mutations in OGG1, A Gene Involved in the Repair of Oxidative DNA Damage, Are Found in Human Lung and Kidney Tumours", Oncogene, 16: 3083-3086, 1998.

* cited by examiner

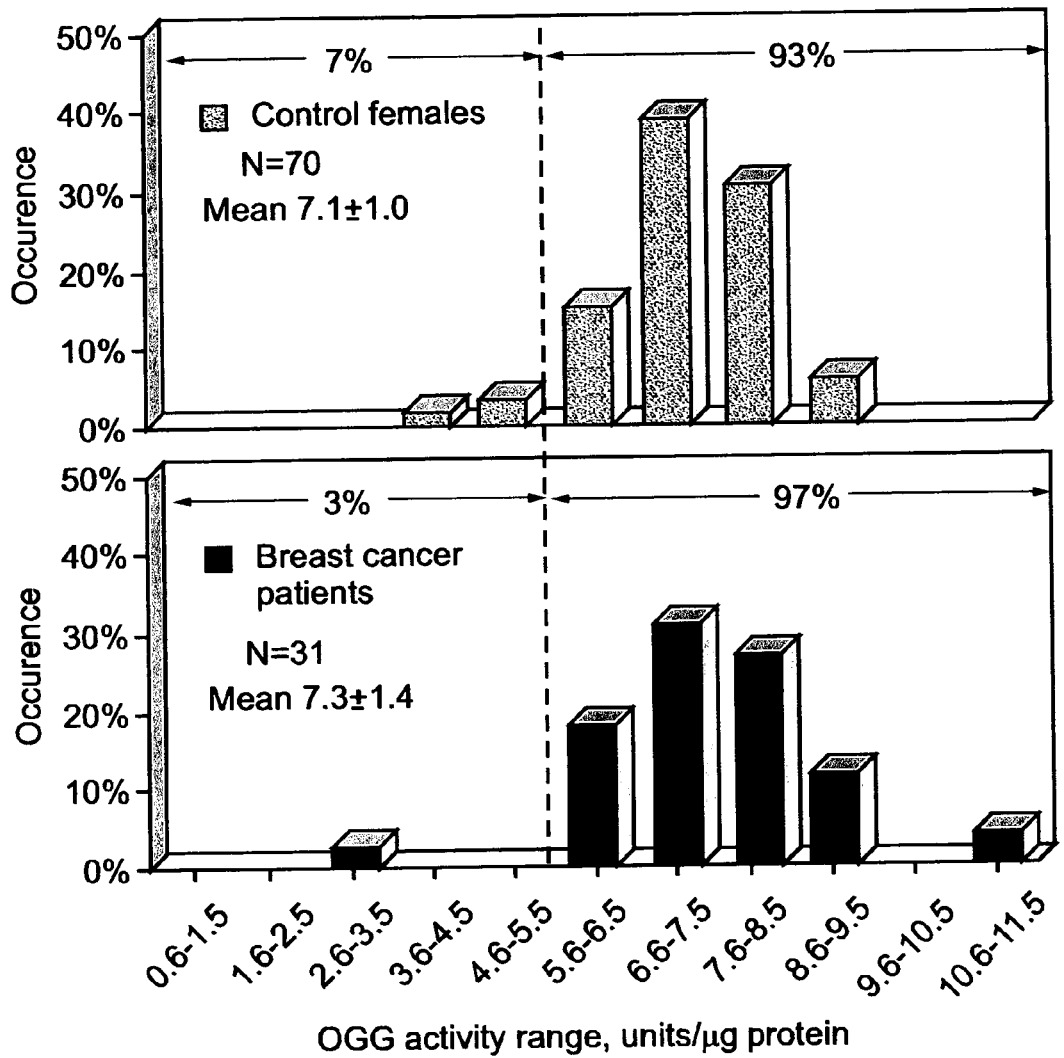

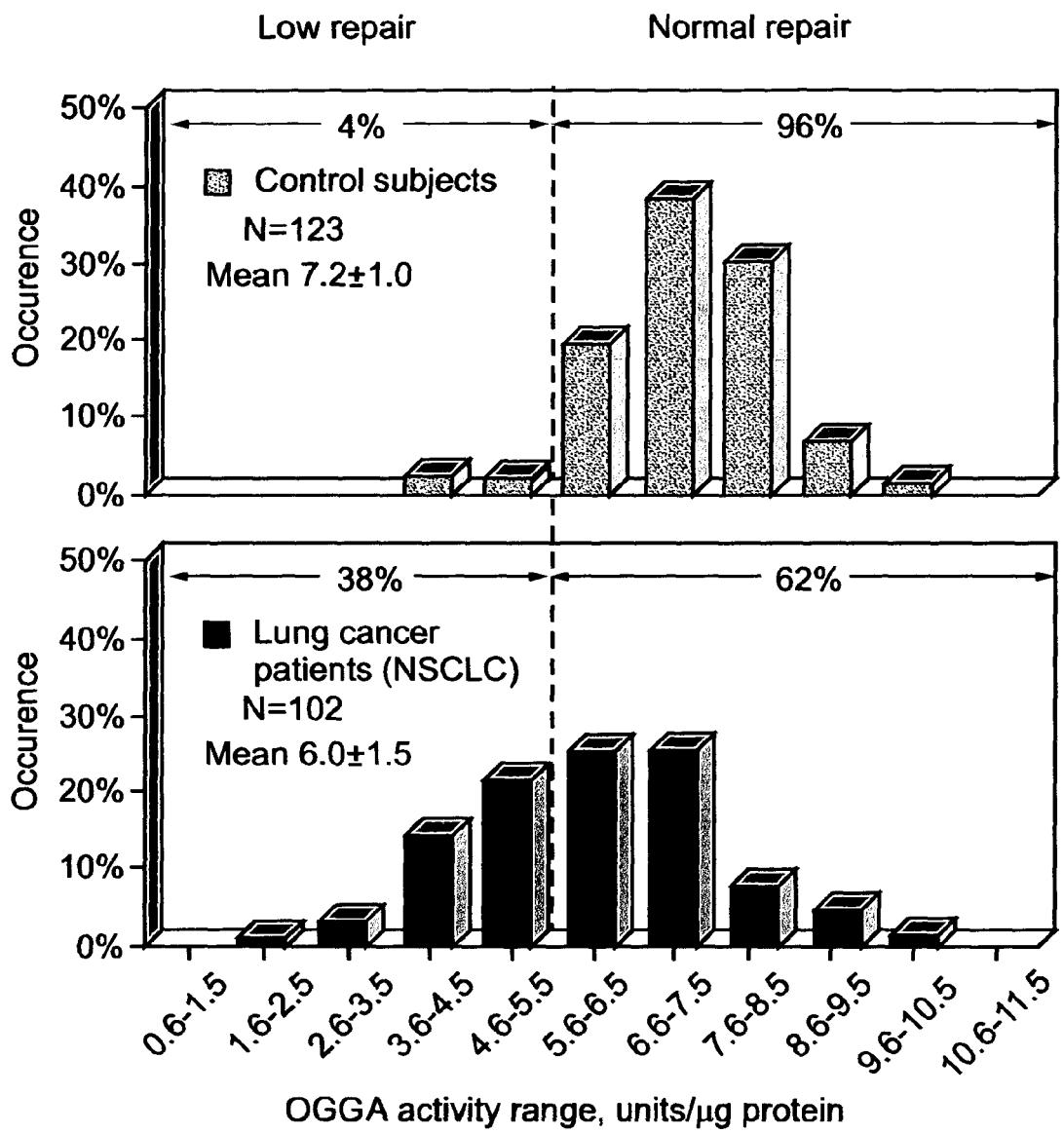

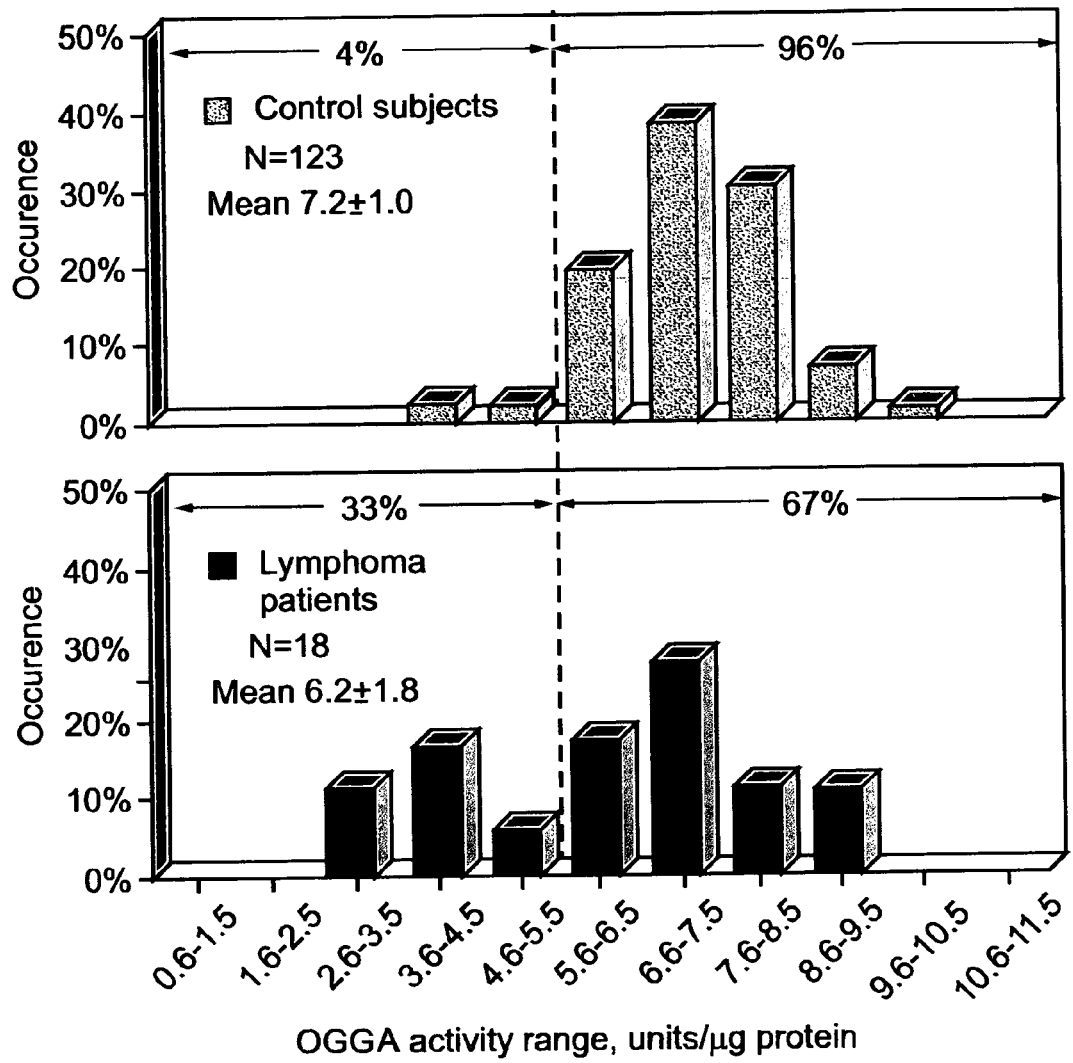

METHODS AND KITS FOR DETERMINING A RISK TO DEVELOP CANCER, FOR EVALUATING AN EFFECTIVENESS AND DOSAGE OF CANCER THERAPY AND FOR CORRELATING BETWEEN AN ACTIVITY OF A DNA REPAIR ENZYME AND A CANCER

RELATED APPLICATIONS

The present application is a National Phase Application of PCT Patent Application No. PCT/IL02/00231 having International Filing Date of Mar. 21, 2002 which is a Continuation-In-Part (CIP) of U.S. patent application Ser. No. 09/815,015, filed on Mar. 23, 2001, now abandoned, and claims priority from U.S. Provisional Patent Application No. 60/303,338, filed on Jul. 9, 2001.

FIELD AND BACKGROUND OF THE INVENTION

The present invention relates to the field of diagnosis and prognosis. More particularly, the present invention relates to methods of and kits for (i) determining a risk of a subject to develop cancer; (ii) evaluating an effectiveness and preferred dosage of cancer therapy administered to a cancer patient; and (iii) determining a presence of correlation or non-correlation between an activity of at least one DNA repair enzyme and at least one cancer.

The DNA in each cell of a body is constantly subjected to damage caused by both internal (e.g., reactive oxygen species) and external DNA damaging agents (e.g., sunlight, X- and γ-rays, smoke) (Friedberg, et al., 1995). Most lesions are eliminated from DNA by one of several pathways of DNA repair (Friedberg, et al., 1995, Hanawalt, 1994, Modrich, 1994, Sancar, 1994). When unrepaired DNA lesions are replicated, they cause mutations because of their miscoding nature (Echols and Goodman, 1991, Livneh, et al., 1993, Strauss, 1985). The occurrence of such mutations in critical genes, e.g., oncogenes and tumor suppressor genes, may lead to the development of cancer (Bishop, 1995, Vogelstein and Kinzler, 1993, Weinberg, 1989). Indeed, DNA repair has emerged in recent years as a critical factor in cancer pathogenesis, as a growing number of cancer predisposition syndromes have been shown to be caused by mutations in genes involved in DNA repair and the regulation of genome stability. These include Xeroderma Pigmentosum (Weeda, et al., 1993), Hereditary nonpolyposis colon cancer (Fishel, et al., 1993, Leach, et al., 1993, Modrich, 1994, Parsons, et al., 1993), Ataxia Telangiectasia (Savitsky, et al., 1995), Li-Fraumeni syndrome (Srivastava, et al., 1990), and the BRCA1 (Gowen, et al., 1998, Scully, et al., 1997) and BRCA2 genes (Connor, et al., 1997, Patel, et al., 1998, Sharan, et al., 1997). In these cases, which represent a minority of the cancer cases, gene mutations have caused malfunction, leading to a strong reduction in DNA repair.

A possible extension of the role of DNA repair in hereditary cancer, would be a role for DNA repair in sporadic cancer. Several studies suggested that inter-individual variability in DNA repair correlates with variation in cancer susceptibility, with low repair correlated to higher cancer risk (Athas, et al., 1991, Helzlsouer, et al., 1996, Jyothish, et al., 1998, Parshad, et al., 1996, Patel, et al., 1997, Sagher, et al., 1988, Wei, et al., 1996, Wei, et al., 1993, Wei, et al., 1994).

7,8-dihydro-8-oxoguanine (also termed 8-oxoguanine or 8-hydroxyguanine; dubbed 8-OxoG) is formed in DNA by two major pathways: (a) Modification of guanine in DNA by reactive oxygen species formed by intracellular metabolism, oxidative stress, cigarette smoke, or by radiation (Asami, et al., 1997, Gajewski, et al., 1990, Hutchinson, 1985, Leanderson and Tagesson, 1992). (b) Incorporation into DNA by DNA polymerases of 8-oxo-dGTP, which is formed by oxidation of intracellular dGTP (Maki and Sekiguchi, 1992). Once in DNA, 8-oxoG is replicated by DNA polymerases with the misinsertion of dAMP, causing characteristic GC to TA transversions (Shibutani, et al., 1991, Wood, et al., 1990). When the modified dGTP is used as a substrate by DNA polymerases, it is often misinserted opposite an A in the template, causing AT to CG transversions (Pavlov, et al., 1994).

The major route for removing 8-oxoG from DNA is base excision repair, initiated by 8-oxoguanine DNA N-glycosylase, product of the OGG1 gene (in humans termed also hOGG1; (Aburatani, et al., 1997, Arai, et al., 1997, Bjoras, et al., 1997, Radicella, et al., 1997, Roldan-Arjona, et al., 1997, Rosenquist, et al., 1997). The OGG1 gene was recently knocked-out in mice, such that the effects on carcinogenesis can now be examined in this organism (Klungland, et al., 1999, Minowa, et al., 2000). Expression of the E. coli enzyme in Chinese hamster cells reduced 4-fold the mutagenicity of γ radiation (Laval, 1994), indicating that the repair of 8-oxoG is important in negating the mutagenic activity of γ radiation. The following observations associate OGG1 with cancer: (i) OGG1 was mapped to chromosome 3p25, a site frequently lost in human lung and kidney cancers (Arai, et al., 1997, Audebert, et al., 2000, Ishida, et al., 1999, Lu, et al., 1997, Wikman, et al., 2000). (ii) OGG1 was found to be mutated in 2 out of 25 lung tumors (Chevillard, et al., 1998), and in 4 out of 99 renal tumors (Audebert, et al., 2000). (iii) OGG1 was found to be mutated in a leukemic cell line (Hyun, et al., 2000) and in a gastric cell line (Shinmura, et al., 1998). (iv) Analysis of p53 mutations in human lung, breast, and kidney tumors revealed a substantial occurrence of GC to TA mutations, a mutation type produced by unrepaired 8-oxoG (Hollstein et al., 1996; Hernandez-Boussard, et al., 1999).

Since preventive measures which reduce the risk of developing cancer, such as, but not limited to, the use of antioxidants, diet, avoiding cigarette smoking, refraining from occupational exposure to cancer causing agents, are known and further since periodic testing and therefore early detection of cancer offers improved cure rates, there is a great need for, and it would be highly advantageous to have methods and kits for determining a risk of a subject to develop cancer.

Since the effectiveness of cancer therapy depends on the sensitivity of cells to genotoxic (mutageic) agents, there is a great need for, and it would be highly advantageous to have methods and kits for evaluating an effectiveness and preferred dosage of cancer therapy administered to a cancer patient.

There is also a great need for, and it would be highly advantageous to have methods and kits for determining a presence of correlation or non-correlation between an activity of at least one DNA repair enzyme and at least one cancer, so as to allow to determine a risk of a subject to develop cancer and to evaluate an effectiveness and preferred dosage of cancer therapy administered to a cancer patient.

SUMMARY OF THE INVENTION

According to one aspect of the present invention there is provided method of determining a risk (e.g., odds ratio, relative risk) of a subject to develop cancer, the method comprising determining a level of a parameter indicative of a level of activity of a DNA repair/damage preventing enzyme in a tissue of the subject, and, according to the level, determining the risk of the subject to develop the cancer.

According to another aspect of the present invention there is provided a method of determining a risk of a subject to develop cancer, the method comprising determining (a) a presence or absence of exposure to environmental conditions, such as smoking and occupational exposure to smoke or ionizing radiation, associated with increased risk of developing cancer; and (b) a level of a parameter indicative of a level of activity of a DNA repair/damage preventing enzyme in a tissue of the subject; and according to the presence or absence and the level, determining the risk of the subject to develop the cancer.

According to still another aspect of the present invention there is provided a method of determining a presence of correlation or non-correlation between an activity of at least one DNA repair/damage preventing enzyme and at least one cancer, the method comprising determining a level of a parameter indicative of a level of activity of at least one DNA repair/damage preventing enzyme in tissue derived from a plurality of cancer patients and a plurality of apparently normal individuals, and, according to the level determining the correlation or non-correlation between the activity of the at least one DNA repair/damage preventing enzyme and the at least one cancer.

According to further features in preferred embodiments of the invention described below, the parameter is selected from the group consisting of a protein level of said DNA repair/damage preventing enzyme, a level of a RNA encoding said DNA repair/damage preventing enzyme and a level of catalytic activity of said DNA repair/damage preventing enzyme.

According to still further features in the described preferred embodiments the cancer is selected from the group consisting of lung cancer, blood cancers, colorectal cancer, breast cancer, prostate cancer, ovary cancer and head and neck cancer.

According to still further features in the described preferred embodiments the tissue is selected from the group consisting of blood cells, scraped cells and biopsies.

According to still further features in the described preferred embodiments the DNA repair/damage preventing enzyme is selected from the group consisting of a DNA N-glycosylase, deoxyribose phosphate lyase and AP endonuclease.

According to still further features in the described preferred embodiments the DNA N-glycosylase is selected from the group consisting of Uracil DNA glycosylase, hSMUG1, hMBD4, Mismatch-specific thymine/uracil glycosylase, Methylpurine DNA glycosylase, hNTH1, Adenine-specific mismatch DNA glycosylase and 8-oxoguanine DNA glycosylase.

According to still further features in the described preferred embodiments the risk is expressed as a fold risk increase as is compared to a normal, apparently healthy, population, or a reference control group.

According to still further features in the described preferred embodiments the risk is expressed in enzyme specific activity units.

According to still further features in the described preferred embodiments the risk is expressed as a magnitude of a scale.

According to still further features in the described preferred embodiments determining the level of catalytic activity of the DNA repair/damage preventing enzyme is effected using a DNA substrate having at least one lesion therein.

According to still further features in the described preferred embodiments the at least one lesion is at a predetermined site in the DNA substrate.

According to still further features in the described preferred embodiments the lesion is selected from the group consisting of uracil, 5-fluorouracil, 5-hydroxyuracil, isodialuric acid, alloxan, uracil or thymine in U/TpG:5meCpG, uracil (U:G), 3,$N^4$-ethenocytosine, (eC:G), T (T:G), 3-methyladenine, 7-methyladenine, 3-methylguanine, 7-methylguanine, hypoxanthine, 1, N6-ethenoadenine, 1,N2-ethenoguanine, thymine glycol, cytosine glycol, dihydrouracil, formamidopyrimidine urea, adenine from A:G; A:8-oxoG; C:A, 2-hydroxyadenine, 2,5-amino-5-formamidopyrimidine, 7,8-dihydro-8-oxoguanine (also termed 8-oxoguanine) and abasic site.

According to still further features in the described preferred embodiments the substrate includes at least two different lesions of at least two types.

According to still further features in the described preferred embodiments the substrate includes a single lesion.

According to still further features in the described preferred embodiments the substrate includes at least two different lesions of a single type.

According to still further features in the described preferred embodiments the subject is known to be, or is about to be, exposed to environmental conditions associated with increased risk of developing cancer.

According to yet another aspect of the present invention there is provided a method of predicting the efficacy of a mutagenic anti-cancer treatment, such as chemotherapy and/or radiotherapy, in a subject, the method comprising determining a level of a factor indicative of a level of activity of a DNA repair/damage preventing enzyme in a tissue of the subject, and, according to the level, predicting the efficacy of the mutagenic anti-cancer treatment in the subject.

According to still another aspect of the present invention there is provided a method of selecting dosage of a mutagenic anti-cancer treatment, such as chemotherapy and/or radiotherapy, for treating a subject, the method comprising determining a level of a factor indicative of a level of activity of a DNA repair/damage preventing enzyme in a tissue of the subject, and, according to the level, selecting dosage of the mutagenic anti-cancer treatment for treating the subject.

According to an additional aspect of the present invention there is provided a kit for determining a level of activity of a DNA repair/damage preventing enzyme in a tissue of a subject, the kit comprising, a package including, contained in sealable containers, a DNA substrate having at least one lesion therein and a reaction buffer.

According to further features in preferred embodiments of the invention described below, the kit, further comprising test tubes for separating lymphocytes.

According to still further features in the described preferred embodiments the test tubes are prepackaged with an anti-coagulant.

According to still further features in the described preferred embodiments the kit further comprising a liquid having a specific gravity selected effective in separating lymphocytes from red blood cells via centrifugation.

According to still further features in the described preferred embodiments the kit further comprising a solution having osmolarity selected effective in lysing red blood cells.

According to still further features in the described preferred embodiments the kit further comprising a protein extraction buffer.

According to still further features in the described preferred embodiments the kit further comprising reagents for conducting protein determinations.

According to still further features in the described preferred embodiments the kit further comprising a purified DNA repair/damage preventing enzyme, which serves as a control for such activity.

The present invention successfully addresses the shortcomings of the presently known configurations by providing, methods, kits and reagents useful in determining a risk of a subject to develop cancer and for evaluating an effectiveness and individual dosage of cancer therapy administered to a cancer patient.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1b shows a phosphorimage of the reaction products fractionated by urea-PAGE, and FIG. 1c shows the quantification of the images. GO, the DNA substrate with a site-specific 8-oxoG; G, a control substrate with a G instead of 8-oxoG.

FIG. 2a shows a phosphorimage of the reaction products fractionated by urea-PAGE, and FIG. 2b shows the quantification of the images. GO, the DNA substrate with a site-specific 8-oxoG; G, a control substrate with a G instead of 8-oxoG.

FIG. 3a shows a phosphorimage of the reaction products fractionated by urea-PAGE, and FIG. 3b shows the quantification of the images. The protein extract was from a healthy donor Hx, G and GO represent unlabeled competing DNAs, which were similar to the radiolabeled substrate, and contained either hypoxanthine, guanine or 8-oxoG in the same location.

FIGS. 8a-d show OGGA in apparently healthy individuals and in patients with breast cancer or chronic lymphocytic leukemia (CLL). FIG. 8a—OGGA distribution of a control group of 70 healthy female individuals (see FIG. 5), and of 31 breast cancer patients (FIG. 8b). FIG. 8c—OGGA distribution in the control group of 123 subjects, and 19 CLL patients (FIG. 8d).

FIGS. 9a-b show OGGA in apparently healthy individuals and in patients with lung cancer (NSCLC). FIG. 9a—OGGA distribution of the control group of 123 healthy individuals (see FIG. 4), and of 102 lung cancer (NSCLC) patients (FIG. 9b).

FIGS. 10a-b show OGGA in apparently healthy individuals and in lymphoma patients. FIG. 10a—OGGA distribution of the control group of 123 healthy individuals (see FIG. 4), and of 18 lymphoma patients (FIG. 10b).

FIG. 11a—OGGA distribution of the control group of 123 healthy individuals (see FIG. 4), and of 16 colorectal cancer patients (FIG. 11b).

DESCRIPTION OF THE PREFERRED EMBODIMENTS

Figure 1A:
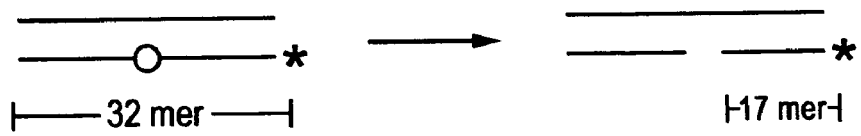
FIG. 1a shows an outline of an OGGA nicking assay according to the present invention. In the assay a 32 base pair synthetic DNA is cleaved at an 8-oxoG lesion (indicated by a circle), generating, after denaturation, a radiolabeled 17-mer. The asterisk represents a radiolabeled phosphate group.
Figure 1B:
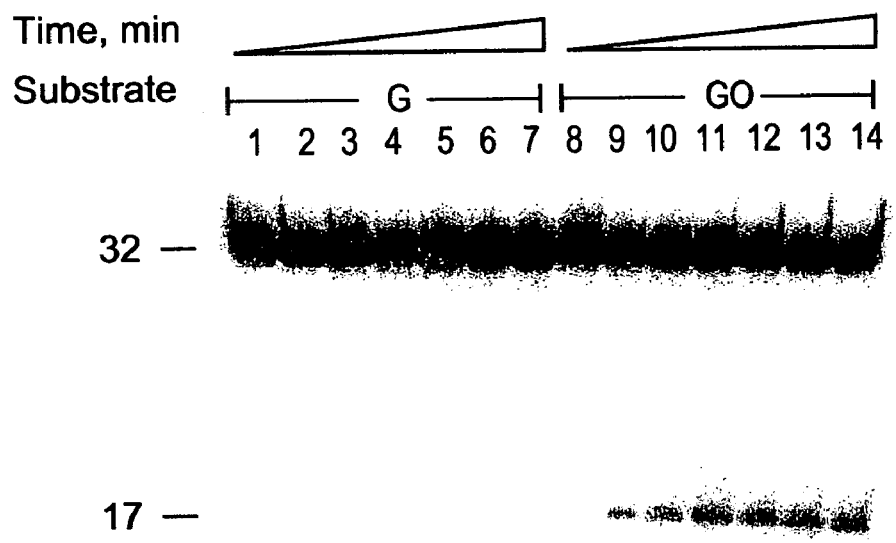
FIGS. 1b-c represent a time course of the OGGA nicking assay of the present invention, performed under standard conditions, with a protein extract prepared from peripheral blood lymphocytes from a healthy donor.
Figure 1C:
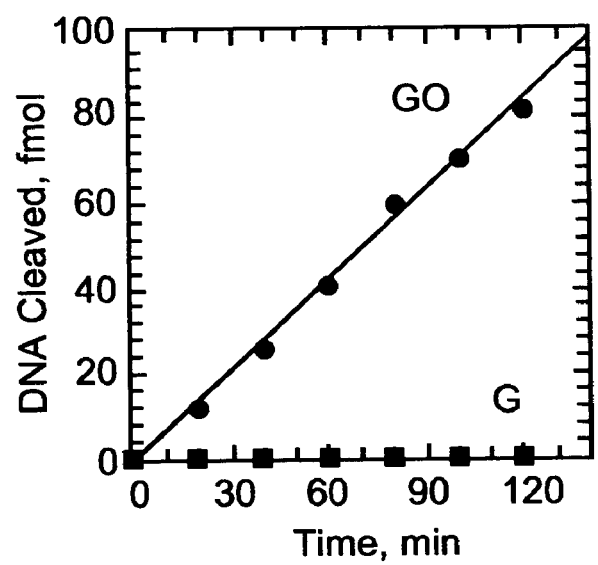
Figure 2A:
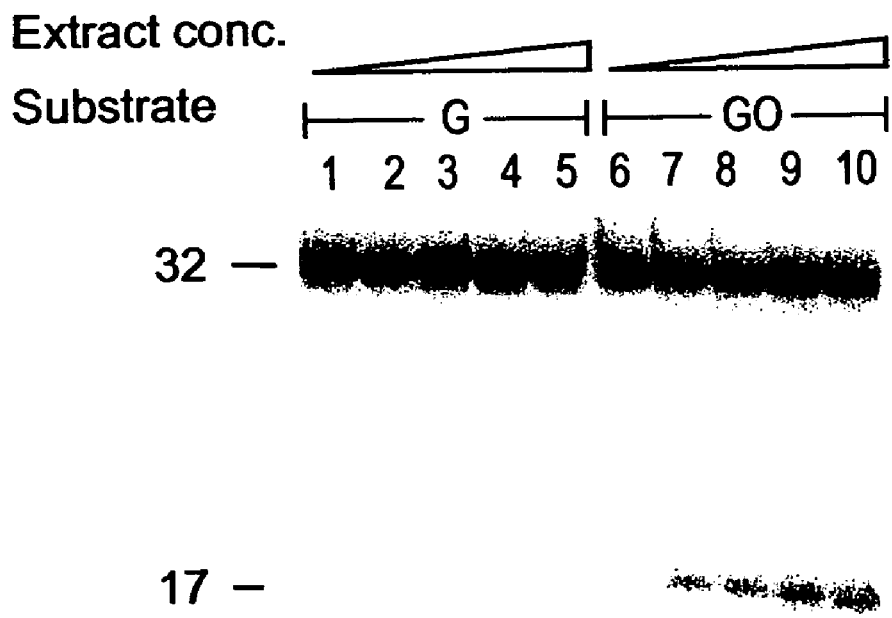
FIGS. 2a-b show protein titration in the OGGA nicking assay. The assay was performed under standard conditions, with the indicated amounts of protein extract prepared from peripheral blood lymphocytes from a healthy donor.
Figure 2B:
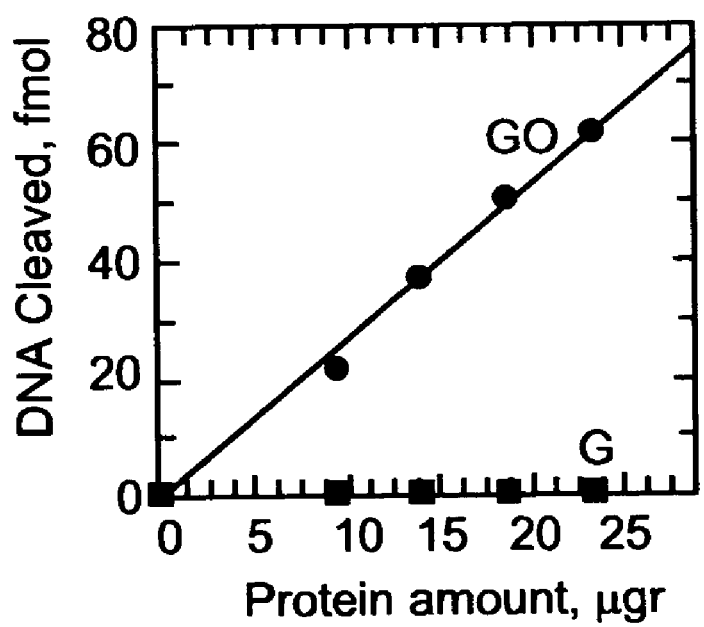

The present invention is of methods and kits which can be used for (i) determining a risk (e.g., odds ratio, reklative risk) of a subject to develop cancer; (ii) evaluating an effectiveness and dosage of cancer therapy administered to a cancer patient; and (iii) determining a presence of correlation or non-correlation between an activity of at least one DNA repair/damage preventing enzyme and at least one cancer.

The principles and operation of a method and kit according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

While conceiving the present invention it was hypothesized that inter-individual variations in DNA repair/damage preventing activity modulate susceptibility of developing cancer.

While reducing the present invention to practice an experimental system which is easily adaptable to clinical use was developed, such that a defined DNA repair activity can now be used in determining cancer risk, and be utilized as a tool in cancer prevention, early detection and prognosis. Since the repertoire of DNA lesions is very large, at present experimental focus was given to an abundant and mutagenic DNA lesion, 8-oxoguanine (also termed 7,8-dihydro 8-oxoguanine or 8-hydroxyguanine; dubbed 8-oxoG). However, other mutagenic DNA lesions, such as, but not limited to, those listed in Table 3 below, can be similarly used to implement the methods of the invention, following suitable adaptation.

Thus, while reducing the present invention to practice, whether inter-individual variations in the activity of OGG, correlate with increased susceptibility to several types of cancers was studied. A lower repair activity might lead to an increased load of DNA lesions, and therefore to increased mutation rate, and earlier occurrence of cancer. Similarly, a lower repair activity renders cancer cells more susceptible to cancer therapy, which is genotoxic by nature. It should be noted that different types of DNA repair may be critical in different types of cancer. The present invention is exemplified, in a non-limiting fashion, with respect to the removal from DNA of a specific type of mutagenic lesion, 8-oxoG, by the activities of one or more DNA N-glycosylase repair enzymes, present in protein extracts from peripheral blood lymphocytes.

The present invention is herein exemplified with respect to the use of the level of the DNA repair enzymatic activity of DNA N-glycosylase(s) directed toward 7,8 dihydroxy 8-oxoguanine (8-oxoguanine DNA N-glycosylase activity; OGG), as a risk factor for lung cancer, lymphomas, and colorectal cancer. The enzymatic activity is measured in a protein extract extracted from peripheral blood lymphocytes and is referred to herein interchangeably as the OGGA nicking assay, OGGA assay or OGGA test.

Using the OGGA test, a case-control study was conducted on 309 individuals: 123 healthy individuals, and a total of 186 cancer patients as follows: 102 lung cancer (NSCLC) patients, 31 breast cancer patients, 18 lymphoma patients, 19 CLL patients, and 16 colorectal cancer patients. The following results were found.

The mean OGGA in healthy individuals of ages <50 ($7.6\pm0.9$; N=34) was slightly higher than in healthy individuals of ages ?50 ($7.0\pm1.0$; N=89). The difference is statistically significant (P=0.02).

The mean OGGA in healthy men ($7.3\pm1.0$; N=53) was similar to healthy women ($7.1\pm1.0$; N=70), the difference was not statistically significant (P=0.36).

The mean OGGA in smokers ($7.3\pm1.00$; N=35) was similar to that of non-smokers ($7.1\pm1.0$; N=88; P=0.46), indicating that the smoking status had a negligible effect on OGGA.

The mean OGGA in lung cancer patients ($6.0\pm1.5$; N=102) was significantly lower than in healthy individuals ($7.2\pm1.0$; N=123), with P=0.0001.

A strong association was found between low OGGA and lung cancer with odds ratio varying from 3.9 (95% CI 1.7-8.6, P=0.0009), to 9.0 (95% CI 3.2-25.0, P=0.0001), depending on the definition of the cutoff level ($\leq7.3$ and $\leq5.6$, respectively). This indicates that a low OGGA value is a risk factor in lung cancer.

The mean OGGA in lymphoma patients ($6.2\pm1.8$; N=18) was significantly lower than in healthy individuals ($7.2\pm1.0$; N=123), with P=0.0001.

Low repair is defined as OGGA value ?5.5 units/µg protein, representing <4% of the healthy individuals. Normal repair is defined as OGGA>5.5 units/µg protein. After adjustment for age, lymphoma patients were 15 times more likely than the healthy controls to have a low OGGA value (Odds Ratio 15.2; 95% confidence interval, 3.7-62.5). This provides evidence that a low OGGA value is a risk factor in lymphoma.

The data shows that OGGA was low in 2 out of 16 (12%) colorectal cancer patients (compared to 5/123 i.e., 4.1% among healthy individuals), indicating that low OGGA is a risk factor in colorectal cancer.

OGGA distribution was normal in breast cancer patients, indicating that OGGA is not a risk factor in this type of cancer.

It will be appreciated that the OGGA and similar tests for other DNA repair activities can be used for screening individuals for purposes of prevention, early diagnosis and prognosis of cancers. These uses will be described in more detail below.

The following provides examples:

(i) Screening for smokers who have low OGGA in order to prevent lung cancer.

Although 85% of lung cancer patients are smokers, the great majority of smokers deal well with carcinogenic effects of smoking, and does not develop lung cancer. Even among heavy smokers, approximately 90% do not develop the disease (Mattson et al, 1987; Minna et al, 2002). The results presented herein clarifies the fact that the combination of smoking and low OGGA causes a dramatic increase in susceptibility to lung cancer. For example, the estimated risk of 30-years old smokers, with an OGGA value of 3.0, is 221-fold higher than the reference (30-years old non-smokers with an OGGA value of 7.0). For comparison, the estimated risk of 30-years old non-smokers, with an OGGA value of 3.0 is only 12-fold higher than the reference. The simplest explanation for this finding is that smokers with Low OGGA in peripheral blood lymphocytes have a lower OGGA also in their lungs. Having a low repair to start with, smoking causes further overloading of DNA damage, therefore leading to a high cancer risk. This is a classical example in which the risk of developing cancer is a combination of genetic factors (level of DNA repair) and external factors (cigarette smoking). Such individuals may be persuaded to quit smoking. Such a screen will be effective as a preventive means against lung cancer, and will lead eventually to a decrease in the incidence of lung cancer.

(ii) Avoiding occupational hazard.

A considerable amount of people work in places which deal with radiation or with smoke. These include radiology departments in hospitals, nuclear industry, nuclear reactors, army personal dealing with nuclear weapons, etc. These people can be tested for OGGA, as a mandatory test, for their own safety. Individuals with Low OGGA might have an increased probability of developing cancer in such places, since ionizing radiation and smoke each produce 8-oxoG. Such individuals will be advised to seek an alternative working environment.

(iii) Using the OGGA value as a prognostic marker for cancer therapy.

Cancer therapy relies heavily on chemicals and radiation. These agents act, in most cases, by inflicting massive DNA damage, which leads to selective killing of the rapidly dividing cancer cells. The problem with such therapeutic agents is that they damage, or kill, also non-cancer cells. Knowing the level of OGGA in a cancer patient, may be used as a marker to estimate the prognosis of a particular therapeutic treatment.

(iv) Screening for susceptibility to lymphoma or colorectal cancers.

OGGA can be used to screen individuals for susceptibility to lymphomas or colorectal cancer.

(v) Early detection of cancer.

Individuals with low OGGA (e.g., smokers with low OGGA who would not quit smoking) can be advised to undergo periodical follow-ups, in order to enable early detection of lung cancer.

Thus, according to one aspect of the present invention there is provided a method of determining a risk of a subject to develop cancer. The method according to this aspect of the present invention is effected by determining a level of a factor indicative of a level of activity of a DNA repair/damage preventing enzyme in a tissue of the subject, and, according to the level, determining the risk of the subject to develop the cancer.

As used herein throughout the term "indicative of" includes correlating to.

According to another aspect of the present invention there is provided a method of determining a risk of a subject to develop cancer. The method according to this aspect of the present invention is effected by determining a presence or absence of exposure to environmental conditions, such as smoking and occupational exposure to smoke or ionizing radiation, associated with increased risk of developing cancer; and determining a level of a factor indicative of a level of activity of a DNA repair/damage preventing enzyme in a tissue of the subject; and according to the presence or absence and the level, determining the risk of the subject to develop the cancer.

Anyone of several approaches may be exploited according to the present invention in determining a level of a factor indicative of a level of activity of a DNA repair/damage preventing enzyme in a tissue of the subject.

According to one embodiment a protein level of the DNA repair/damage preventing enzyme is determined, which is indicative of the level of activity of the DNA repair/damage preventing enzyme. Several alternative quantitative assays are available for determining protein levels. Each of which is based on the specific interactions between proteins and antibodies specific thereto. Table 1 below lists known antibodies recognizing different DNA repair/damage preventing enzyme.

tions, Palo Alto, Calif., Washington Biotechnology Inc., Baltimore, Md.; TNB Laboratories Inc., St. John's, Newfoundland, Canada; and Genemed Synthesis Inc., South San Francisco, Calif.

Such antibodies can be used in a variety of well known antibody based detection assays, including, but not limited to, Western blot, ELISA, a protein chip assay and an antibody chip assay.

In Western blot, total protein preparation is electrophoresed typically under denaturing and optionally under reducing conditions through a gel, typically a polyacrylamide gel. Then, the proteins are blotted onto a membrane, which is thereafter blocked by a non-specific protein, such as milk proteins. An antibody specific to the protein of interest is then interacted with the blot. The antibody will quantitatively bind to the protein of interest. The binding between the antibody and the protein of interest can be monitored by either directly labeling the antibody, or, preferably using a labeled secondary antibody capable of recognizing the first.

In ELISA the antibody capable of binding the protein of interest is linked to an enzyme capable of catalyzing a colorimetric reaction, which serves for quantitative detection.

In a protein chip assay, the protein of interest, typically a plurality of different proteins of interest, are linked to a solid support in addressable positions, so as to form a matrix of proteins. An antibody or several antibodies specific to certain proteins, each being labeled by a distinguishable label, are interacted with the support in the presence of proteins derived from a biological sample. A protein recognized by an antibody and which is present in the biological sample will compete with its solid support bound counterpart, such that the level of binding of the antibody to the respective addressable location on the support, is determinable by such competition for binding.

TABLE 1

| Enzyme | Antibody | Source/Reference |
| --- | --- | --- |
| 1. Uracil DNA glycosylase (UNG) | PU101 | Slupphaug et al., 1995[1] |
| 2. 8-oxoguanine glycosylase (OGG1) | AB1a331 | Monden et al., 1999[2] |
|  | Anti-human OGG1 | Alexis Biochemicals |
| 3. Adenine mismatch glycosylase (MYH) | Anti-hMYH α 344 | Parker et al., 2000[3] |
|  | Anti-hMYH α 516 | Parker et al., 2000[3] |
| 4. 8-oxodGTPase (MTH1) | Anti-M78 | Kang et al., 1995[4] |
| 5. dUTPase (DUT) | DUT415 | Ladner et al., 1997[5] |
| 6. AP endonuclease I (HAP1, APE1, REF1, APEX) | Ref-1 (H-300), Ref-1 (C-20), Ref-1 (N-16), Ref-1 (E-17) | Santa Cruz Biotechnology |
| 7. Deoxyribose phosphate lyase (of DNA polymerase β) | mAb-10S 18S mAb | Srivastava et al., 1995[6] Srivastava et al., 1999[7] |

[1]Slupphaug, G., Eftedal, I., Kavli, B., Bharati, S., Helle, N. M., Haug, T., Levine, D. W., Krokan, H. E. (1995) Properties of a recombinant human uracil-DNA glycosylase from the UNG gene and evidence that UNG encodes the major uracil-DNA glycosylase. Biochemistry 34, 128-138.
[2]Monden, Y., Arai, T., Asano, M., Ohtsuka, E., Aburatani, H., Nishimura, S. (1999) Human MMH (OGG1) type 1a protein is a major enzyme for repair of 8-hydroxyguanine lesions in human cells. Biochem. Biophys. Res. Comm. 258, 605-610.
[3]Parker, A., Gu, Y. and Lu, A. -L. (2000) Purification and characterization of a mammalian homolog of Escherichia coli MutY mismatch repair protein from calf liver mitochondria. Nucleic Acids Res. 28, 3206-3215.
[4]Kang, D., Nishida, J., Iyama, A., Nakabeppu, Y., Furuichi, M., Fujiwara, T., Sekiguchi, M. and Takeshige, K. (1995) Intracellular localization of 8-oxo-dGTPase in human cells, with special reference to the role of the enzyme in mitochondria. J. Biol. Chem. 270, 14659-14665.
[5]Ladner, R. D. and Caradonna, S. J. (1997) The human dUTPase gene encodes both nuclear and mitochondrial isoforms. J. Biol. Chem. 272 19072-19080.
[6]Srivastava, D. K., Rawson, T. Y., Showalter, S. D. and Wilson, S. H. (1995) Phorbol ester abrogates up-regulation of DNA polymerase β by DNA-alkylating agents in Chinese hamster ovary cells. J. Biol. Chem. 270, 16402-16408.
[7]Srivastava, D. K., Husain, I., Arteaga, C. L. and Wilson, S. H. (1999) DNA polymerase β expression differences in selected human tumor cell lines. Carcinogenesis 20, 1049-1054

Antibodies recognizing any specific protein can be readily elicited using methods well known in the art in which cells of an immune system are exposed in vivo or in vitro to at least one epitope of the protein of interest, preferably a plurality of epitopes thereof. Such antibodies can be polyclonal or monoclonal. Commercial antibody developing services are available throughout the world. Examples include: Antibody Solu- In an antibody chip assay, antibodies are linked to a solid support in addressable positions, so as to form a matrix of antibodies each capable of binding a different protein. Proteins derived from a biological sample are labeled and the labeled proteins are interacted with the solid support. The level of binding to the solid support is determined, being indicative of the level of the protein in the sample.

These assays are well known and are well described in the art literature. Further details are available in, for example, "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiugi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Immobilized Cells and Enzymes" IRL Press, (1986); "Methods in Enzymology" Vol. 1-317, Academic Press; Marshak et al., "Strategies for Protein Purification and Characterization—A Laboratory Course Manual" CSHL Press (1996).

According to another embodiment of the present invention the level of a RNA, such as mRNA, encoding the DNA repair/damage preventing enzyme is determined, which is also indicative of the level of activity of the DNA repair/damage preventing enzyme. Several alternative quantitative assays are available for determining RNA levels. Each of which is based on the specific interactions between complementary nucleic acids. Table 2 below lists the human genes encoding DNA repair/damage preventing enzyme.

TABLE 2

| Enzyme | Gene (SEQ ID NO:) | Accession No. | GI No. (NCBI) |
|---|---|---|---|
| 1. Uracil DNA glycosylase | UNG (3) | NM_003362 | 6224978 |
| 2. SMUG1 | SMUG1 (4) | NM_014311 | 7657596 |
| 3. MBD4 | MBD4 (5) | NM_003925 | 4505120 |
| 4. Thymine glycosylase | TDG (6) | NM_003211 | 4507422 |
| 5. Methylpurine glycosylase | MPG (7) | NM_002434 | 4505232 |
| 6. Endonuclease III human homolog | NTH1 (8) | NM_002528 | 6224977 |
| 7. Adenine mismatch glycosylase | MYH (9) | NM_012222 | 6912519 |
| 8. 8-oxoguanine glycosylase | OGG1 (10) | NM_002542 | 7949101 |
| 9. 8-oxodGTPase | MTH1, NUDT1 (11) | NM_002452 | 4505274 |
| 10. dUTPase | DUT (12) | NM_001948 | 4503422 |
| 11. AP endonuclease I | APE1, HAP1. APEX, REF1 (13) | NM_001641 | 4502136 |
| 12. Deoxyribose phosphate lyase (of DNA polymerase β) | POLB (14) | NM_002690 | 4505930 |

Yet undescribed human genes of DNA repair/damage preventing enzyme can nowadays be readily isolated using in-silico searches, since the majority (nearly all) of the coding sequences of the human genome have been cloned and sequenced. Traditional methods of gene isolation can also be exploited as is further described in the list of references provided hereinbelow.

Based on gene sequences, Northern blot, quantitative RNA PCR (also known as quantitative RT-PCR), RNA dot blot and nucleic acid chip assays can be readily developed and used to determine the level of a specific RNA, such as mRNA, in a biological sample. Further details concerning these assays are available in, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "PCR Protocols: A Guide To Methods And Applications", Academic Press, San Diego, Calif. (1990).

In an alternative embodiment, and as is further described in detail below and exemplified by the Examples section that follows, the factor which is determined is the catalytic activity per se of the DNA repair/damage preventing enzyme.

The present invention is useful in determining a risk of a subject to develop cancer, whereby any type of cancer is subject to risk determination by way of implementing the method of the invention. It is well known that all cancers arise from DNA mutations and that the progress of a specific cancer from a primary tumor to a metastatic tumor, reflects clonal selection of cancer cells that accumulate mutations as they develop and turn more cancerous (e.g., proliferate more rapidly, escape proliferation control, acquire autosignalling behavior, induce angiogenesis, etc.) and more metastatic. This process is subject to variations depending on the specific genes involved in the development and progression of different cancers. It is therefore expected that different in vivo DNA repair/damage preventing activities are required to prevent the formation of different cancers. Also, the level of exposure of body tissues to genotoxic agents such as smoke and radiation, differs. Since different types of genotoxic agents cause different types of DNA lesions, it is again expected that different in vivo DNA repair/damage preventing activities are required to prevent the formation of different cancers.

The results obtained while reducing the present invention to practice are in agreement with the above, as low OGGA was found to be associated with some, but not all cancers tested. However, assays similar to the OGGA assay described herein can be readily developed for correlating other cancers with one or more DNA lesions, some of which are listed in Table 3 below.

In effect, all known cancers can be evaluated by finding correlation or non-correlation between the occurrence thereof and the occurrence of low DNA repair/damage preventing activity of certain types. When positive correlation is identified, a predictive risk determination assay can be readily implemented.

Thus, according to an aspect of the present invention there is provided a method of determining a presence of correlation or non-correlation between an activity of at least one DNA repair/damage preventing enzyme and at least one cancer. The method according to this aspect of the invention is effected by determining a level of activity of at least one DNA repair/damage preventing enzyme in tissue derived from a plurality of cancer patients and a plurality of apparently normal individuals, and, according to the level determining the correlation or non-correlation between the activity of the at least one DNA repair/damage preventing enzyme and the at least one cancer. This aspect of the invention is exemplified herein with respect to a single DNA repair enzyme activity (8-oxoguanine DNA glycosylase) using a suitable substrate having a single lesion therein, for a plurality of cancers, for some correlation was found, whereas for other, non-correlation was found.

Thus, the methods of determining a risk of a subject to develop cancer described herein can be implemented for a variety of cancers, including, but not limited to, lung cancers, e.g., small-cells lung cancer and non-small cells lung cancer, blood cancers, e.g., lymphomas and leukemias, including, for example, Hodgkin's lymphoma, non-Hodgkin's lymphoma, acute lymphocytic leukemia, acute myelocytic leukemia, chronic lymphocytic leukemia, chronic myelogenous leukemia and the like, colorectal cancer, breast cancer, prostate cancer, ovary cancer, malignant melanoma, stomach cancer, pancreas cancer, urinary cancer; uterus cancer, bone cancer, liver cancer, thyroid cancer, brain cancer; head and neck cancer, including, for example, salivary carcinoma and laryngeal carcinoma.

DNA repair/damage preventing activity can be measured in extracts of different body tissues or cells, which may be collected from a testee by known methods. Blood cells, scraped cells (e.g., mouth or skin scrapes) and biopsies are good examples as such tissues are routinely removed from subjects for diagnostics.

Several types of DNA repair/damage preventing activities can be assayed according to the present invention, e.g., DNA N-glycosylase, nucleotide pool sanitizing activity (dNTPase activity, e.g., 8-oxodGTPase), AP endonuclease and deoxyribose phosphate lyase (of DNA polymerase β).

An assay for determining the activity of a DNA N-glycosylase is described and exemplified herein with respect to 8-oxoguanine DNA glycosylase. In this respect it is convenient to monitor the nicking activity of DNA N-glycosylase towards DNA substrates including one or more lesion.

An assay for monitoring the activity of 8-oxodGTPase is, for example, as described by Mo et al. [Mo, J. -Y., Maki, H. and Sekiguchi, M. (1992) Proc. Natl. Acad. Sci. USA 89, 11021-11025]. Thus, 8-oxodGTPase activity can be assayed by measuring the hydrolysis of $\alpha$-$^{32}$P-labeled 8-oxodGTP to 8-oxodGMP. The reaction mixture (12.5 µl) contains 20 mM Tris-HCl (pH 8.0), 4 mM MgCl$_2$, 40 mM NaCl, 20 µM $\alpha$-$^{32}$P-labeled 8-oxodGTP, 80 µg/ml bovine serum albumin, 8 mM dithiothreitol, 10% glycerol, and a protein extract. The reaction is executed at 30° C. for 20 minutes. Thereafter, an aliquot (2 µl) from the reaction mixture is spotted onto a PEI-cellulose TLC plate, and the mixture is fractionated with a solution containing 1 M LiCl for 1 hour. The spots on the TLC plate are then visualized and quantified by phosphorimaging. The preparation of 8-oxodGTP is described in Mo et al., ibid.

An assay for monitoring the activity of AP endonuclease is, for example, as described by Wilson III, et al. [Wilson III, D. M., Takeshita, M., Grollman, A. P., Demple B. (1995) Incision activity of human apurinic endonuclease (Ape) at abasic site analogs in DNA. J. Biol. Chem. 270, 16002-16007]. The reaction mixture (10 µl) contains 50 mM Hepes-KOH pH 7.5, 50 mM KCl, 100 µg/ml bovine serum albumin, 10 mM MgCl$_2$, 0.05% Triton X-100, 2 pmol of a the DNA substrate and a protein extract. Reactions are performed at 37° C. for 5-30 minutes, after which the reaction products are fractionated by urea-PAGE, to separate the intact and incised DNA strands. The activity is deduced from the extent of cleavage of the substrate. The preparation of the substrate is described in the same reference (Wilson III et al., ibid.).

An assay for monitoring the activity of deoxyribose phosphate lyase (dRPase) is, for example, as described by Prasad et al. [Prasad, R., Beard, W. A., Strauss, P. R. and Wilson, S. H. (1998) Human DNA polymerase β deoxyribose phosphate lyase. Substrate specificity and catalytic mechanism. J. Biol. Chem. 273, 15263-15270]. Deoxyribose phosphate lyase (dRPase) activity can be assayed by following the removal of deoxyribose phosphate from a $^{32}$P 3' end-labeled duplex oligonucleotide containing a site-specific 5'-incised abasic site. The reaction mixture (10 µl) contains 50 mM Hepes pH 7.4, 2 mM dithiothreitol, 5 mM MgCl$_2$, 20 nM $^{32}$P-labeled duplex oligonucleotide with a site specific abasic site (pre-incised at the 5' with AP endonuclease), and a protein extract. The reaction is carried out at 37° C. for 15 minutes. After the reaction is terminated, the product is stabilized by the addition of NaBH$_4$ to a final concentration of 340 mM, and incubated for 30 minutes at 0° C. The DNA is then ethanol precipitated and fractionated by urea-PAGE. The activity of the dRPase is deduced from the extent of formation of the shorter reaction product. The preparation of the DNA substrate is described in the same reference (Prasad et al., ibid.).

Table 3 below lists examples of DNA repair enzymes, the genes encoding same and the DNA lesion(s) they recognize:

TABLE 3

| Enzyme | Gene | Substrate |
| --- | --- | --- |
| 1. Uracil DNA glycosylase | UNG1,2 | uracil, 5-fluorouracil, 5-hydroxyuracil isodialuric acid, alloxan |
| 2. hSMUG1 | hSMUG1 | uracil |
| 3. hMBD4 | hMBD4 | U or T in U/TpG: 5meCpG |
| 4. Mismatch-specific thymine/uracil glycosylase | TDG | uracil (U:G), 3,N$^4$-ethenocytosine DNA (eC:G), T (T:G) |
| 5. Methylpurine DNA glycosylase | MPG (ANPG, Aag) | 3-methyladenine, 7-methyladenine, 3-methylguanine, 7-methylguanine 8-oxoguanine, hypoxanthine, 1, N6-ethenoadenine, 1,N2-ethenoguanine |
| 6. hNTH1 (human enodonuclease III ehomolog) | hNTH1 | thymine glycol, cytosine glycol, dihydrouracil, formamidopyrimidine urea |
| 7. Adenine-specific mismatch DNA glycosylase (human mutY homolog) | hMYH | A from A:G; A:8-oxoG; C:A 2-hydroxyadenine |
| 8. 8-oxoguanine DNA glycosylase | hOGG1 | 2,5-amino-5-formamidopyrimidine 7,8-dihydro-8-oxoguanine |
| 9. 8-oxo-GTPase/8-oxodGTPase (Human MutT homolog) | hMTH1 (NUDT1) | 8-oxo-GTP, 8-oxo-dGTP |
| 10. dUTPase | hDUT | dUTP |
| 11. AP endonuclease | APE1/APE2 | abasic site |
| 12. Deoxyribose phosphate lyase | POLB | Incised abasic site |

Enzymes 1-8 are DNA glycosylases;
Enzymes 9 and 10 hydrolyze damaged or unnatural dNTPs, thereby preventing their incorporation into DNA during DNA synthesis. Further details concerning mammalian DNA repair genes and activity can be found in Krokan et al. (2000) FEBS Letters 476: 73-77; and Wood et al. (2001) Science 291: 1284-1289, both are incorporated herein by reference.

The risk according to the present invention can be expressed in one of a plurality of ways. In one example the risk is expressed as a fold risk increase in developing cancer as is compared to a normal, apparently healthy, population, or a reference control group. In another example, the risk is expressed in enzyme specific activity units. In another example, a linear or logarithmic risk scale is generated for either the "fold risk increase" or the "activity units" and the risk is expressed as a magnitude of the scale.

According to still further features in the described preferred embodiments determining the level of activity of the DNA repair/damage preventing enzyme is effected using a DNA substrate having at least one lesion therein.

Figure 12A:
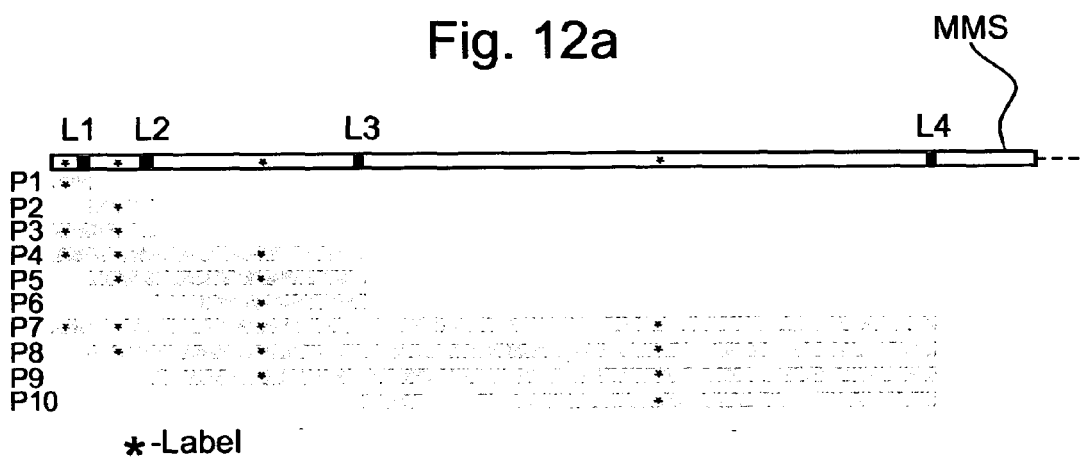
FIGS. 12a-b are schematic representations of monomolecular (FIG. 12a) and plurimolecular (FIG. 12b) universal substrates in accordance with the teachings of the present invention.
Figure 12B:
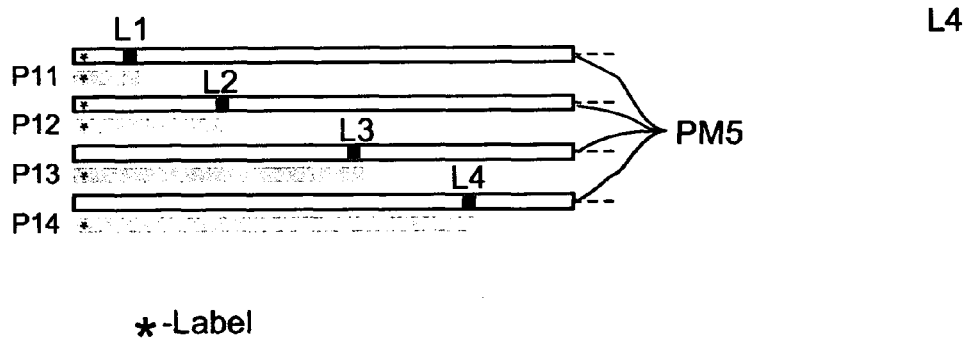

As is schematically exemplified by FIGS. 12a-b, a monomolecular (MMS, FIG. 12a) or plurimolecular (PMS, FIG. 12b) universal substrate can also be generated and used while implementing the methods and kits of the present invention. Such a universal substrate is used according to the present invention to simultaneously determine the activity of more than a single DNA repair/damage preventing enzyme. Thus, a universal substrate of the invention includes at least two (four are shown in FIGS. 12a-b identified by L1-L4) different DNA lesions specifically recognized by at least two different DNA repair enzymes. Careful selection of the positions of the different DNA lesions along the universal substrate, can be used to ensure the generation of distinguishable (e.g., size distinguishable) reaction products (P1-P10 in FIG. 12a, P11-14 in FIG. 12b), being indicative of the activity of the different DNA repair enzymes. In order to ensure accuracy, the lesions are selected to be unique to the activities tested. The length of the universal substrate, especially for a monomolecular substrate, which preferably includes labels along its length, is selected such that reciprocal reaction products are substantially longer than all of the reaction products to be analyzed (P1-P10 in FIG. 12a). End labeling can be used in the case of a plurimolecular substrate to circumvent this problem altogether. Thus, the length of a substrate according to the present invention, without limitation, can range between 10 base pairs and several hundreds base pairs.

A substrate of the invention can thus have at least one lesion of at least one type or at least one lesion of at least two types (universal substrate), the lesions preferably being positioned at predetermined site(s) in the DNA substrate. The lesion(s) can be of any type, including, but not limited to, uracil, 5-fluorouracil, 5-hydroxyuracil, isodialuric acid, alloxan, uracil or thymine in U/TpG:5meCpG, uracil (U:G), 3,$N^4$-ethenocytosine, (eC:G), T (T:G), 3-methyladenine, 7-methyladenine, 3-methylguanine, 7-methylguanine, hypoxanthine, 1, N6-ethenoadenine, 1,N2-ethenoguanine, thymine glycol, cytosine glycol, dihydrouracil, formamidopyrimidine urea, adenine from A:G; A:8-oxoG; C:A, 2-hydroxyadenine, 2,5-amino-5-formamidopyrimidine, 7,8-dihydro-8-oxoguanine and abasic site.

A lesion can be introduced at a unique and defined location (site) in a DNA molecule using solid phase DNA synthesis, using in sequence the four conventional phosphoramidite building blocks used in the synthesis of oligodeoxynucleotides and additional at least one modified phosphoramidite building block, which when introduced into the DNA introduces a lesion therein, which lesion is recognizable by a DNA repair enzyme. In the alternative, a DNA molecule is exposed to a mutagenic agent (e.g., an oxidative agent or UV radiation) which forms one or more lesion of one or more types therein. Even when using this method, one can select a pre-substrate which will result in a product (substrate of the invention) in which the lesions are non-randomly distributed, since the extent by which a specific lesion is formed in DNA is often dependent on the DNA sequence.

Other alternatives also exist. For example, one can oxidize a plasmid DNA with an oxidizing agent. This will form several lesions in the plasmid DNA. One can now use this plasmid DNA to assay a repair enzyme that acts on this DNA, without knowing precisely where the lesions are. The enzyme will produce a nick in the DNA, and this will convert the plasmid from the supercoiled closed form to the nicked (open circular) form. These two can be easily distinguished by gel electrophoresis or gradient centrifugation. In another example a piece of DNA is enzymatically synthesized in the presence of lesioned building blocks. Other alternatives are also known, such as chemical deamination, etc.

Thus, the substrate of the present invention can include at least two different lesions of at least two types, a single lesion, or at least two different lesions of a single type.

A cancer risk determination test according to the present invention is specifically advantageous for a subject which is known to be, or is about to be, exposed to environmental conditions associated with increased risk of developing cancer, such as smoking and occupational exposure to smoke, ionizing radiation and other carcinogens.

As is discussed hereinabove, the effectiveness of cancer therapy is due to its genotoxic effect affecting cancer cells more than normal cells. Thus, according to another aspect of the present invention there is provided a method of predicting the efficacy of a mutagenic anti-cancer treatment, such as chemotherapy and/or radiotherapy, in a subject. The method according to this aspect of the invention is effected by determining a level of activity of a DNA repair enzyme in a tissue of the subject, and, according to the level, predicting the efficacy of the mutagenic anti-cancer treatment in the subject.

Anti cancer therapy dosage can also be individually optimized in view of the teachings of the present invention. Thus, according to still another aspect of the present invention there is provided a method of selecting dosage of a mutagenic anti-cancer treatment, such as chemotherapy and/or radiotherapy, for treating a subject. The method according to this aspect of the invention is effected by determining a level of activity of a DNA repair/damage preventing enzyme in a tissue of the subject, and, according to the level, selecting dosage of the mutagenic anti-cancer treatment for treating the subject. In this case, the tissue is preferably a biopsy derived from the cancer itself.

According to an additional aspect of the present invention there is provided a kit for determining a level of activity of a DNA repair/damage preventing enzyme in a tissue of a subject. In its minimal configuration, the kit includes, a package including, contained in sealable containers, a DNA substrate having at least one lesion therein and a reaction buffer selected suitable for supporting DNA repair activity. Preferably, the kit also includes test tubes for separating lymphocytes. Preferably, the test tubes are prepackaged with an anticoagulant, such as, but not limited to, heparin. Still preferably, the kit further includes a liquid having a specific gravity selected effective in separating lymphocytes from red blood cells via centrifugation, e.g., Ficoll contained in lymphocytes isolation tubes. Advantageously, the kit includes a solution having osmolarity selected effective in lysing red blood cells. In a preferred embodiment of the invention a protein extraction buffer is also included in the kit. Preferably, the kit further includes reagents for conducting protein determinations, e.g., reagents included in the BCA kit by Pierce. Still preferably, the kit includes a purified DNA repair enzyme, which serves as a control for such activity.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Materials and Experimental Methods

DNA substrates: The DNA substrate was prepared by annealing two complementary synthetic oligonucleotides, 32-bases long each. They were synthesized by the Synthesis Unit of the Biological Services Department at the Weizmann Institute of Science. The oligonucleotide containing 8-oxoG had the sequence 5'-CCGGTGCATGACACTGTOACC TATCCTCAGCG-3' (SEQ ID NO:1) (O=8-oxoG). The 8-oxoG phosphoramidite building block was purchased from Glen Research. The oligonucleotide was $^{32}$P-labeled using T4 polynucleotide kinase, and annealed to the oligonucleotide 5'-CGCTGAGGATAGGTCACAGTGTCATGCA CCGG-3' (SEQ ID NO:2). The radiolabeled duplex was purified by PAGE on a native 10% gel. Its concentration was determined by the PicoGreen dsDNA quantitation assay (Molecular Probes).

Blood samples: Large blood samples were obtained from the blood bank in the Sheba Medical Center. Samples of 10 ml peripheral blood were obtained from healthy donors or from cancer patients. Those were collected after obtaining permission from the Institutional Helsinki Committee.

Isolation of peripheral lymphocytes: The blood samples were processed 18-24 hours after collection. A 100 μl aliquot from each sample of whole blood was analyzed using a Cobas Micros (Roche Diagnostic System) blood counter. Ten ml PBS (Dulbecco's phosphate buffered saline, Sigma) were added to the remaining blood portion, and peripheral blood lymphocytes were isolated by density gradient centrifugation of the diluted whole blood on a polysucrose-sodium metrizoate medium in UNI-SEP tube (NOVAmed, Jerusalem, Israel). Centrifugation was performed at 1,000×g for 30 minutes at 20° C.

Following centrifugation the lymphocyte band was removed and washed with PBS buffer. Elimination of red blood cells was done by lysis in 5 ml of 155 mM NH$_4$Cl; 0.01 M KHCO$_3$; 0.1 mM EDTA for 4 minutes at room-temperature. The lymphocytes were washed with PBS, and suspended in 1 ml PBS. The number of white blood cells in this suspension was determined using a Cobas Micros (Roche Diagnostic System) blood counter.

Samples containing 1-4×10$^6$ cells were precipitated by centrifugation at 5,000 rpm, for 4 minutes at room temperature. The cells pellet was then resuspended to a concentration of 20,000 cells/μl in 50 mM Tris.HCl (pH 7.1), 1 mM EDTA, 0.5 mM DTT, 0.5 mM spermidine, 0.5 mM spermine, and a protease inhibitor cocktail (Sigma). The cells were incubated on ice for 30 minutes, after which they were frozen in liquid nitrogen. The frozen lymphocytes were stored at −80° C.

Preparation of a protein extract: The frozen lymphocytes were thawed at 30° C., after which their protein content was extracted with 220 mM KCl, for 30 minutes on ice. Cell debris was removed by centrifugation at 13,200 rpm for 15 minutes at 4° C. Glycerol was added to the protein extract to a final concentration of 10%, and the extract was frozen in liquid nitrogen. Protein concentration was determined by the BCA assay kit (Pierce) using bovine γ-globulin as a standard.

Standard analysis of OGG activity: The reaction mixture (20 μl) contained 50 mM Tris-HCl (pH 7.1), 1 mM EDTA, 115 mM KCl, 20 μg bovine γ-globulin, 2 pmol PolydA.polydT, 0.5 pmol substrate and 8-12 μg protein extract. The reaction was carried out at 37° C. for 30 minutes, after which it was stopped by the addition of 15 mM EDTA, 0.2% SDS. The proteins were degraded by incubation with proteinase K (20 μg) for one hour at 37° C., after which they were treated with 80 mM NaOH for 30 minutes at 37° C. The denatured DNA products were analyzed by electrophoresis on a 15% polyacrylamide gel containing 8 M urea, in 89 mM Tris-borate, 2.5 mM EDTA pH 8.0, at 1,500 V for 2 hours at 45-50° C. The distribution of radiolabeled DNA products was visualized and quantified using a Fuji BAS 2500 phosphorimager. One unit of OGG activity is defined herein to cleave 1 fmol of DNA substrate in 1 hour at 37° C., under the standard reaction conditions described herein. In the following, OGGA is presented as specific activity, i.e., activity units/1 μg of total protein extract.

Statistical analysis: A 3-way ANOVA was employed for healthy subject to compare mean OGGA values, with gender, age (?50, <50), and smoking status as fixed effects.

Student's t-test was used to compare the mean OGGA values, analyzed as a continuous variable, between adenocarcinoma and squamous cell carcinoma patients.

To neutralize possible effects on OGGA means originating from the difference in mean age between the cases and controls, OGGA means were compared using ANCOVA, with age (treated as a continuous variable) as a covariate. This analysis was possible since no significant interaction was found between age and health conditions.

Associations were calculated using Fisher's exact test, and Odds ratios (OR) were calculated from a 2×2 table. Adjusted ORs and CI values were calculated by fitting logistic regression models with adjustment for age, sex and smoking status for lung cancer; and adjustment for age only, for lymphoma. OGGA values were analyzed as a continuous variable or as a dichotomized variable at values corresponding to 4% (OGGA cutoff at 5.5), 5% (OGGA cutoff at 5.6), 10% (OGGA cutoff at 5.9), 15% (OGGA cutoff at 6.2), 25% (OGGA cutoff at 6.4) or 50% (OGGA cutoff at 7.3) of the control group. Age was analyzed as a continuous variable, whereas gender and smoking status were analyzed as dichotomic variables.

Odds Ratio (OR) were calculated by the formula (Kleinbaum, 1994)

$$OR_{X1-X0} = e^{\sum_{i=1}^{k} b_i(X_{1i} - X_{0i})}$$

using the $b_i$ estimates from the logistic regression model where OGGA values were analyzed as a continuous variable ($b_{OGGA}$=0.624; $b_{age}$=0.1; $b_{smoker}$=2.9). For example, $X_0$, the reference, was used to represent non-smoking, 30 years-old individuals with an OGGA value of 7.0, and $X_i$ was used to represent the tested subject group. Thus the formula for the current model is:

$$-0.624(OGGA_i - 7.0) + 0.1(Age_i - 30) + 2.9S_i$$

$$OR_i = e$$

where $OGGA_i$ and $Age_i$ are the OGGA value and age of individual i, and $S_i$ is either 1 or zero, for a smoker or a non smoker, respectively.

All the statistical analyses were performed using SAS software (version 6.12; SAS Institute Inc., Cary, N.C.).

Experimental Results

The OGG activity (OGGA) DNA repair test: Base excision repair (BER) is initiated by a DNA N-glycosylase, that releases the damaged or unusual base from DNA, generating an abasic site. The latter is then repaired by an AP endonuclease (APE/HAP1) and/or the lyase activity of the glycosylase, as well as the deoxyribose phosphate lyase (dRPase) activity of DNA polymerase β. The resulting gap is filled-in by DNA polymerase β, forming a patch of 1-3 nucleotides, followed by ligation (Dianov, et al., 1992, Singhal, et al., 1995). A long patch pathway of BER was identified which requires also PCNA, and the FEN-1 flap endonuclease (Fortini, et al., 1998, Kim, et al., 1998). It was reported that 8-oxoG can be repaired in cell extracts also by nucleotide excision repair (Reardon, et al., 1997), however, the in vivo significance of this finding is not clear (Runger, et al., 1995). In addition, it was reported that there is transcription-coupled repair of 8-oxoG, and that it required the XPG, TFIIH and CSB (Le Page, et al., 2000), and the BRCA1 and BRCA2 proteins (Le Page, et al., 2000).

While reducing the present invention to practice, an assay was developed for OGG activity (the OGGA test), using as substrate a $^{32}P$ end-labeled synthetic oligonucleotide, 32-base pairs long, carrying a site-specific 8-oxoG. The source of the OGG activity was a protein extract prepared from human peripheral blood lymphocytes (PBL), obtained by Ficoll fractionation from 10 ml blood samples. A protein extract was prepared from the lymphocytes by freeze-thaw, followed by salt extraction. The removal of 8-oxoG from the oligonucleotide, by the OGG activity in the extract, generates an abasic site, which was rapidly incised either by the AP lyase activity of the enzyme, or by AP endonucleases present in the extract. Alkali treatment, which breaks abasic sites, was performed after the incubation with the extract in order to ensure complete cleavage of the abasic site, such that only OGG activity is measured in the test. Analysis by urea-PAGE followed by phosphorimaging was used to quantify the extent of nicking, indicated by the formation of a shorter radiolabeled DNA fragment, 17 nucleotides long (FIG. 1a). The OGG activity level (OGGA value) is measured as specific activity, i.e., units of OGG activity/1 µg of protein extract. One unit of OGG activity cleaves 1 fmol of DNA substrate in 1 hour at 37° C., under standard reaction conditions.

Figure 3A:
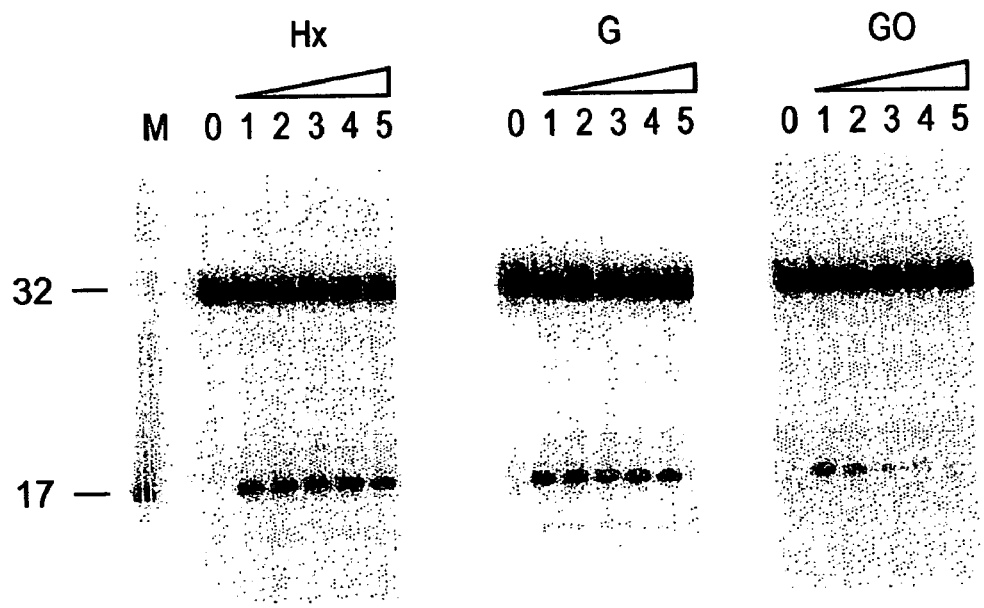
FIGS. 3a-b show analysis of the specificity of the OGGA nicking assay of the present invention. The assay was performed under standard conditions, except that the reaction mixture contained 2 pmol of radiolabeled substrate containing 8-oxoG, and the indicated amounts of unlabeled competing DNA.
Figure 3B:
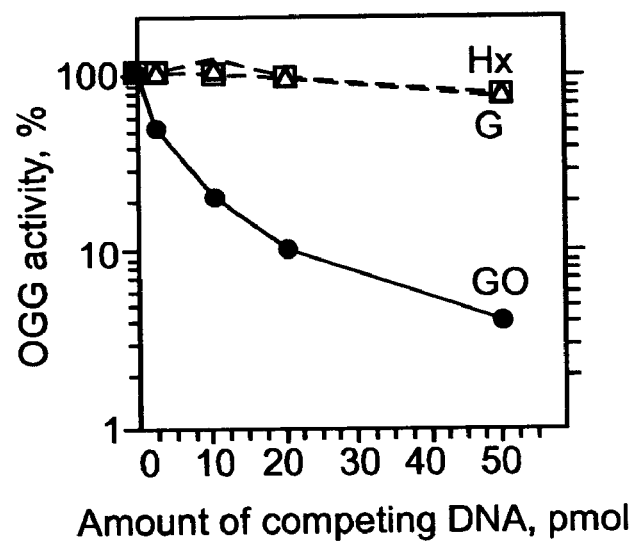

FIGS. 1b-c and 2a-b show a time course and a titration of OGG activity, respectively, in lymphocyte extracts. The activity was dependent on the presence of 8-oxoG in the DNA substrate. No activity was observed when the DNA contained a G instead of the 8-oxoG. This observed activity is mostly due to the OGG1 enzyme, which was shown to be responsible for most of OGG activity in extracts prepared from human cells (Monden, et al., 1999). The existence of OGG2, a second OGG enzyme was reported. However, its activity was much lower than OGG1 in whole cell extracts (Hazra, et al., 1998). In addition to OGG, APNG (alkylpurine DNA N-glycosylase), also termed Aag (alkyladenine DNA glycosylase), or MPG (N-methylpurine glycosylase), was reported to act on 8-oxoG (Bessho, et al., 1993) but this finding was challenged in Hang, et al. (1997). In vivo this protein has no significant role in removing 8-oxoG from DNA, at least in mice (Engelward, et al., 1997, Hang, et al., 1997). In order to establish whether MPG is involved in the removal of 8-oxoG from DNA by lymphocyte extracts, a competition experiment was performed with an unlabeled duplex oligonucleotide containing a site-specific hypoxanthine (a substrate of MPG but not for OGG1; (see, Engelward, et al, 1997, Hang, et al., 1997)). As can be seen in FIG. 3, this duplex oligonucleotide did not inhibit the incision of the 8-oxoG-containing DNA by the extract, suggesting that APNG is not involved in the incision reaction. A control experiment with an excess of unlabeled duplex oligonucleotide containing a G instead of 8-oxoG showed no inhibition, whereas a duplex oligonucleotide containing 8-oxoG-DNA did cause inhibition, as expected (FIGS. 3a-b). These competition experiments are an indication of the specificity of the OGGA test to 8-oxoG.

Reproducibility experiments showed that the assay is accurate and highly reproducible, with a coefficient of variation ?10%. An example of a reproducibility experiment is shown in Table 4.

TABLE 4

Reproducibility of the OGGA test

A Blood Sample:

| 1 | 2 | 3 | 4 | 5 | 6 | 7 | 8 | 9 | 10 | 11 | 12 |
|---|---|---|---|---|---|---|---|---|----|----|----|
| \multicolumn{12}{c}{OGGA (units/µg protein):} |
| 6.8 | 6.9 | 6.4 | 6.5 | 6.7 | 7.4 | 6.9 | 6.5 | 6.6 | 6.7 | 5.9 | 6.9 |

Average OGGA: 6.7
Standard variation: 0.4
Coefficient of variance: 6%

Twelve blood samples from a healthy donor (donor No. 54), 10 ml each, were processed and assayed for OGGA. One unit of OGG activity incises 1 fmol GO-containing substrate in 60 minutes at 37° C. under standard assay conditions.

B Blood Sample:

| 1 | 2 | 3 | 4 | 5 | 6 | Ave | SD | CV |
|---|---|---|---|---|---|-----|-----|-----|
| \multicolumn{9}{c}{OGGA (units/µg protein)} |
| Experiment 1: 6.7 | 7.2 | 6.7 | 6.8 | 7.1 | 6.7 | 6.9 | 0.2 | 3% |
| Experiment 2: 7.9 | 6.9 | 7.8 | 8.2 | 8.1 | 7.8 | 7.8 | 0.5 | 6% |
| Experiment 3: 6.9 | 7.0 | 7.1 | 7.3 | 7.9 | 7.2 | 7.2 | 0.4 | 5% |

Overall average OGGA: 7.1
Standard deviation (SD): 0.5
Coefficient of variance (CV): 7%

Six blood samples from a healthy donor (donor No. 50), 10 ml each, were processed to prepare protein extracts. The table shows the results of three independent assays performed with these assays on three different days.

Figure 4:
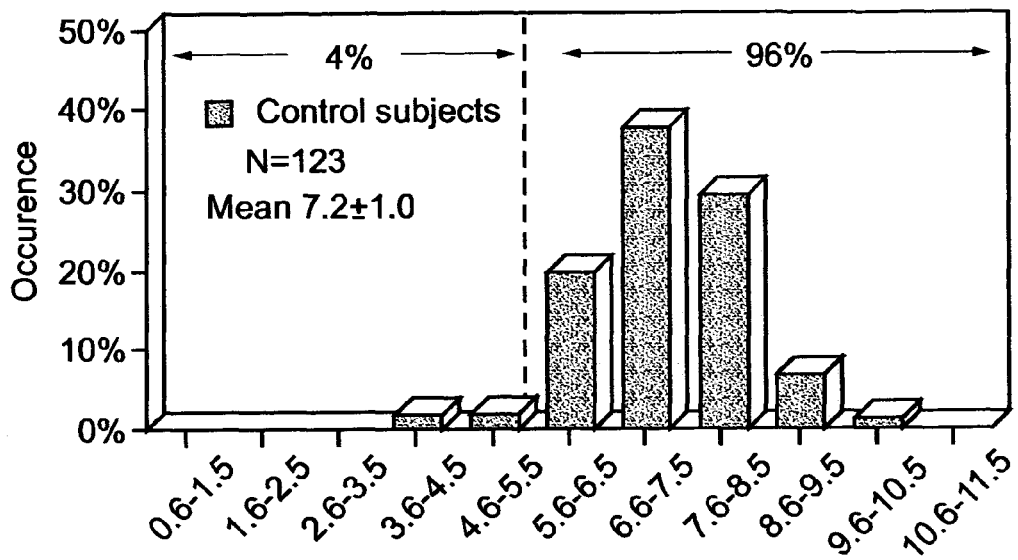
FIG. 4 shows the OGGA distribution in healthy individuals (i.e., control subjects). The OGGA nicking assay of the present invention was performed with blood samples from 123 healthy donors. OGGA≦5.5 is defined as Low (less than 4% of the control group) OGGA>5.5 is defined as Normal.

OGGA value in healthy individuals (control subjects): The OGGA test was performed on blood samples from 123 healthy individuals, and the distribution is shown in FIG. 4. The mean OGGA value was 7.2±1.0 units/µg protein (this will be also dubbed OGGA value of 7.2±1.0; Table 5).

TABLE 5

OGGA values in healthy individuals

| Factor | No. | Mean OGGA ± SD* | P** |
|--------|-----|-----------------|-----|
| All | 123 | 7.2 ± 1.0 | |
| Age, years | | | |
| <50 | 34 | 7.6 ± 0.9 | |
| ≧50 | 89 | 7.0 ± 1.0 | 0.02 |
| Gender | 53 | 7.3 ± 1.0 | |
| Male | 70 | 7.1 ± 1.0 | 0.36 |
| Female | | | |

TABLE 5-continued

OGGA values in healthy individuals

| Factor | No. | Mean OGGA ± SD* | P** |
|---|---|---|---|
| Smoking status | | | |
| Never | 88 | 7.1 ± 1.0 | |
| Current | 35 | 7.3 ± 1.0 | 0.46 |

*SD, standard deviation.
**P values are results of 3-way ANOVA.

The range of OGGA was 3.6-10.1 units/µg protein, representing a 2.8-fold range of OGG activity. This is a rather narrow distribution of activity, significantly narrower than previously reported (Asami, et al, 1996).

Figure 5:
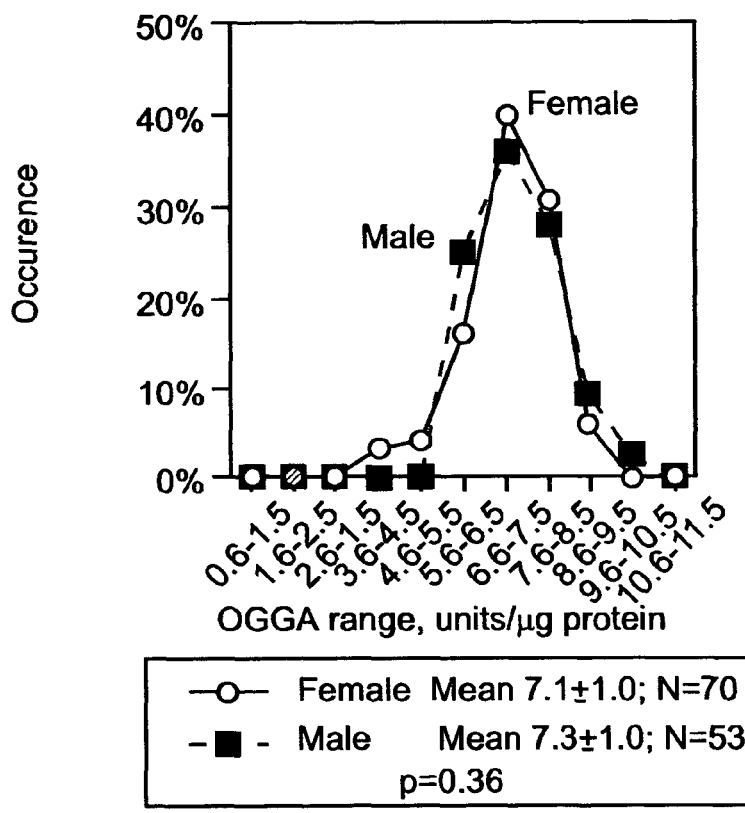
FIG. 5 shows a comparison of OGGA in males and females. The OGGA distribution of the 123 individuals shown in FIG. 4, was plotted separately for males (N=53) and females (N=70).
Figure 6:
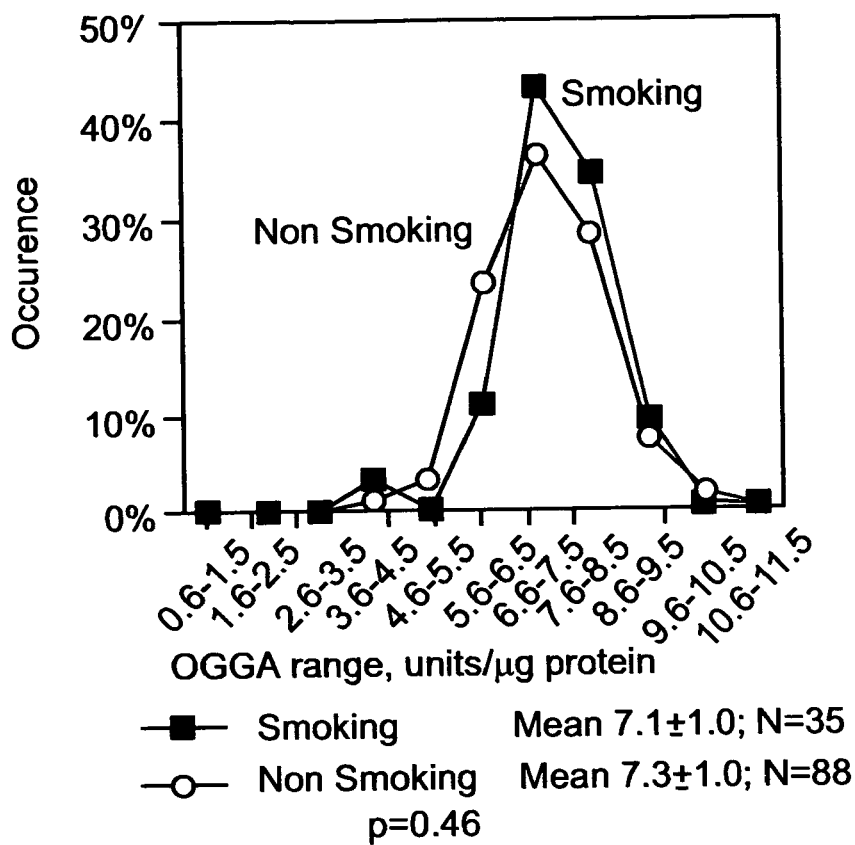
FIG. 6 shows a comparison of OGGA in smokers and non-smokers. The OGGA distribution of the 123 individuals shown in FIG. 4, was plotted separately for smokers (N=35) and non-smokers (N=88).
Figure 7:
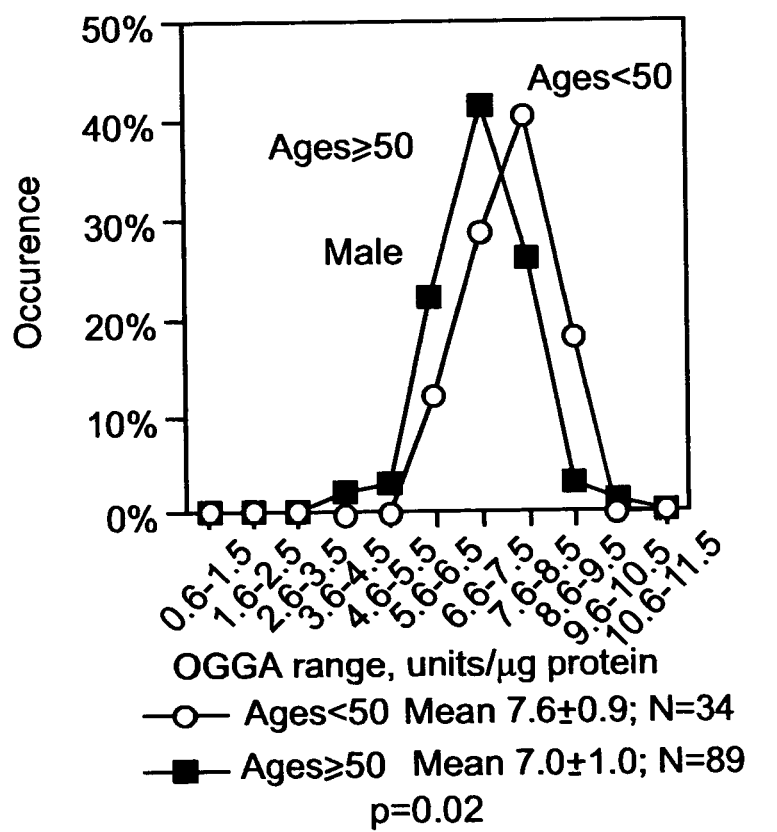
FIG. 7 shows a comparison of OGGA in two age groups. The OGGA distribution of the 123 individuals shown in FIG. 4, was plotted separately for ages <50 (N=34) and ?50 (N=89)

A 3-way ANOVA with gender, age (<50, ?50), and smoking status revealed that there was no significant difference in mean OGGA value between men (53 individuals; 7.3±1.0 units/µg protein) and women (70 individuals; 7.1±1.0 units/µg protein; P=0.36 FIG. 5; Table 5), or between smokers (N=35; 7.3±1.0 units/µg protein) and non-smokers (N=88; 7.1±1.0 units/µg protein; P=0.46). This indicates that smoking does not affect the OGGA value in peripheral blood lymphocytes (FIG. 6; Table 5). This result differs from the result obtained by Asami et al. (1996), who reported that 8-oxoG repair activity was increased 1.6-fold in smokers. In contrast, there was a small (6.6%), but statistically significant decrease in mean OGGA values between the two age groups: Individuals under the age of 50 had a mean OGGA value of (7.6±0.9; N=34), whereas those 50 years or older had a mean OGGA value of (7.0±1.0; N=89; P=0.02; FIG. 7; Table 5). Taken together these results indicate little or no variation of the OGGA value with age, smoking status and gender.

Figures 8C, 8D:
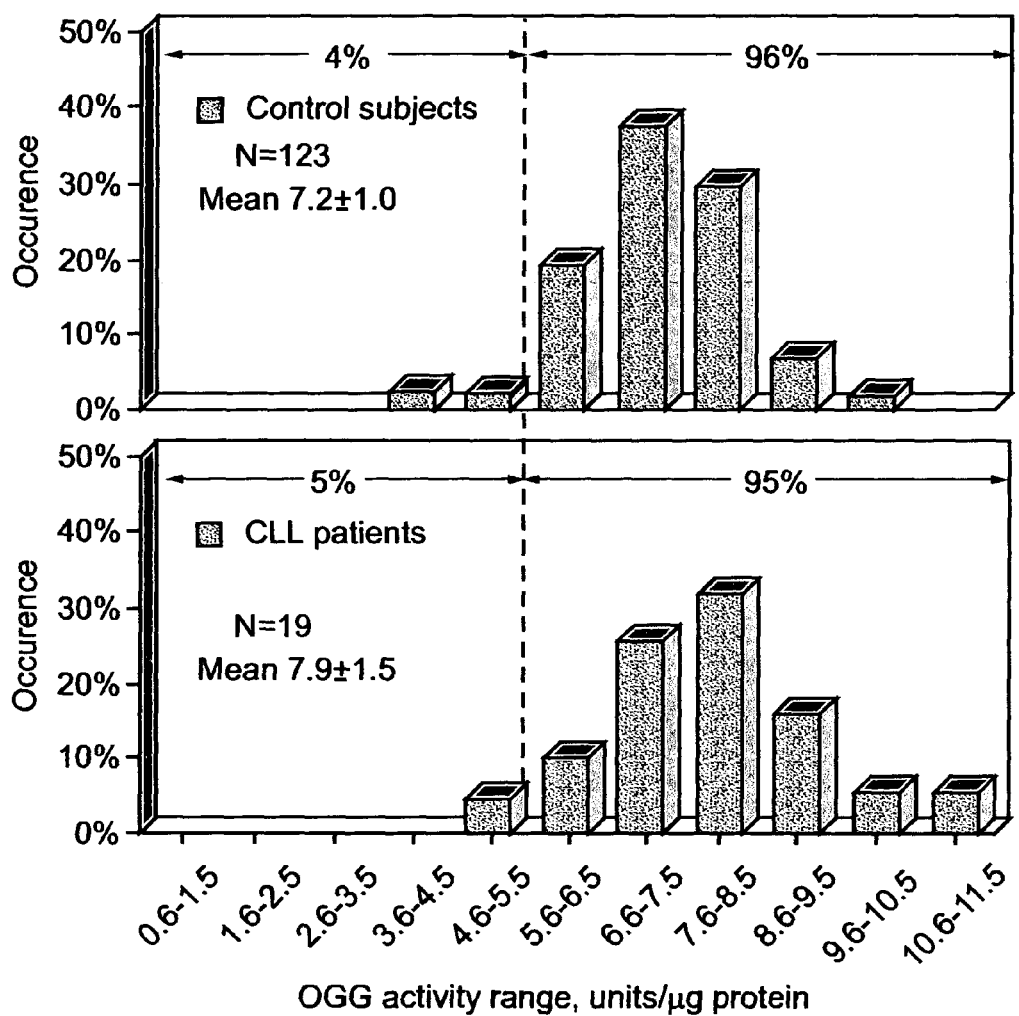

OGGA is not reduced in patients with breast cancer, and is altered in chronic lymphocytic leukemia (CLL): The OGGA test was performed on blood samples from 31 breast cancer patients and 19 CLL patients. As can be seen in Table 6, the mean OGGA value was 7.3±1.4 units/µg protein in breast cancer patients, similar to that of control female subjects (7.1±1.0, P=0.29; Tables 5 and 6). Also, the distribution of OGGA values was similar (FIGS. 8a-d). These results indicate that OGGA is not a risk factor in breast cancer. The mean OGGA value of CLL patients was 7.9±1.5, higher than the control subjects (7.2±1.0, P=0.0007; Table 6). However, the distribution of OGGA values among CLL patients was similar to the control group (FIGS. 8c-d).

TABLE 6

Mean OGGA values in cancer patients

| Healthy/Disease | No. | Mean OGGA ± SD* | P** |
|---|---|---|---|
| Healthy | 123 | 7.2 ± 1.0 | |
| Lung cancer (NSCLC) | 102 | 6.0 ± 1.5 | 0.0001 |
| Breast cancer | 31 | 7.3 ± 1.4 | 0.29 |
| Lymphoma | 18 | 6.2 ± 1.8 | 0.0001 |
| CLL | 19 | 7.9 ± 1.5 | 0.0007 |
| Colorectal cancer | 16 | 7.5 ± 1.8 | 0.047 |

*SD, standard deviation.
**OGGA means were compared using ANCOVA, with age (treated as a continuous variable) as a covariate. For breast cancer patients, the control group consisted of female subjects.

OGGA is a risk factor in lung cancer: The OGGA test was performed with blood samples from 102 patients who suffered from operable non-small cell lung cancer (NSCLC), and had not been subjected to either chemo- or radiotherapy at the time when the blood samples were taken. As can be seen in FIGS. 9a-b and Table 6, the mean OGGA value was 6.0±1.5 units/µg protein, significantly lower than the mean value of controls (7.2±1.0, P=0.0001). Analyzing separately cases with adenocarcinoma or squamous cell carcinoma revealed a similar OGGA level in these two main sub-types of NSCLC: adenocarcinoma: 6.1±1.5, N=37; squamous cell carcinoma: 5.8±1.6 N=35; P=0.44 (the other 30 cases were either other sub-types or unclassified NSCLC). The comparison of the distributions of OGGA in controls and in cases highlights the difference between the two groups. As can be clearly seen in FIGS. 9a-b, there is a shift to lower OGGA values in cases as compared to controls. For example, only 4% of controls have OGGA values of ?5.5, whereas 38% of cases have OGGA values in this range. This includes values 2-3 fold lower than the mean OGGA values of the controls. The mean age of the control group (57±14) was significantly different from the cases group (68±10; P<0.0001). Therefore, logistic regression, adjusted for age, was used to analyze associations, and analysis of covariance was used to compare age-adjusted mean OGGA values.

To analyze the association between levels of OGGA and presence of lung cancer logistic regression was used, where the binary dependent variable was presence/absence of lung cancer, and with age as a continuous variable, and gender, smoking status and OGGA as dichotomic variables. The latter was dichotomized at values corresponding to 5% (OGGA cutoff at 5.6), 10% (OGGA cutoff at 5.9), 15% (OGGA cutoff at 6.2), 25% (OGGA cutoff at 6.4) or 50% (OGGA cutoff at 7.3) of the control group. As can be seen in Table 7, smoking is strongly associated with lung cancer, in agreement with its established role as a major risk factor in the disease. For example, in a model where OGGA was dichotomized at ?5.9 (corresponding to 10% of the controls), the Odds Ratio (OR) for smokers was 20.8 (95% CI 7.8-55.4, P=0.0001). In a model where the OGGA cutoff was defined as ?7.3 (corresponding to 50% of controls), the OR for smokers was 23.0 (95% CI 8.9-59.2, P=0.0001). The gender had no significant effect in any of the models, whereas increased age was associated with the presence of lung cancer. Notice that although the OR for age was relatively small in all models (1.1 95% CI 1.1-1.2, P=0.0001) it is statistically significant. The age was analyzed as a continuous variable, and the relatively small OR is given per one-year change. Therefore, its final effect when applied to a particular change of age might be much larger (see Table 8 below).

As can be seen from Table 7, a clear association was found between the level of OGGA and presence of lung cancer. Moreover, there is a dose-dependent effect, with higher OR obtained for lower OGGA. For example, OR values of 3.9, 5.2, 7.0 and 9.0 were obtained for cutoff OGGA values of 7.3, 6.4, 5.9 and 5.6, respectively (Table 7). These high OR values indicate a strong association between low OGGA and lung cancer. Moreover, the increase in OR with decreasing OGGA further strengthens the significance of the association. In addition, the high OR values argue against the possibility of a selection bias in the control group.

TABLE 7

Association of low OGGA and lung cancer

| OGGA cutoff[†] | Controls | Cases | DNA repair OGGA | Smoking | Age | Sex |
|---|---|---|---|---|---|---|
| ≤5.6 (5%) | 7 | 42 | 9.0 (3.2-25.0) | 18.6 (7.1-48.7) | 1.1 (1.1-1.2) | 1.0 (0.4-2.1) |
| >5.6 | 116 | 60 | P = 0.0001 | P = 0.0001 | P = 0.0001 | P = 0.79 |
| ≤5.9 (10%) | 14 | 52 | 7.0 (3.0-16.7) | 20.8 (7.8-55.4) | 1.1 (1.1-1.2) | 1.0 (0.4-2.2) |
| >5.9 | 109 | 50 | P = 0.0001 | P = 0.0001 | P = 0.0001 | P = 0.96 |
| ≤6.2 (15%) | 18 | 60 | 6.5 (2.9-14.5) | 21.5 (8.0-58.0) | 1.1 (1.1-1.2) | 0.9 (0.4-2.0) |
| >6.2 | 105 | 42 | P = 0.0001 | P = 0.0001 | P = 0.0001 | P = 0.77 |
| ≤6.4 (20%) | 25 | 63 | 5.2 (2.4-11.2) | 20.6 (7.9-53.6) | 1.1 (1.1-1.2) | 0.9 (0.4-2.0) |
| >6.4 | 98 | 39 | P = 0.0001 | P = 0.0001 | P = 0.0001 | P = 0.77 |
| ≤6.6 (25%) | 34 | 68 | 4.3 (2.0-9.0) | 21.4 (8.2-55.5) | 1.1 (1.1-1.2) | 0.9 (0.4-2.0) |
| >6.6 | 89 | 34 | P = 0.0002 | P = 0.0001 | P = 0.0001 | P = 0.85 |
| ≤7.3 (50%) | 63 | 83 | 3.9 (1.7-8.6) | 23.0 (8.9-59.2) | 1.1 (1.1-1.2) | 0.9 (0.4-1.8) |
| >7.3 | 60 | 19 | P = 0.0009 | P = 0.0001 | P = 0.0001 | P = 0.67 |

Adjusted Odds Ratio (95% CI)*

The logistic regression model is based on age as a continuous variable, and the dichotomic variables were smoking status (smoker, non-smoker), gender (female, male) and DNA repair activity value (low or normal, with various cutoff values, as indicated). The goodness of fit of the model, as described by $R^2$, is in the range of 58-61%.
*95% CI, 95% confidence interval.
[†]Cutoff values defined for the dichotomic variable of OGGA. The numbers in parentheses show the corresponding percentage of control subjects with OGGA values lower than or equal to the cutoff value.

In case-control studies there is a possibility that the examined variable is a consequence of the disease, rather than being a risk factor. In the present case, the possibility that the lung tumor causes a decrease of OGGA in peripheral blood lymphocytes (PBL) was considered. The OGGA value may be affected, for example, by factors that the tumor secretes into the blood stream. The main treatment of NSCLC is surgical removal of the tumor. This offers a way to distinguish between a causative and a resultive model for the association of PBL OGGA and lung cancer. Once eliminated from the lung, the effect the tumor have (if any) on OGGA in lymphocytes should decay with time. No correlation between OGGA and the time period that passed between surgery and taking the blood sample (ranging from 4 months before surgery to over a year after surgery) was found, indicating that whether the samples were taken before or after surgery had no effect on the level of OGGA in PBL. In the current group of case subjects, most (67/102) samples were taken after surgery. These results, clearly indicate that reduced OGGA is indeed a risk factor in lung cancer.

The simplest biological explanation for the present finding is the following: Low OGGA in PBL reflects low OGGA in the lungs. Correlations between DNA repair activities in PBL and lung cells (Auckley et al., 2001) or gastric mucosa (Kyrtopoulos et al., 1990) were previously reported. The lower DNA repair capacity leads to a reduced ability to repair oxidative DNA damage, and as a result 8-oxoguanine accumulates and leads to an increased mutation rate, which causes a higher cancer risk. In smokers there is an overload of DNA damage in the lungs, and therefore a higher risk is expected. No interaction was found between OGGA values and smoking status, implying that each of the two is an independent risk factor for lung cancer. This means that low OGGA is a risk factor also in non-smokers. This is not surprising, since oxidative DNA damage is a common intracellular damage that occurs even without exposure to external agents (Lindahl, 1993).

As discussed before, OGGA is not reduced in patients with breast cancer. This suggests that the repair of 8-oxoG is a bottleneck in the case of lung cancer, and in some additional cancers, but not in others (e.g., breast cancer). This is consistent with the finding that hereditary defects in particular DNA repair genes cause predisposition to specific types of cancer. For example, defects in nucleotide excision repair were shown to cause skin cancer (Weeda et al., 1993) whereas defects in mismatch repair cause hereditary non-polyposis colon cancer (Modrich, 1994). To our knowledge the results presented herein, are the first demonstration that decreased activity of a specific base excision repair enzyme is associated with cancer.

A useful application of the results of this study would be a quantitative model, which will provide an estimation of the risk of lung cancer associated with a particular OGGA value, age and smoking status. For diseases that do not occur frequently, such as lung cancer, and assuming that the cases and the controls are reasonably representative of the population, the odds ratio can be used as estimated relative risk (Gordis, 1996). Thus, a model was formulated using logistic regression, with age and OGGA as continuous variables, and smoking status as a dichotomic variable (smokers or non-smokers). This yielded OR values for lung cancer and these were taken as an estimation of risk. The OR values were calculated by dividing the odds of each particular group (having a particular age, OGGA value and smoking status) by the odds of 30 years-old non-smokers with a normal OGGA value of 7.0 (the reference group; OR of 1.0). The OR values for a specific age, OGGA value and smoking status are listed in Table 8. For example, according to Table 8, the estimated risk for 30 years-old smokers with a low OGGA value of 4.0, is 118-fold higher than the reference. At the age of 40, the estimated risk will increase to 321-fold higher than the reference. This high estimated risk is primarily the combined result of smoking and low OGGA. Having a low repair activity to start with, smoking causes further overloading of DNA damage, therefore leading to a high cancer risk. This model is instrumental in clarifying the fact that the combination of smoking and low OGGA causes a dramatic increase in susceptibility to lung cancer. For example, 40 years-old non-smokers with an OGGA value of 4.0 have an estimated risk 18-fold higher than the reference, compared to an estimated risk of 321-fold higher than the reference of smokers with the same age and OGGA (Table 8).

The OGGA test can be used to screen smokers for reduced DNA repair capacity. These individuals can be persuaded to quit smoking based on their personal reduced ability to cope with DNA damage. Since smoking is the main contributor to the high relative estimated risk for lung cancer (Tables 7 and 8), quitting smoking is expected to significantly improve the chances of preventing lung cancer. Such an approach of personalized smoking cessation, based on personal susceptibility, may provide a successful and cost-effective strategy to prevent lung cancer, and may be extended to include additional DNA repair assays.

TABLE 8

An odds ratio model for estimating the risk of lung cancer for specific DNA repair OGGA values, age and smoking status

| Age, y | OGGA value | Estimated Risk (Odds Ratio*) | |
|---|---|---|---|
| | | Non-smokers | Smokers |
| 30 | 7 | 1 | 18 |
| 30 | 6 | 2 | 34 |
| 30 | 5 | 3 | 63 |
| 30 | 4 | 7 | 118 |
| 30 | 3 | 12 | 221 |
| 40 | 7 | 3 | 49 |
| 40 | 6 | 5 | 92 |
| 40 | 5 | 9 | 172 |
| 40 | 4 | 18 | 321 |
| 40 | 3 | 33 | 599 |
| 50 | 7 | 7 | 134 |
| 50 | 6 | 14 | 251 |
| 50 | 5 | 26 | 468 |
| 50 | 4 | 48 | 873 |
| 50 | 3 | 90 | 1629 |
| 60 | 7 | 20 | 365 |
| 60 | 6 | 37 | 681 |
| 60 | 5 | 70 | 1272 |
| 60 | 4 | 131 | 2373 |
| 60 | 3 | 244 | 4429 |
| 70 | 7 | 55 | 992 |
| 70 | 6 | 102 | 1852 |
| 70 | 5 | 190 | 3456 |
| 70 | 4 | 355 | 6451 |
| 70 | 3 | 662 | 12040 |

*The Table is based on logistic regression analysis of the case-control study, and therefore the numbers represent only estimated values of risk. The odds ratio is calculated relative to the odds ratio of 30 years-old non-smokers with an OGGA value of 7.0.

The data presented herein indicates that low OGGA is a risk factor for lung cancer also among non-smokers (Tables 7 and 8). What can non-smokers with low OGGA do to protect themselves? One possibility is to make sure that they are not exposed to external sources of oxidative DNA damage such as secondary smoking or ionizing radiation. The latter includes radiology departments in hospitals, nuclear industry, and nuclear reactors. However, oxidative DNA damage is caused also by internal agents; therefore, dietary anti-oxidants might have a protective effect. Large population studies found that oxidants had no protective effect against cancer (reviewed in Collins, 1999; Lippman and Spitz, 2001). However, these food additives might have a protective effect when taken by individuals with low capacity to repair oxidative DNA damage.

Low OGG activity is a risk factor in lymphoma: Analysis of 18 lymphoma patients showed a clear shift to lower OGG DNA repair values (FIGS. 10a-b; Table 6): The mean OGGA value was 6.2±1.8 units/µg protein, significantly lower than in healthy individuals (P=0.0001). Analysis of Normal and Low repair in healthy individuals and in lymphoma patients using logistic regression yielded an adjusted Odds Ratio of 15.2 (95% CI, 3.7-62.5). This means that after adjustment for age, lymphoma patients were 15 times more likely than the healthy controls to have a Low OGGA. This indicates that Low OGGA is a risk factor in lymphoma (Table 9).

TABLE 9

Association of Low OGGA and lymphoma

| Factor | Cases | Controls | Crude OR (95% CI*) | Adjusted** OR (95% CI) |
|---|---|---|---|---|
| OGGA | | | | |
| Normal >5.5 | 12 | 118 | | |
| Low ≦5.5 | 6 | 5 | 11.8 (3.1-44.5) P = 0.0006 | 15.2 (3.7-62.5) P = 0.0002 |

*CI, 95% confidence interval.
**Adjusted for age.

Figures 11A, 11B:
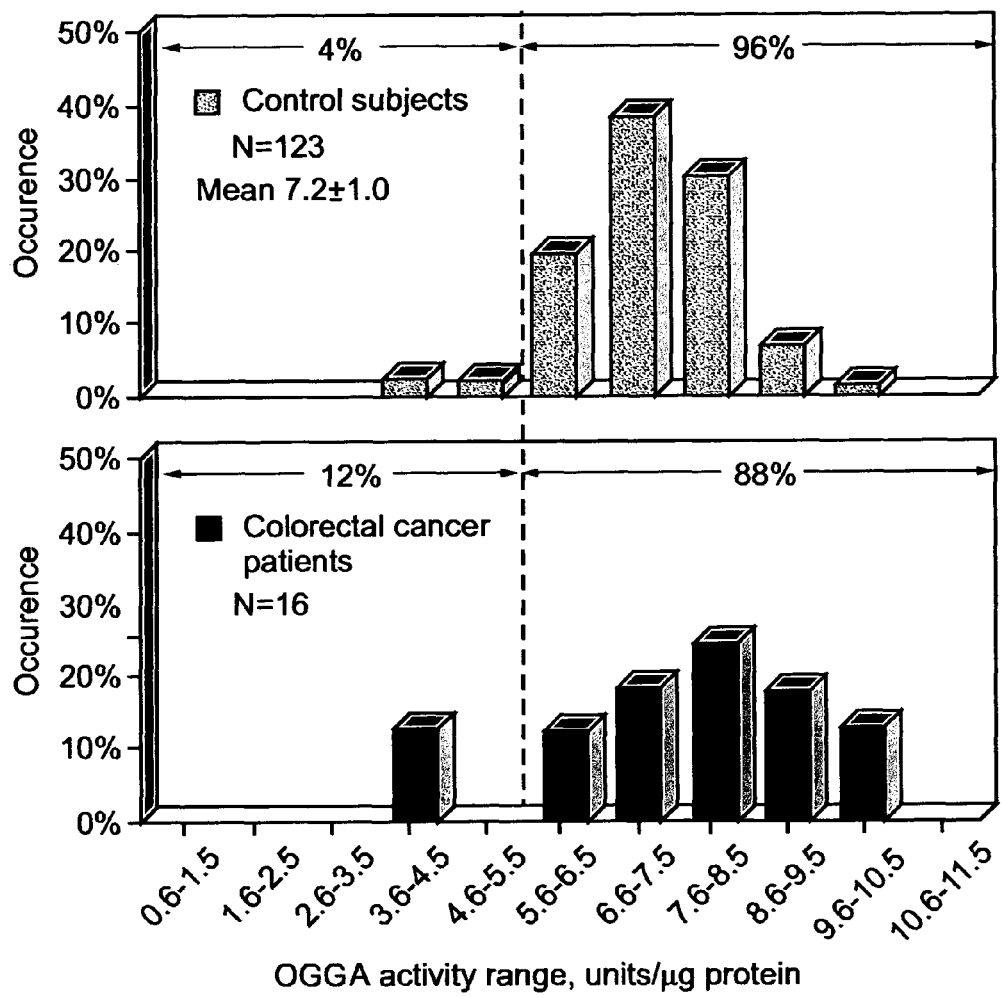
FIGS. 11a-b show OGGA in apparently healthy individuals and in patients with colorectal cancer.

OGG activity seems to be reduced in colorectal cancer patients: An analysis was performed with 16 colorectal cancer patients (FIGS. 11a-b). Two of the patients exhibited low OGG (12%). This data indicates that low OGG is a risk factor in colorectal cancer.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

CITED REFERENCES (Additional References are Cited in the Text)

Aburatani, H., Y. Hippo, T. Ishida, R. Takashima, C. Matsuba, T. Kodama, M. Takao, A. Yasui, K. Yamamoto and M. Asano. (1997) Cloning and characterization of mammalian 8-hydroxyguanine-specific DNA glycosylase/apurinic, apyrimidinic lyase, a functional mutM homologue, Cancer Res., 57, 2151-2156.

Arai, K., K. Morishita, K. Shinmura, T. Kohno, S. R. Kim, T. Nohmi, M. Taniwaki, S. Ohwada and J. Yokota. (1997) Cloning of a human homolog of the yeast OGG1 gene that is involved in the repair of oxidative damage, Oncogene, 14, 2857-2861.

Asami, S., T. Hirano, R. Yamaguchi, Y. Tomioka, H. Itoh and H. Kasai (1996) Increase of a type of oxidative DNA damage, 8-hydroxyguanine, and its repair activity in human leukocytes by cigarette smoking, Cancer Res., 56, 2546-2549.

Asami, S., H. Manabe, J. Miyake, Y. Tsurudome, T. Hirano, R. Yamaguchi, H. Itoh and H. Kasai. (1997) Cigarette smoking induces an increase in oxidative DNA damage, 8-hydroxydeoxyguanosine, in a central site of the human lung, Carcinogenesis, 18, 1763-1766.

Athas, W. F., M. A. Hedayati, G. M. Matanoski, E. R. Farmer and L. Grossman. (1991) Development and field-test validation of an assay for DNA repair in circulating human lymphocytes, Cancer Res., 51, 5786-5793.

Aucklley, D. H., Crowell, R. E., Heaphy, E. R., Stidley, C. A., Lechner, J. F., Gilliland, F. D. and A., B. S. (2001) Reduced DNA-dependent prorein kinase is associated with lung cancer. Carcinogenesis, 22, 723-727.

Audebert, M., S. Chevillard, C. Levalois, G. Gyapay, A. Vieillefond, J. Klijanienko, P. Vielh, A. K. El Naggar, S. Oudard, S. Boiteux and J. P. Radicella. (2000) Alterations of the DNA repair gene OGG1 in human clear cell carcinomas of the kidney, Cancer Res., 60, 4740-4744.

Bessho, T., R. Roy, K. Yamamoto, H. Kasai, S. Nishimura, K. Tano and S. Mitra. (1993) Repair of 8-hydroxyguanine in DNA by mammalian N-methylpurine-DNA glycosylase, Proc. Natl. Acad. Sci. USA, 90, 8901-8904.

Bishop, J. M. (1995) Cancer: The rise of the genetic paradigm, Genes & Dev., 9, 1309-1315.

Bjoras, M., L. Luna, B. Johnsen, E. Hoff, T. Haug, T. Rognes and E. Seeberg. (1997) Opposite base-dependent reactions of a human base excision repair enzyme on DNA containing 7,8-dihydro-8-oxoguanine and abasic sites, EMBO J., 16, 6314-6322.

Chevillard, S., J. P. Radicella, C. Levalois, J. Lebeau, M. F. Poupon, S. Oudard, B. Dutrillaux and S. Boiteux. (1998) Mutations in OGG1, a gene involved in the repair of oxidative DNA damage, are found in human lung and kidney tumours, Oncogene, 16, 3083-3086.

Collins, A. R. (1999) Oxidative DNA damage, antioxidants, and cancer. BioEssays, 21, 238-246. Connor, F., D. Bertwistle, P. J. Mee, G. M. Ross, S. Swift, E. Grigorieva, V. L. J. Tybulewicz and A. Ashworth. (1997) Tumorigenesis and a DNA repair defect in mice with a truncating Brca2 mutation, Nature Genet, 17, 423-430.

Dianov, G., A. Price and T. Lindahl. (1992) Generation of single-nucleotide repair patches following excision of uracil residues from DNA, Mol. Cell Biol., 12, 1605-1612.

Echols, H. and M. F. Goodman. (1991) Fidelity mechanisms in DNA replication, Annu. Rev. Biochem., 60, 477-511.

Engelward, B. P., G. Weeda, M. D. Wyatt, J. L. Broekhof, J. de Wit, I. Donker, J. M. Allan, B. Gold, J. H. Hoeijmakers and L. D. Samson. (1997) Base excision repair deficient mice lacking the Aag alkyladenine DNA glycosylase, Proc. Natl. Acad. Sci. USA, 94, 13087-13092.

Fishel, R., M. K. Lescoe, M. R. Rao, N. G. Copeland, N. A. Jenkins, J. Garber, M. Kane and R. Kolodner. (1993) The human mutator gene homolog MSH2 and its association with hereditary nonpolyposis colon cancer, Cell, 75, 1027-38.

Fortini, P., B. Pascucci, E. Parlanti, R. W. Sobol, S. H. Wilson and E. Dogliotti. (1998) Different DNA polymerases are involved in the short- and long-patch base excision repair in mammalian cells, Biochemistry, 37, 3575-3580.

Friedberg, E. C., G. C. Walker and W. Siede (1995) DNA repair and mutagenesis, ASM Press, Washington, D. C.

Gajewski, E., G. Rao, Z. Nackerdien and M. Dizdaroglu. (1990) Modification of DNA bases in mammalian chromatin by radiation-generated free radicals, Biochemistry, 29, 7876-7882.

Gordis, L. (1996) Epidemiology, W. B. Saunders Co., Philadelphia.

Gowen, L. C., A. V. Avrutskaya, A. M. Latour, B. H. Koller and S. A. Leadon. (1998) BRCA1 required for transcription-coupled repair of oxidative DNA damage, Science, 281, 1009-1012.

Hanawalt, P. C. (1994) Transcription-coupled repair and human disease, Science, 266, 1957-1958.

Hang, B., B. Singer, G. P. Margison and R. H. Elder. (1997) Targeted deletion of alkylpurine-DNA -N-glycosylase in mice eliminates repair of 1, N6-ethenoadenine and hypoxanthine but not 3, N4-ethenocytosine or 8-oxoguanine, Proc. Natl. Acad. Sci. USA, 94, 12869-12874.

Hazra, T. K., T. Izumi, L. Maidt, R. A. Floyd and S. Mitra. (1998) The presence of two distinct 8-oxoguanine repair enzymes in human cells; their potential complementary roles in preventing mutation., Nucleic Acids Res., 26, 5116-5122.

Helzlsouer, K. J., E. L. Harris, R. Parshad, H. R. Perry, F. M. Proce and K. K. Sanford. (1996) DNA repair proficiency: Potential susceptibility factor for breast cancer, J. Natl. Cancer. Inst., 88, 754-755.

Hernandez-Boussard, T., P. Rodriguez-Tome, R. Montesano and P. Hainaut, P. (1999) IARC p53 mutation database: a relational database to compile and analyze p53 mutations in human tumors and cell lines. International Agency for Research on Cancer, Hum. Mutat., 14, 1-8.

Hollstein, M., Shomer, B., Greenblatt, M., Soussi, T., Hovig, E., Montesano, R. and Harris, C. C. (1996) Somatic point mutations in the p53 gene of human tumors and cell lines: updated compilation. Nucleic Acids Res., 24, 141-146.

Hutchinson, F. (1985) Chemical changes induced in DNA by ionizing radiation, Prog. Nucleic Acid Res. Mol. Biol., 32, 115-154.

Hyun, J. W., J. Y. Choi, H. H. Zeng, Y. S. Lee, H. S. Kim, S. H. Yoon and M. H. Chung. (2000) Leukemic cell line, KG-1 has a functional loss of hOGG1 enzyme due to a point mutation and 8-hydroxydeoxyguanosine can kill KG-1, Oncogene, 19, 44764479.

Ishida, T., Y. Hippo, Y. Nakahori, I. Matsushita, T. Kodama, S. Nishimura and H. Aburatani. (1999) Structure and chromosome location of human OGG1, Cytogenet. Cell Genet., 85, 232-236.

Jyothish, B., R. Ankathil, B. Chandini, B. Vinodkumar, G. Sunil Nayar, D. Dinesh Roy, J. Madhavan and M. Krishnan Nair. (1998) DNA repair proficiency: a potential marker for identification of high risk members in breast cancer families, Cancer Lett., 124, 9-13.

Kim, K., S. Biade and Y. Matsumoto. (1998) Involvement of flap endonuclease 1 in base excision DNA repair, J. Biol. Chem., 273, 8842-8848.

Kleinbaum, D. G. (1994) Logistic Regression, Springer-Verlag, New York.

Klungland, A., I. Rosewell, S. Hollenbach, E. Larsen, G. Daly, B. Epe, E. Seeberg, T. Lindahl and D. E. Barnes. (1999) Accumulation of premutagenic DNA lesions in mice defective in removal of oxidative base damage, Proc. Natl. Acad. Sci. USA, 96, 13300-13305.

Kyrtopoulos, S. A., Ampatzi, P., Davaris, P., Haritopoulos, N. and Golematis, B. (1990) Studies in gastric carcinogenesis. IV. O6-methyguanine and its repair in normal and atrophic biopsy specimen of human gastric mucosa. Correlation of O6-methylguanine-DNA alkyltransferase activities in gastric mucosa and circulating lymphocytes. Carcinogenesis, 11, 431-436.

Laval, F. (1994) Expression of the *E. coli* fpg gene in mammalian cells reduces mutagenicity of g rays, Nucleic Acids Res., 22, 4943-4946.

Le Page, F., E. E. Kwoh, A. Avrutskaya, A. Gentil, S. A. Leadon, A. Sarasin and P. K. Cooper. (2000) Transcription-coupled repair of 8-oxoguanine: requirement for XPG, TFIIH, and CSB and implications for Cockayne syndrome, Cell, 101, 159-171.

Le Page, F., V. Randrianarison, D. Marot, J. Cabannes, M. Perricaudet, J. Feunteun and A. Sarasin. (2000) BRCA1 and BRCA2 are necessary for the transcription-coupled repair of the oxidative 8-oxoguanine lesion in human cells, Cancer Res., 60, 5548-5552.

Leach, F. S., N. C. Nicolaides, N. Papadopoulos, B. Liu, J. Jen, R. Parsons, P. Peltomaki, P. Sistonen, L. A. Aaltonen, M. Nystromlahti, X. Y. Guan, J. Zhang, P. S. Meltzer, J. W. Yu, F. T. Kao, D. J. Chen, K. M. Cerosaletti, R. E. K. Fournier, S. Todd, T. Lewis, R. J. Leach, S. L. Naylor, J. Weissenbach, J. P. Mecklin, H. Jarvinen, G. M. Petersen, S. R. Hamilton, J. Green, J. Jass, P. Watson, H. T. Lynch, J. M. Trent, J. M. Trent, A. de la Chapelle, K. W. Kinzler and B. Vogelstein. (1993) Mutations of a mutS homolog in hereditary nonpolyposis colorectal cancer, Cell, 75, 1215-1225.

Leanderson, P. and C. Tagesson. (1992) Cigarette smoke-induced DNA damage in cultured human lung cells: role of hydroxyl radicals and endonuclease activation, Che. Biol. Interact., 81, 197-208.

Lindahl, T. (1993) Instability and decay of the primary structure of DNA. Nature, 362, 709-715.

Lippman, S. M. and Spitz, M. R. (2001) Lung cancer chemoprevention: An integrated approach. J. Clin. Oncol., 19, 74s-82s.

Livneh, Z., O. Cohen-Fix, R. Skaliter and T. Elizur. (1993) Replication of damaged DNA and the molecular mechanism of ultraviolet light mutagenesis, CRC Crit. Rev. Biochem. Mol. Biol., 28, 465-513.

Lu, R., H. M. Nash and G. L. Verdine. (1997) A mammalian DNA repair enzyme that excises oxidatively damaged guanines maps to a locus frequently lost in lung cancer., Curr. Biol., 7, 397-407.

Maki, H. and M. Sekiguchi. (1992) MutT protein specifically hydrolyses a potent mutagenic substrate for DNA synthesis, Nature (London), 355, 273-275.

Mattson, M. E., Pollack, E. S. & Cullen, J. W. (1987) What are the odds that smoking will kill you? Am. J Public Health 77, 425-431.

Minna, J.D., Roth, J. A. and Gazdar, A. F. (2002) Focus on lung cancer. Cancer Cell, 1, 49-52.

Minowa, O., T. Arai, M. Hirano, Y. Monden, S. Nakai, M. Fukuda, M. Itoh, H. Takano, Y. Hippou, H. Aburatani, K. Masumura, T. Nohmi, S. Nishimura and T. Noda. (2000) Mmh/Oggl gene inactivation results in accumulation of 8-hydroxyguanine in mice, Proc. Natl. Acad. Sci. USA, 97, 4156-4161.

Modrich, P. (1994) Mismatch repair, genetic stability, and cancer, Science, 266, 1959-1960.

Monden, Y., T. Arai, M. Asano, E. Ohtsuka, H. Aburatani and S. Nishimura. (1999) Human MMH (OGG1) Type la Protein Is a Major Enzyme for Repair of 8-Hydroxyguanine Lesions in Human Cells, Biochem. Biophys. Res. Commun., 258, 605-610.

Parshad, R., F. M. Price, V. A. Bohr, K. H. Cowans, J. A. Zujewski and K. K. Sanford. (1996) Deficient DNA repair capacity, a predisposing factor in breast cancer, Brit. J. Cancer, 74, 1-5.

Parsons, R., G. M. Li, M. J. Longley, W. H. Fang, N. Papadopoulos, J. Jen, l. C. A. de, K. W. Kinzier, B. Vogelstein and P. Modrich. (1993) Hypermutability and mismatch repair deficiency in RER+ tumor cells, Cell, 75, 1227-36.

Patel, K. J., V. P. C. C. Yu, H. Lee, A. Corcoran, F. C. Thistlethwaite, M. J. Evans, W. H. Colledge, L. S. Friedman, B. A. J. Ponder and A. R. Venkitaraman. (1998) Involvement of Brca2 in DNA Repair, Molecular Cell, 1, 347-357.

Patel, R. K., A. H. Trivedi, D. C. Arora, J. M. Bhatavdekar and D. D. Patel. (1997) DNA repair proficiency in breast cancer patients and their first-degree relatives, Int. J. Cancer, 73, 20-24.

Pavlov, Y. I., D. T. Minnick, S. Izuta and T. A. Kunkel. (1994) DNA replication fidelity with 8-oxodeoxyguanosine triphosphate, Biochemistry, 33, 4695-4701.

Radicella, J. P., C. Dherin, C. Desmaze, M. S. Fox and S. Boiteux. (1997) Cloning and characterization of hOGG1, a human homolog of the OGG1 gene of Saccharomyces cerevisiae, Proc. Natl. Acad. Sci. USA, 94, 8010-8015.

Reardon, J. T., T. Bessho, H. C. Kung, P. H. Bolton and A. Sancar. (1997) In vitro repair of oxidative DNA damage by human nucleotide excision repair system: possible explanation for neurodegeneration in xeroderma pigmentosum patients, Proc. Natl. Acad. Sci. USA, 94, 9463-9468.

Roldan-Arjona, T., Y. F. Wei, K. C. Carter, A. Klungland, C. Anselmino, R. P. Wang, M. Augustus and T. Lindahl. (1997) Molecular cloning and functional expression of a human cDNA encoding the antimutator enzyme 8-hydroxyguanine DNA glycosylase, Proc. Natl. Acad. Sci. USA, 94, 8016-8020.

Rosenquist, T. A., D. O. Zharkov and A. P. Grollman. (1997) Cloning and characterization of a mammalian 8-oxoguanine DNA glycosylase, Proc. Natl. Acad. Sci. USA, 94, 7429-7434.

Runger, T. M., B. Epe and K. Moller. (1995) Repair of ultraviolet B and singlet oxygen-induced DNA damage in xeroderma pigmentosum cells, J. Invest. Dermatol., 104, 68-73.

Sagher, D., T. Karrison, J. L. Schwartz, R. Larson, P. Meier and B. Strauss. (1988) Low O6-alkylguanine DNA alkyltransferase activity in the peripheral blood lymphocytes of patients with therapy-related acute nonlymphocytic leukemia, Cancer Res., 48, 3084-3089.

Sancar, A. (1994) Mechanisms of DNA repair, Science, 266, 1954-1956.

Savitsky, K., A. Bar-Shira, S. Gilad, G. Rotman, Y. Ziv, L. Vanagaite, D. A. Tagle, S. Smith, T. Uziel, S. Sfez, M. Ashkenazi, I. Pecker, M. Frydman, R. Harnik, S. R. Patanjali, A. Simmons, G. A. Clines, A. Sartiel, R. A. Gatti, L. Chessa, 0. Sanal, M. Lavin, N. G. J. Jaspers, A. M. R. Taylor, C. F. Arlett, T. Miki, S. M. Weissman, M. Lovett, F. S. Collins and Y. Shiloh. (1995) A single Ataxia Telangiectasia gene with a product similar to PI-3 kinase, Science, 268, 1749-1753.

Scully, R., J. Chen, A. Plug, Y. Xiao, D. Weaver, J. Feunteun, T. Ashley and D. M. Livingston. (1997) Association of BRCA1 with Rad51 in Mitotic and Meiotic cells, Cell, 88, 265-275.

Sharan, S. K., M. Morimatsu, U. Albrecht, D. S. Lim, E. Regel, C. Dinh, A. Sands, G. Eichele, P. Hasty and A. Bradley. (1997) Embryonic lethality and radiation hypersensitivity mediated by Rad51 in mice lacking Brca2, Nature, 386, 804-810.

Shibutani, S., M. Takeshita and A. P. Grollman. (1991) Insertion of specific bases during DNA synthesis past the oxidation-damaged base 8-oxodG, Nature, 349, 431-434.

Shinmura, K., T. Kohno, H. Kasai, K. Koda, H. Sugimura and J. Yokota. (1998) Infrequent mutations of the hOGG1 gene, that is involved in the excision of 8-hydroxyguanine in damaged DNA, in human gastric cancer, Jpn. J. Cancer Res., 89, 825-828.

Singhal, R. K., R. Prasad and S. H. Wilson. (1995) DNA polymerase beta conducts the gap-filling step in uracil-initiated base excision repair in a bovine testis nuclear extract, J Biol Chem, 270, 949-957.

Srivastava, S., Z. Zou, K. Pirollo, W. Blattner and E. H. Chang. (1990) Germ-line transmission of a mutated p53 in a cancer-prone family with Li-Fraumeni syndrome, Nature (London), 348, 747-749.

Strauss, B. S. (1985) Translesion DNA synthesis: polymerase response to altered nucleotide, Cancer Surv., 4, 493-516.

Vandenbroucke, J. P., T. Koster, E. Briet, P. H. Reitsma, R. M. Bertina and F. R. Rosendaal. (1994) Increased risk of venous thrombosis in oral-contraceptive users who are carriers of factor V Leiden mutation, Lancet, 344, 1453-1457.

Vogelstein, B. and K. W. Kinzler. (1993) The multistep nature of cancer, Trends Genet., 9, 138-141.

Weeda, G., J. H. J. Hoeijmakers and D. Bootsma. (1993) Genes controlling nucleotide excision repair in eukaryotic cells, BioEssays, 15, 249-258.

Wei, Q., L. Cheng, W. K. Hong and M. R. Spitz. (1996) Reduced DNA repair capacity in lung cancer patients, Cancer Res., 56, 4103-4107.

Wei, Q., G. M. Matanoski, E. R. Farmer, M. A. Hedayati and L. Grossman. (1993) DNA repair and aging in basal cell carcinoma: a molecular epidemiology study, Proc. Natl. Acad. Sci. U S A, 90, 1614-1618.

Wei, Q., G. M. Matanoski, E. R. Farmer, M. A. Hedayati and L. Grossman. (1994) DNA repair and susceptibility to basal cell carcinoma: a case-control study, Am. J. Epidemiol., 140, 598-607.

Weinberg, R. A. (1989) Oncogenes, antioncogenes, and the molecular bases of multistep carcinogenesis, Cancer Res., 49, 3713-3721.

Wikman, H., A. Risch, F. Klimek, P. Schmezer, B. Spiegelhalder, H. Dienemann, K. Kayser, V. Schulz, P. Drings and H. Bartsch. (2000) hOGG1 polymorphism and loss of heterozygosity (LOH): significance for lung cancer susceptibility in a Caucasian population, Int. J. Cancer, 88, 932-937.

Wood, M. L., M. Dizdaroglu, E. Gajewski and J. M. Essigmann. (1990) Mechanistic studies of ionizing radiation and oxidative mutagenesis: Genetic effects of a single 8-hydroxyguanine (7-hydro-8-oxo-guanine) residue inserted at a unique site in a viral genome, Biochemistry, 29, 7024-7032.

What is claimed is:

1. A method of determining a risk of a human subject to develop non-small cell lung cancer, the method comprising determining a level of catalytic activity of 8-oxoguanine DNA glycosylase in a sample of peripheral blood lymphocytes of the subject, and, according to said level, determining the risk of the subject to develop non-small cell lung cancer, wherein a level of said catalytic activity below a predetermined value is indicative of an increased risk of said subject to develop non-small cell lung cancer, and wherein said subject is a smoker or a non-smoker.

2. The method of claim 1, wherein said level of catalytic activity is determined using a double-stranded DNA substrate consisting of the complementary oligonucleotides having a polynucleotide sequence as set forth in SEQ ID NOs: 1 and 2.

3. The method of claim 1, wherein the risk is expressed as a fold risk increase as is compared to a normal, apparently healthy, population, or a reference control group.

4. The method of claim 1, wherein the risk is expressed in enzyme specific activity units.

5. The method of claim 1, wherein the risk is expressed as a magnitude of a scale.

6. The method of claim 1, wherein the subject is known to be, or is about to be, exposed to environmental conditions associated with an increased risk of developing cancer.

7. A method of determining a risk of a human subject to develop non-small cell lung cancer, the method comprising determining a level of catalytic activity of 8-oxoguanine DNA glycosylase in a sample of peripheral blood lymphocytes of the subject, and, according to said level, determining the risk of the subject to develop non-small cell lung cancer, wherein said subject is exposed to at least one environmental condition associated with an increased risk of developing non-small cell lung cancer, wherein a level of said catalytic activity below a predetermined value is indicative of an increased risk of said subject of developing non-small cell lung cancer, and wherein said subject is a smoker or a non-smoker.

8. The method of claim 7, wherein said environmental conditions are selected from the group consisting of radiation and smoke.

9. The method of claim 7, wherein said level of catalytic activity is determined using a double-stranded DNA substrate consisting of the complementary oligonucleotides having a polynucleotide sequence as set forth in SEQ ID NOs: 1 and 2.

10. The method of claim 7, wherein said environmental condition is smoke.

11. A method of determining a risk of a human subject to develop non-small cell lung cancer, the method comprising determining a level of catalytic activity of 8-oxoguanine DNA glycosylase in a sample of peripheral blood lymphocytes of the subject, and, according to said level, determining the risk of the subject to develop non-small cell lung cancer, wherein a level of said activity below a predetermined value is indicative of an increased risk of said subject to develop non-small cell lung cancer, and wherein said level of said catalytic activity is determined using a double-stranded DNA substrate consisting of the complementary oligonucleotides having a polynucleotide sequence as set forth in SEQ ID NOs: 1 and 2.

12. The method of claim 1, wherein said predetermined value indicative of an increased risk is determined in comparison with 8-oxoguanine DNA glycosylase catalytic activity levels from peripheral blood lymphocytes of normal healthy human control subjects of the same age group and smoking status to that of said subject.

13. The method of claim 11, wherein when said determining said level of 8-oxoguanine DNA glycosylase catalytic activity of said subject indicates increased risk of said subject to develop non-small cell lung cancer, further counseling said subject to avoid exposure to ionizing radiation or smoke.

* * * * *

```
                           SEQUENCE LISTING

<160> NUMBER OF SEQ ID NOS: 14

<210> SEQ ID NO 1
<211> LENGTH: 32
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (18)..(18)
<223> OTHER INFORMATION: 8-oxoguanine (8-oxoG)

<400> SEQUENCE: 1
ccggtgcatg acactgtnac ctatcctcag cg                                   32

<210> SEQ ID NO 2
<211> LENGTH: 32
<212> TYPE: DNA
<213> ORGANISM: Artificial sequence
<220> FEATURE:
<223> OTHER INFORMATION: synthetic oligonucleotide

<400> SEQUENCE: 2
cgctgaggat aggtcacagt gtcatgcacc gg                                   32

<210> SEQ ID NO 3
<211> LENGTH: 2062
<212> TYPE: DNA
<213> ORGANISM: Homo sapiens

<400> SEQUENCE: 3
ctcccagccc gtctccccgc tccagtttag aacctaattc ccaattcccg gaccgggccc     60
agccctgggc tcttactgtc cgcttttgct gggacctgtt ccacaaatgg gcgtcttctg    120
ccttgggccg tgggggttgg gccggaagct gcggacgcct gggaagggc cgctgcagct     180 cttgagccgc ctctgcgggg accacttgca ggccatccca gccaagaagg ccccggctgg    240
gcaggaggag cctgggacgc cgccctcctc gccgctgagt gccgagcagt tggaccggat    300
ccagaggaac aaggccgcgg ccctgctcag actcgcggcc cgcaacgtgc ccgtgggctt    360
tggagagagc tggaagaagc acctcagcgg ggagttcggg aaaccgtatt ttatcaagct    420
```

| | |
|---|---:|
| aatgggattt gttgcagaag aaagaaagca ttacactgtt tatccacccc cacaccaagt | 480 |
| cttcacctgg acccagatgt gtgacataaa agatgtgaag gttgtcatcc tgggacagga | 540 |
| tccatatcat ggacctaatc aagctcacgg gctctgcttt agtgttcaaa ggcctgttcc | 600 |
| gcctccgccc agtttggaga acatttataa agagttgtct acagacatag aggattttgt | 660 |
| tcatcctggc catggagatt tatctgggtg ggccaagcaa ggtgttctcc ttctcaacgc | 720 |
| tgtcctcacg gttcgtgccc atcaagccaa ctctcataag gagcgaggct gggagcagtt | 780 |
| cactgatgca gttgtgtcct ggctaaatca gaactcgaat ggccttgttt tcttgctctg | 840 |
| gggctcttat gctcagaaga agggcagtgc cattgatagg aagcggcacc atgtactaca | 900 |
| gacggctcat ccctccccctt tgtcagtgta tagagggttc tttggatgta gacacttttc | 960 |
| aaagaccaat gagctgctgc agaagtctgg caagaagccc attgactgga aggagctgtg | 1020 |
| atcatcagct gaggggtggc cttttgagaag ctgctgttaa cgtatttgcc agttacgaag | 1080 |
| ttccactgaa aatttttccta ttaattctta agtactctgc ataaggggga aaagcttcca | 1140 |
| gaaagcagcc atgaaccagg ctgtccagga atggcagctg tatccaacca caaacaacaa | 1200 |
| aggctacccct ttgaccaaat gtctttctct gcaacatggc ttcggcctaa aatatgcaga | 1260 |
| agacagatga ggtcaaatac tcagttggct ctctttatct cccttgcctt tatggtgaaa | 1320 |
| caggggagat gtgcaccttt caggcacagc cctagtttgg cgcctgctgc tccttggttt | 1380 |
| tgcctggtta gactttcagt gacagatgtt ggggtgtttt tgcttagaaa ggtccccttg | 1440 |
| tctcagccctt gcagggcagg catgccagtc tctgccagtt ccactgcccc cttgatctttt | 1500 |
| gaaggagtcc tcaggcccct cgcagcataa ggatgttttg caacttttcca gaatctggcc | 1560 |
| cagaaattag ggctcaattt cctgattgta gtagagggtta agattgctgt gagctttatc | 1620 |
| agataagaga ccgagagaag taagctgggt cttgttattc cttgggtgtt ggtggaataa | 1680 |
| gcagtggaat ttgaacaagg aagaggagaa aagggaattt tgtctttatg gggtggggtg | 1740 |
| attttctcct agggttatgt ccagttgggg ttttttaaggc agcacagact gccaagtact | 1800 |
| gttttttttta accgactgaa atcactttgg gatatttttt cctgcaacac tggaaagttt | 1860 |
| tagttttttta agaagtactc atgcagatat atatatatat attttttccca gtcctttttt | 1920 |
| taagagacgg tctttattgg gtctgcacct ccatccttga tcttgttagc aatgctgttt | 1980 |
| ttgctgttag tcgggttaga gttggctcta cgcgaggttt gttaataaaa gtttgttaaa | 2040 |
| agttcaaaaa aaaaaaaaaa aa | 2062 |

```
<210> SEQ ID NO 4
<211> LENGTH: 1570
<212> TYPE: DNA
<213> ORGANISM: Homo sapiens

<400> SEQUENCE: 4
```

| | |
|---|---:|
| aacgggatgg ggagctggac cagcagatta tgagcttaca gaaagcctgg cctacatttt | 60 |
| actcttttttg gatttcttcc tcatcaagag actgctgcag tgcctgtcat gtgacagcgg | 120 |
| catggacata tgccccaggc tttcctgctg ggtccatcc atgagcctgc aggtgccctc | 180 |
| atggagcccc agccctgccc tggaagcttg gctgagagct tcctggagga ggagcttcgg | 240 |
| ctcaatgctg agctgagcca gctgcagttt tcggagcctg tgggcatcat ctacaatccc | 300 |
| gtggagtatg catgggagcc acatcgcaac tacgtgactc gctactgcca gggcccccaag | 360 |
| gaagtactct tcctgggcat gaaccctgga ccttttggca tggcccagac tggggtgccc | 420 |
| tttggggaag taagcatggt ccgggactgg ttgggcattg tggggcctgt gctgaccccct | 480 |

-continued

| | |
|---|---|
| cccccaagagc atcctaaacg accagtgctg ggactggagt gcccacagtc agaagtgagt | 540 |
| ggtgcccgat tctggggctt tttccggaac ctctgtggac agcctgaggt cttcttccat | 600 |
| cactgttttg tccacaatct atgccctctg cttttcctgg ctcccagcgg gcgcaacctt | 660 |
| actcctgctg agctgcctgc caagcagcga gaacagcttc ttgggatctg tgatgcagcc | 720 |
| ctctgccggc aggtgcagct gctggggtg cggctggtgg tgggagttgg gcgactggca | 780 |
| gagcagcggg cacgacgggc tctggcaggc ctgatgccag aggtccaggt ggaagggctc | 840 |
| ctgcatccct ctccccgtaa cccacaggcc aacaagggct gggaggcagt ggccaaggaa | 900 |
| agattgaatg agctggggct gctgccactg ctgttgaaat gagtgccctt ggggccttgc | 960 |
| atgggacaca ttcaagacct cgaagtcatt cttggccaag cagatgacaa cacatctcct | 1020 |
| ggactggagc aaaaggtcct tctgtgcacc ctggtcgctg ggaaacgtat tctttgatct | 1080 |
| gttgaactgt cttccaacct gccatggcag ttttgacact actcctgttt gccctcctga | 1140 |
| ttcctgcttt ctttacctttt taacattgcc ccttttcaggg gacccccactt tgtagggaat | 1200 |
| ctgcagaagg tgtgcttttg cacttgcaga ctgctctacc tcagtgtttc cttgggagac | 1260 |
| tttattcagc tgagagtgcc ctagacagta acttctaagg tcacgtttac tatttcagag | 1320 |
| gaaatatctt gccaggatac ctacccatcc ttatagaaca gttacctta gctgacccct | 1380 |
| ttcctcacag ggaccaagac aaagcatggg acatgaaatt aagagtgaac ttcttatggg | 1440 |
| aggctgcagc tggatcagag gaaaaatcca gtgtgacaga gtgcaagtca gaagacctgg | 1500 |
| cttttcatcc cagcttttgaa acttggaact ttttgattga caaattaata aacctctcta | 1560 |
| tgcctcaggc | 1570 |

<210> SEQ ID NO 5
<211> LENGTH: 2470
<212> TYPE: DNA
<213> ORGANISM: Homo sapiens

<400> SEQUENCE: 5

| | |
|---|---|
| ggcggctgta gccgaggggg cggccggaaa gcagcggcgg cgtctgggc gctttcgcaa | 60 |
| cattcagacc tcggttgcag cccggtgccg tgagctgaag aggtttcaca tcttactccg | 120 |
| ccccacaccc tgggcgttgc ggcgctgggc tcgttgctgc agccggaccc tgctcgatgg | 180 |
| gcacgactgg gctggagagt ctgagtctgg ggaccgcgg agctgccccc accgtcacct | 240 |
| ctagtgagcg cctagtccca gacccgccga atgacctccg caaagaagat gttgctatgg | 300 |
| aattggaaag agtgggagaa gatgaggaac aaatgatgat aaaagaagc agtgaatgta | 360 |
| atcccttgct acaagaaccc atcgcttctg ctcagtttgg tgctactgca ggaacagaat | 420 |
| gccgtaagtc tgtcccatgt ggatgggaaa gagttgtgaa gcaaaggtta tttgggaaga | 480 |
| cagcaggaag atttgatgtg tactttatca gcccacaagg actgaagttc agatccaaaa | 540 |
| gttcacttgc taattatctt cacaaaaatg gagagacttc tcttaagcca gaagattttg | 600 |
| attttactgt actttctaaa aggggtatca agtcaagata taaagactgc agcatggcag | 660 |
| ccctgacatc ccatctacaa aaccaaagta acaattcaaa ctggaacctc aggacccgaa | 720 |
| gcaagtgcaa aaaggatgtg tttatgccgc caagtagtag ttcagagttg caggagagca | 780 |
| gaggactctc taactttact tccactcatt tgcttttgaa agaagatgag ggtgttgatg | 840 |
| atgttaactt cagaaaggtt agaaagccca aggaaaggt gactattttg aaaggaatcc | 900 |
| caattaagaa aactaaaaaa ggatgtagga agagctgttc aggttttgtt caaagtgata | 960 |
| gcaaaagaga atctgtgtgt aataaagcag atgctgaaag tgaacctgtt gcacaaaaaa | 1020 |

-continued

| | |
|---|---|
| gtcagcttga tagaactgtc tgcatttctg atgctggagc atgtggtgag accctcagtg | 1080 |
| tgaccagtga agaaaacagc cttgtaaaaa aaaagaaag atcattgagt tcaggatcaa | 1140 |
| attttgttc tgaacaaaaa acttctggca tcataaacaa attttgttca gccaaagact | 1200 |
| cagaacacaa cgagaagtat gaggatacct ttttagaatc tgaagaaatc ggaacaaaag | 1260 |
| tagaagttgt ggaaaggaaa gaacatttgc atactgacat tttaaaacgt ggctctgaaa | 1320 |
| tggacaacaa ctgctcacca accaggaaag acttcactgg tgagaaaata tttcaagaag | 1380 |
| ataccatccc acgaacacag atagaaagaa ggaaaacaag cctgtatttt tccagcaaat | 1440 |
| ataacaaaga agctcttagc cccccacgac gtaaagcctt taagaaatgg cacctcctc | 1500 |
| ggtcaccttt taatctcgtt caagaaacac ttttcatga tccatggaag cttctcatcg | 1560 |
| ctactatatt tctcaatcgg acctcaggca aatggcaat acctgtgctt tggaagtttc | 1620 |
| tggagaagta tccttcagct gaggtagcaa gaaccgcaga ctggagagat gtgtcagaac | 1680 |
| ttcttaaacc tcttggtctc tacgatcttc gggcaaaaac cattgtcaag ttctcagatg | 1740 |
| aatacctgac aaagcagtgg aagtatccaa ttgagcttca tgggattggt aaatatggca | 1800 |
| acgactctta ccgaattttt tgtgtcaatg agtggaagca ggtgcaccct gaagaccaca | 1860 |
| aattaaataa atatcatgac tggctttggg aaaatcatga aaaattaagt ctatcttaaa | 1920 |
| ctctgcagct ttcaagctca tctgttatgc atagctttgc acttcaaaaa agcttaatta | 1980 |
| agtacaacca accacctttc cagccataga gattttaatt agcccaacta gaagcctagt | 2040 |
| gtgtgtgctt tcttaatgtg tgtgccaatg gtggatcttt gctactgaat gtgtttgaac | 2100 |
| atgttttgag atttttttaa aataaattat tatttgacaa caatccaaaa aaaatacggc | 2160 |
| ttttccaatg atgaaatata atcagaagat gaaaaatagt tttaaactat caataataca | 2220 |
| aagcaaattt ctatcagcct tgctaaagct aggggcccac taaatatttt tatcggctag | 2280 |
| gcgtggtggt gcatgcctgt aatctcggaa ggctgaggca ggaggatcat ttgagctcat | 2340 |
| gagggcccag gaggtcaagg cttcagtgag ccatgatcat gccactgcac tccagtctgg | 2400 |
| atgacagaga gagaccctgt ctcaaaaaat atatttaa aaaataaaaa taaaagctga | 2460 |
| ccccaaaagac | 2470 |

<210> SEQ ID NO 6
<211> LENGTH: 3410
<212> TYPE: DNA
<213> ORGANISM: Homo sapiens

<400> SEQUENCE: 6

| | |
|---|---|
| gcaccaggcg cccagtggag ccgtttggga gaattgcctg cgccacgcag cggggccgga | 60 |
| caggcggtaa ggatctgatt aggctttcga acttgagttt gactgatgtc ttctgtgtgg | 120 |
| tgtccgctaa atcccacagc atataggatc agtcgcattg gttataaggt ttgcttctgg | 180 |
| ctgggtgcgg tggctcatgc ctgtaatcca acattgggag gccaaggcag gcggaccacc | 240 |
| tgaagtcggg agcttgagtc cagccactgt ctgggtactg ccagccatcg ggcccaggtc | 300 |
| tctggggttg tcttaccgca gtgagtacca cgcggtacta cagagaccgg ctgcccgtgt | 360 |
| gcccggcagg tggagccgcc gcatcagcgg cctcgggaa tggaagcgga gaacgcgggc | 420 |
| agctattccc ttcagcaagc tcaagctttt tatacgtttc catttcaaca actgatggct | 480 |
| gaagctccta atatggcagt tgtgaatgaa cagcaaatgc cagaagaagt tccagcccca | 540 |
| gctcctgctc aggaaccagt gcaagaggct ccaaaaggaa gaaaagaaa acccagaaca | 600 |
| acagaaccaa aacaaccagt ggaacccaaa aaacctgttg agtcaaaaaa atctggcaag | 660 |

| | | | | | |
|---|---|---|---|---|---|
| tctgcaaaac | caaagaaaaa | acaagaaaaa | attacagaca | catttaaagt | aaaaagaaaa | 720 |
| gtagaccgtt | ttaatggtgt | ttcagaagct | gaacttctga | ccaagactct | ccccgatatt | 780 |
| ttgaccttca | atctggacat | tgtcattatt | ggcataaacc | cgggactaat | ggctgcttac | 840 |
| aaagggcatc | attaccctgg | acctggaaac | cattttgga | agtgtttgtt | tatgtcaggg | 900 |
| ctcagtgagg | tccagctgaa | ccatatggat | gatcacactc | taccagggaa | gtatggtatt | 960 |
| ggatttacca | acatggtgga | aaggaccacg | cccggcagca | aagatctctc | cagtaaagaa | 1020 |
| tttcgtgaag | gaggacgtat | tctagtacag | aaattacaga | aatatcagcc | acgaatagca | 1080 |
| gtgtttaatg | gaaatgtat | ttatgaaatt | tttagtaaag | aagttttgg | agtaaaggtt | 1140 |
| aagaacttgg | aatttgggct | tcagccccat | aagattccag | acacagaaac | tctctgctat | 1200 |
| gttatgccat | catccagtgc | aagatgtgct | cagtttcctc | gagcccaaga | caaagttcat | 1260 |
| tactacataa | aactgaagga | cttaagagat | cagttgaaag | gcattgaacg | aaatatggac | 1320 |
| gttcaagagg | tgcaatatac | atttgaccta | cagcttgccc | aagaggatgc | aaagaagatg | 1380 |
| gctgttaagg | aagaaaaata | tgatccaggt | tatgaggcag | catatggtgg | tgcttacgga | 1440 |
| gaaaatccat | gcagcagtga | accttgtggc | ttctcttcaa | atgggctaat | tgagagcgtg | 1500 |
| gagttaagag | gagaatcagc | tttcagtggc | attcctaatg | ggcagtggat | gacccagtca | 1560 |
| tttacagacc | aaaattcctt | ctttagtaat | cactgtggaa | cacaagaaca | ggaagaagaa | 1620 |
| agccatgctt | aagaatggtg | cttctcagct | ctgcttaaat | gctgcagttt | taatgcagtt | 1680 |
| gtcaacaagt | agaaccctcag | tttgctaact | gaagtgtttt | attagtattt | tactctagtg | 1740 |
| gtgtaattgt | aatgtagaac | agttgtgtgg | tagtgtgaac | cgtatgaacc | taagtagttt | 1800 |
| ggaagaaaaa | gtagggtttt | tgtatactag | cttttgtatt | tgaattaatt | atcattccag | 1860 |
| ctttttatat | actatatttc | atttatgaag | aaattgattt | tcttttggga | gtcactttta | 1920 |
| atctgtaatt | ttaaaataca | agtctgaata | tttatagttg | attcttaact | gtgcataaac | 1980 |
| ctagatatac | cattatccct | tttataccta | agaagggcat | gctaataatt | accactgtca | 2040 |
| aagaggcaaa | ggtgttgatt | tttgtatata | agttaagcct | cagtggagtc | tcatttgtta | 2100 |
| gttttagtg | gtaactaagg | gtaaactcag | ggttccctga | gctatatgca | cactcagacc | 2160 |
| tctttgctttt | accagtggtg | tttgtgagtt | gctcagtagt | aaaaactggc | ccttacctga | 2220 |
| cagagccctg | gctttgacct | gctcagccct | gtgtgttaat | cctctagtag | ccaattaact | 2280 |
| actctggggt | ggcaggttcc | agagaatcga | gtagaccttt | tgccactcat | ctgtgtttta | 2340 |
| cttgagacat | gtaaatatga | tagggaagga | actgaatttc | tccattcata | tttataacca | 2400 |
| ttctagtttt | atcttccttg | gctttaagag | tgtgccatgg | aaagtgataa | gaaatgaact | 2460 |
| tctaggctaa | gcaaaagat | gctggagata | tttgatactc | tcatttaaac | tggtgcttta | 2520 |
| tgtacatgag | atgtactaaa | ataagtaata | tagaattttt | cttgctaggt | aaatccagta | 2580 |
| agccaataat | tttaaagatt | ctttatctgc | atcattgctg | tttgttacta | taaattaaat | 2640 |
| gaacctcatg | gaaaggttga | ggtgtatacc | tttgtgatt | tctaatgagt | tttccatggt | 2700 |
| gctacaaata | atccagacta | ccaggtctgg | tagatattaa | agctgggtac | taagaaatgt | 2760 |
| tatttgcatc | ctctcagtta | ctcctgaata | ttctgatttc | atacgtaccc | agggagcatg | 2820 |
| ctgttttgtc | aatcaatata | aaatatttat | gaggtctccc | ccaccccag | gaggttatat | 2880 |
| gattgctctt | ctctttataa | taagagaaac | aaattcttat | tgtgaatctt | aacatgcttt | 2940 |
| ttagctgtgg | ctatgatgga | ttttattttt | tcctaggtca | agctgtgtaa | aagtcattta | 3000 |
| tgttatttaa | atgatgtact | gtactgctgt | ttacatggac | gttttgtgcg | ggtgctttga | 3060 |

-continued

| | |
|---|---|
| agtgccttgc atcagggatt aggagcaatt aaattatttt ttcacgggac tgtgtaaagc | 3120 |
| atgtaactag gtattgcttt ggtatataac tattgtagct ttacaagaga ttgttttatt | 3180 |
| tgaatgggga aaatacccctt taaattatga cggacatcca ctagagatgg gtttgaggat | 3240 |
| tttccaagcg tgtaataatg atgttttccc taacatgaca gatgagtagt aaatgttgat | 3300 |
| atatcctata catgacagtg tgagactttt tcattaaata atattgaaag attttaaaat | 3360 |
| tcatttgaaa gtctgatggc ttttacaata aaagatatta agaattgtta | 3410 |

<210> SEQ ID NO 7
<211> LENGTH: 1108
<212> TYPE: DNA
<213> ORGANISM: Homo sapiens

<400> SEQUENCE: 7

| | |
|---|---|
| cctgggcccc catgcccgtg cagctcgcac atatgtgggg cagagcagcc accctgcccc | 60 |
| cagcagcagc cgtccatcgt cagacgtgat catttcctga ggcctcgagt gtgtcagggt | 120 |
| gtttgtgcct cataacaacc cacaggatgg tcaccccgc tttgcagatg aagaaaccaa | 180 |
| agcagttttg ccgacggatg gggcaaaaga agcagcgacc agctagagca gggcagccac | 240 |
| acagctcgtc cgacgcagcc caggcacctg cagagcagcc acacagctcg tccgatgcag | 300 |
| cccaggcacc ttgccccagg gagcgctgct tgggaccgcc caccactccg ggcccatacc | 360 |
| gcagcatcta tttctcaagc ccaaagggcc accttacccg actggggttg gagttcttcg | 420 |
| accagccggc agtcccctg gcccgggcat ttctgggaca ggtcctagtc cggcgacttc | 480 |
| ctaatggcac agaactccga ggccgcatcg tggagaccga ggcatacctg gggccagagg | 540 |
| atgaaccggc ccactcaagg ggtggccggc agaccccccg caaccgaggc atgttcatga | 600 |
| agccggggac cctgtacgtg tacatcattt acggcatgta cttctgcatg aacatctcca | 660 |
| gccaggggga cggggcttgc gtcttgctgc gagcactgga gccctggaa ggtctggaga | 720 |
| ccatgcgtca cgttcgcagc accctccgga aaggcaccgc cagccgtgtc ctcaaggacc | 780 |
| gcgagctctg cagtggcccc tccaagctgt gccaggccct ggccatcaac aagagctttg | 840 |
| accagaggga cctggcacag gatgaagctg tatggctgga gcgtggtccc ctggagccca | 900 |
| gtgagccggc tgtagtggca gcagcccggg tgggcgtcgg ccatgcaggg gagtgggccc | 960 |
| ggaaacccct ccgcttctat gtccggggca gcccctgggt cagtgtggtc gacagagtgg | 1020 |
| ctgagcagga cacacaggcc tgagcaaagg gcctgcccag acaagatttt ttaattgttt | 1080 |
| aaaaaccgaa taaatgtttt atttctag | 1108 |

<210> SEQ ID NO 8
<211> LENGTH: 939
<212> TYPE: DNA
<213> ORGANISM: Homo sapiens

<400> SEQUENCE: 8

| | |
|---|---|
| atgtgtagtc cgcaggagtc cggcatgacc gccttgagcg cgaggatgct gacccggagc | 60 |
| cggagcctgg gacccgggc tgggccgcgg gggtgtaggg aggagcccgg gcctctccgg | 120 |
| agaagagagg ctgcagcaga agcgaggaaa agccacagcc ccgtgaagcg tccgcggaaa | 180 |
| gcacagagac tgcgtgtggc ctatgagggc tcggacagtg agaaaggtga gggggctgag | 240 |
| cccctcaagg tgccagtctg ggagcccag gactggcagc aacagctggt caacatccgt | 300 |
| gccatgagga acaaaaagga tgcacctgtg gaccatctgg ggactgagca ctgctatgac | 360 |
| tccagtgccc ccccaaaggt acgcaggtac caggtgctgc tgtcactgat gctctccagc | 420 |

```
caaaccaaag accaggtgac ggcgggcgcc atgcagcgac tgcgggcgcg gggcctgacg    480
gtggacagca tcctgcagac agatgatgcc acgctgggca agctcatcta ccccgtcggt    540
ttctggagga gcaaggtgaa atacatcaag cagaccagcg ccatcctgca gcagcactac    600
ggtggggaca tcccagcctc tgtggccgag ctggtggcgc tgccgggtgt tgggcccaag    660
atggcacacc tggctatggc tgtggcctgg ggcactgtgt caggcattgc agtggacacg    720
catgtgcaca gaatcgccaa caggctgagg tggaccaaga aggcaaccaa gtccccagag    780
gagacccgcg ccgccctgga ggagtggctg cctagggagc tgtggcacga gatcaatgga    840
ctcttggtgg gcttcggcca gcagacctgt ctgcctgtgc accctcgctg ccacgcctgc    900
ctcaaccaag ccctctgccc ggccgcccag ggtctctga                           939

<210> SEQ ID NO 9
<211> LENGTH: 1854
<212> TYPE: DNA
<213> ORGANISM: Homo sapiens

<400> SEQUENCE: 9
ggagcctcta gaactatgag cccgaggcct tccctctctc cagagcgcag aggctttgaa     60
ggctacctct gggaagccgc tcaccgtcgg aagctgcggg agctgaaact gcgccatcgt    120
cactgtcggc ggccatgaca ccgctcgtct cccgcctgag tcgtctgtgg ccatcatga    180 ggaagccacg agcagccgtg ggaagtggtc acaggaagca ggcagccagc caggaaggga    240
ggcagaagca tgctaagaac aacagtcagg ccaagccttc tgcctgtgat gggatgattg    300
ctgagtgtcc tggggcccca gcaggcctgg ccaggcagcc ggaagaggtg gtattgcagg    360
cctctgtctc ctcataccat ctattcagag acgtagctga agtcacagcc ttccgaggga    420
gcctgctaag ctggtacgac caagagaaac gggacctacc atggagaaga cgggcagaag    480
atgagatgga cctggacagg cgggcatatg ctgtgtgggt ctcagaggtc atgctgcagc    540
agacccaggt tgccactgtg atcaactact ataccggatg gatgcagaag tggcctacac    600
tgcaggacct ggccagtgct tccctggagg aggtgaatca actctgggct ggcctgggct    660
actattctcg tggccggcgg ctgcaggagg gagctcggaa ggtggtagag gagctagggg    720
gccacatgcc acgtacagca gagaccctgc agcagctcct gcctggcgtg gggcgctaca    780
cagctggggc cattgcctct atcgcctttg gccaggcaac cggtgtggtg gatggcaacg    840
tagcacgggt gctgtgccgt gtccgagcca ttggtgctga tcccagcagc accttgttt     900 cccagcagct ctgggtcta gcccagcagc tggtggaccc agcccggcca ggagatttca    960
accaagcagc catggagcta ggggccacag tgtgtacccc acagcgccca ctgtgcagcc   1020
agtgccctgt ggagagcctg tgccgggcac gccagagagt ggagcaggaa cagctcttag   1080
cctcagggag cctgtcgggc agtcctgacg tggaggagtg tgctcccaac actggacagt   1140
gccacctgtg cctgcctccc tcggagccct gggaccagac cctgggagtg gtcaacttcc   1200
ccagaaaggc cagccgcaag ccccccaggg aggagagctc tgccacctgt gttctggaac   1260
agcctggggc ccttggggcc caaattctgc tggtgcagag gcccaactca ggtctgctgg   1320
caggactgtg ggagttcccg tccgtgacct gggagccctc agagcagctt cagcgcaagg   1380
ccctgctgca ggaactacag cgttgggctg ggccctcccc agccacgcac ctccggcacc   1440
ttggggaggt tgtccacacc ttctctcaca tcaagctgac atatcaagta tatgggctgg   1500
ccttggaagg gcagaccca gtgaccaccg taccaccagg tgctcgctgg ctgacgcagg    1560
aggaatttca caccgcagct gtttccaccg ccatgaaaaa ggttttccgt gtgtatcagg   1620
```

```
gccaacagcc agggacctgt atgggttcca aaaggtccca ggtgtcctct ccgtgcagtc    1680
ggaaaaagcc ccgcatgggc cagcaagtcc tggataattt ctttcggtct cacatctcca    1740
ctgatgcaca cagcctcaac agtgcagccc agtgacacct ctgaaagccc ccattccctg    1800
agaatcctgt tgttagtaaa gtgcttattt ttgtagttaa aaaaaaaaaa aaaa          1854

<210> SEQ ID NO 10
<211> LENGTH: 2557
<212> TYPE: DNA
<213> ORGANISM: Homo sapiens
<220> FEATURE:
<221> NAME/KEY: misc_feature
<222> LOCATION: (200)..(200)
<223> OTHER INFORMATION: any nucleotide

<400> SEQUENCE: 10
ttcgcttgaa cccgggaggc ggagcttgca gtgagccgag atcgcgccat cacactccag      60
ctcaggcgac agagtgagac tccgtctcaa agaaaaaaaa cttgcagcct gatagttaag     120
atacagcaac cccaaatccc tatgctaaaa ggtgagaatg gcccagataa aggtcatgtc     180
tcctagctcc ctgcttttn atgccatcct ccagaaggga agaaattaaa taatccatcc      240
tcctactcca ggcgactaga aggcaggctg cctcagggcc acacactggg acttggactc     300
aacctgatgg gcttctgggc ccagccccag acaaaccccc ggcaaacgtc ccattccgag     360
gaaagcatga gcagatggag tatggaagaa atgcccaaga cggcaggcag cagctgtggc     420
ggccggcggg acgacaatcc gaggagaggc ctctgatgtc ctgaggtctc agaggacgcc     480
taaaggcctt gaatgggaca agcttagcgg gcgggcgcag aagagaataa tactctggag     540
acacttcccg agggctctgg ggccggagct gtgttcgctc cggttcttgg tgaagacagg     600
gttcgtggga ggcggcccaa ggagggcgaa cgcctaagac tgcaaaggct cggggagaa      660 cggctctcgg agaacgggct ggggaaggac gtggctctga agacggacag ccctgaggaa     720
ccgcggggcg cccagatgga actcgttagc gccccgagtg cagacaatcc cggaggggga     780
aaggcgagca gctggcagag agcccagtgc cggccaaccg cgcgagcgcc tcagaacggc     840
ccgcccaccc tgatttctca ttggcgcctc ctacctcctc ctcggattgg ctacctctag     900
gtgaaatgag cggtggttga gccctacttc cggtggtgct gtggtctgcc cctggagaac     960
ccagaagaac acagctgtgc gcgcccacag gctctggggg cggagaaga taagtcgcaa    1020 ggagggggcg ggacctacac ctcaggaaag ccggagaatt ggggcacgaa gcgggctt     1080 gatgacccgc aaagggcgag gcatgcagga ggtggaggaa ttaagtgaaa cagggaaggt    1140
tgttaaacag caccgtgtgg gcgaggcctt aagggtcgtg gtccttgtct gggcggggtc    1200
tttgggcgtc gacgaggcct ggttctgggt aggcggggct actacggggc ggtgcctgct    1260
gtggaaatgc ctgcccgcgc gcttctgccc aggcgcatgg ggcatcgtac tctagcctcc    1320
actcctgccc tgtgggcctc catcccgtgc cctcgctctg agctgcgcct ggacctggtt    1380
ctgccttctg gacaatcttt ccggtggagg gagcaaagtc ctgcacactg gagtggtgta    1440
ctagcggatc aagtatggac actgactcag actgaggagc agctccactg cactgtgtac    1500
cgaggagaca agagccaggc tagcaggccc acaccagacg agctggaggc cgtgcgcaag    1560
tacttccagc tagatgttac cctggctcaa ctgtatcacc actggggttc cgtggactcc    1620
cacttccaag aggtggctca gaaattccaa ggtgtgcgac tgctgcgaca gaccccatc    1680 gaatgccttt tctcttttat ctgttcctcc aacaacaaca tcgcccgcat cactggcatg    1740
gtggagcggc tgtgccaggc ttttggacct cggctcatcc agcttgatga tgtcacctac    1800
```

| | |
|---|---:|
| catggcttcc ccagcctgca ggccctggct gggccagagg tggaggctca tctcaggaag | 1860 |
| ctgggcctgg gctatcgtgc ccgttacgtg agtgccagtg cccgagccat cctggaagaa | 1920 |
| cagggcgggc tagcctggct gcagcagcta cgagagtcct catatgagga ggcccacaag | 1980 |
| gccctctgca tcctgcctgg agtgggcacc aaggtggctg actgcatctg cctgatggcc | 2040 |
| ctagacaagc cccaggctgt gcccgtggat gtccatatgt ggcacattgc caacgtgac | 2100 |
| tacagctggg accctaccac gtcccaggcg aagggaccga gccccagac caacaaggaa | 2160 |
| ctgggaaact ttttccggag cctgtgggga ccttatgctg gctgggccca agcggtgctg | 2220 |
| ttcagtgccg acctgcgcca atcccgccat gctcaggagc accagcaaa gcgcagaaag | 2280 |
| ggttccaaag ggccggaagg ctagatgggg caccctggac aaagaaattc cccaagcacc | 2340 |
| ttcccctcca ttccccactt ctctctcccc atccccaccc agtctcatgt tggggagggg | 2400 |
| cctcctgtg actacctcaa aggccaggca cccccaaatc aagcagtcag tttgcacaac | 2460 |
| aagatggggt gggggatatt gagggagaca gcgctaagga tggttttatc ttccctttat | 2520 |
| tacaagaagg aacaataaaa tagaaacatt tgtatgg | 2557 |

<210> SEQ ID NO 11
<211> LENGTH: 643
<212> TYPE: DNA
<213> ORGANISM: Homo sapiens

<400> SEQUENCE: 11

| | |
|---|---:|
| gagcggcggt gcagaaccca gggaccatgg gcgcctccag gctctatacc ctggtgctgg | 60 |
| tcctgcagcc tcagcgagtt ctcctgggca tgaaaaagcg aggcttcggg gccggccggt | 120 |
| ggaatggctt tgggggcaaa gtgcaagaag gagagaccat cgaggatggg gctaggaggg | 180 |
| agctgcagga ggagagcggt ctgacagtgg acgccctgca caaggtgggc cagatcgtgt | 240 |
| ttgagttcgt gggcgagcct gagctcatgg acgtgcatgt cttctgcaca gacagcatcc | 300 |
| aggggacccc cgtggagagc gacgaaatgc gcccatgctg gttccagctg atcagatcc | 360 |
| ccttcaagga catgtggccc gacgacagct actggtttcc actcctgctt cagaagaaga | 420 |
| aattccacgg gtacttcaag ttccagggtc aggacaccat cctggactac acactccgcg | 480 |
| aggtggacac ggtctagcgg gagcccaggg cagcccctgg gcaggagacg tggctgctga | 540 |
| acagctgcaa accatcttca cctgggggca ttgagtggcg cagagccggg tttcatctgg | 600 |
| aattaactgg atggaaggga aaataaagct atctagcggt gaa | 643 |

<210> SEQ ID NO 12
<211> LENGTH: 1006
<212> TYPE: DNA
<213> ORGANISM: Homo sapiens

<400> SEQUENCE: 12

| | |
|---|---:|
| cgtctcctcg ctcgccttct ggctctgcca tgccctgctc tgaagagaca cccgccattt | 60 |
| cacccagtaa gcgggcccgg cctgcggagg tgggcggcat gcagctccgc tttgcccggc | 120 |
| tctccgagca cgccacggcc cccacccggg gctccgcgcg cgccgcgggc tacgacctgt | 180 |
| acagtgccta tgattacaca ataccaccta tggagaaagc tgttgtgaaa acggacattc | 240 |
| agatagcgct cccttctggg tgttatggaa gagtggctcc acggtcaggc ttggctgcaa | 300 |
| aacactttat tgatgtagga gctggtgtca tagatgaaga ttatagagga aatgttggtg | 360 |
| ttgtactgtt taattttggc aaagaaaagt ttgaagtcaa aaaaggtgat cgaattgcac | 420 |
| agctcatttg cgaacggatt ttttatccag aaatagaaga agttcaagcc ttggatgaca | 480 |

```
ccgaaagggg ttcaggaggt tttggttcca ctggaaagaa ttaaaattta tgccaagaac    540
agaaaacaag aagtcatacc ttttcttaa aaaaaaaaa agtttttgct tcaagtgttt     600 tggtgtttg cacttctgta aacttactag ctttaccttc taaaagtact gcatttttta    660 cttttttta tgatcaagga aaagatcatt aaaaaaaaac acaaagaag ttttctttg      720 tgtttggatc aaaagaaac tttgtttttc cgcaattgaa ggttgtatgt aaatctgctt    780
tgtggtgacc tgatgtaaac agtgtcttct taaaatcaaa tgtaaatcaa ttacagatta   840
aaaaaaaaaa gcctgtattt aactcatatg atctcccttc agcaacttat tttgctttaa   900
ttgctttaaa tcttaagcaa tattttttat tcagtaaaca aattctttca caaggtacaa   960
aatcttgcat aagctgaact aaaataaaaa tgaaaggag agatta                    1006
```

<210> SEQ ID NO 13
<211> LENGTH: 1420
<212> TYPE: DNA
<213> ORGANISM: Homo sapiens

<400> SEQUENCE: 13

```
tgccatcggg ccggtgcaga tacggggttg ctctttgct cataagaggg gcttcgctgg     60
cagtctgaac ggcaagcttg agtcaggacc cttaattaag atcctcaatt ggctggaggg   120
cagatctcgc gagtagggca acgcggtaaa aatattgctt cggtgggtga cgcggtacag   180
ctgcccaagg gcgttcgtaa cgggaatgcc gaagcgtggg aaaaagggag cggtggcgga   240
agacggggat gagctcagga cagagccaga ggccaagaag agtaagacgg ccgcaaagaa   300
aaatgacaaa gaggcagcag gagagggccc agccctgtat gaggaccccc cagatcacaa   360
aacctcaccc agtggcaaac ctgccacact caagatctgc tcttggaatg tggatgggct   420
tcgagcctgg attaagaaga aaggattaga ttgggtaaag aagaagcccc cagatatact   480
gtgccttcaa gagaccaaat gttcagaaa caaactacca gctgaacttc aggagctgcc   540
tggactctct catcaatact ggtcagctcc ttcggacaag gaagggtaca gtggcgtggg   600
cctgctttcc cgccagtgcc cactcaaagt ttcttacggc ataggcgatg aggagcatga   660
tcaggaaggc cgggtgattg tggctgaatt tgactcgttt gtgctggtaa cagcatatgt   720
acctaatgca ggccgaggtc tggtacgact ggagtaccgg cagcgctggg atgaagcctt   780
tcgcaagttc ctgaagggcc tggcttcccg aaagcccctt gtgctgtgtg agacctcaa   840 tgtggcacat gaagaaattg accttcgcaa ccccaagggg aacaaaaaga atgctggctt   900
cacgccacaa gagcgccaag gcttcgggga attactgcag gctgtgccac tggctgacag   960
ctttaggcac ctctacccca acacacccta tgcctacacc ttttggactt atatgatgaa  1020
tgctcgatcc aagaatgttg gttggcgcct tgattacttt ttgttgtccc actctctgtt  1080
acctgcattg tgtgacagca agatccgttc caaggccctc ggcagtgatc actgtcctat  1140
caccctatac ctagcactgt gacaccaccc taaatcact ttgagcctgg gaaataagcc   1200
ccctcaacta ccattccttc tttaaacact cttcagagaa atctgcattc tattctcat   1260 gtataaaact aggaatcctc caaccaggct cctgtgatag agttctttta agcccaagat  1320
tttttatttg agggttttt gttttttaaa aaaaattga acaaagacta ctaatgactt    1380
tgtttgaatt atccacatga aaataaagag ccatagtttc                          1420
```

<210> SEQ ID NO 14
<211> LENGTH: 1259
<212> TYPE: DNA
<213> ORGANISM: Homo sapiens

```
<400> SEQUENCE: 14
ccggagctgg gttgctcctg ctcccgtctc caagtcctgg tacctccttc aagctgggag      60
agggctctag tccctggttc tgaacactct ggggttctcg ggtgcaggcc gccatgagca     120 aacgaaggc gccgcaggag actctcaacg ggggaatcac cgacatgctc acagaactcg     180
caaactttga gaagaacgtg agccaagcta tccacaagta caatgcttac agaaaagcag     240
catctgttat agcaaaatac ccacacaaaa taaagagtgg agctgaagct aagaaattgc     300
ctggagtagg aacaaaaatt gctgaaaaga ttgatgagtt tttagcaact ggaaaattac     360
gtaaactgga aaagattcgg caggatgata cgagttcatc catcaatttc ctgactcgag     420
ttagtggcat tggtccatct gctgcaagga agtttgtaga tgaaggaatt aaaacactag     480
aagatctcag aaaaaatgaa gataaattga accatcatca gcgaattggg ctgaaatatt     540
ttggggactt tgaaaaaaga attcctcgtg aagagatgtt acaaatgcaa gatattgtac     600
taaatgaagt taaaaaagtg gattctgaat acattgctac agtctgtggc agtttcagaa     660
gaggtgcaga gtccagtggt gacatggatg ttctcctgac ccatcccagc ttcacttcag     720
aatcaaccaa acagccaaaa ctgttacatc aggttgtgga gcagttacaa aaggttcatt     780
ttatcacaga taccctgtca aagggtgaga caaagttcat gggtgtttgc cagcttccca     840
gtaaaaatga tgaaaaagaa tatccacaca gaagaattga tatcaggttg atacccaaag     900
atcagtatta ctgtggtgtt ctctatttca ctgggagtga tattttcaat aagaatatga     960
gggctcatgc cctagaaaag ggtttcacaa tcaatgagta caccatccgt cccttgggag    1020
tcactggagt tgcaggagaa cccctgccag tggatagtga aaaagacatc tttgattaca    1080
tccagtggaa ataccgggaa cccaaggacc ggagcgaatg aggcctgtat cctccctggc    1140
agacacaacc caataggagt cttaatttat ttcttaacct ttgctatgta agggtctttg    1200
gtgtttttaa atgattgttt cttcttcatg cttttgcttg caatgtagtc aataaaacc    1259
```